(12) United States Patent
Shen et al.

(10) Patent No.: US 12,240,907 B2
(45) Date of Patent: Mar. 4, 2025

(54) N-TERMINAL scFv MULTISPECIFIC BINDING MOLECULES

(71) Applicant: Regeneron Pharmaceuticals, Inc., Tarrytown, NY (US)

(72) Inventors: Yang Shen, Scarsdale, NY (US); Ann-Hwee Lee, Ardsley, NY (US); Yan Yang, Mamaroneck, NY (US); Chia-Yang Lin, Scarsdale, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 432 days.

(21) Appl. No.: 17/088,918

(22) Filed: Nov. 4, 2020

(65) Prior Publication Data
US 2021/0130477 A1 May 6, 2021

Related U.S. Application Data

(60) Provisional application No. 62/930,916, filed on Nov. 5, 2019.

(51) Int. Cl.
*C07K 16/28* (2006.01)
*C07K 16/40* (2006.01)

(52) U.S. Cl.
CPC ...... *C07K 16/2863* (2013.01); *C07K 16/2896* (2013.01); *C07K 16/40* (2013.01); *C07K 2317/31* (2013.01); *C07K 2317/35* (2013.01); *C07K 2317/52* (2013.01); *C07K 2317/522* (2013.01); *C07K 2317/54* (2013.01); *C07K 2317/55* (2013.01); *C07K 2317/565* (2013.01); *C07K 2317/622* (2013.01); *C07K 2317/92* (2013.01)

(58) Field of Classification Search
None
See application file for complete search history.

(56) References Cited

U.S. PATENT DOCUMENTS

| 2010/0247531 | A1* | 9/2010 | Ashkenazi | A61P 35/00 |
|---|---|---|---|---|
| | | | | 435/69.6 |
| 2016/0355600 | A1 | 12/2016 | Moore et al. | |
| 2017/0320967 | A1 | 11/2017 | Yang et al. | |
| 2018/0127501 | A1 | 5/2018 | Bernett et al. | |
| 2018/0355017 | A1* | 12/2018 | Baik | C12N 9/14 |

FOREIGN PATENT DOCUMENTS

| WO | WO2010111367 A1 | 9/2010 |
|---|---|---|
| WO | WO2015013671 A1 | 1/2015 |
| WO | 2015/148708 A1 | 10/2015 |
| WO | WO2016173605 A1 | 11/2016 |
| WO | WO2017134197 A1 | 8/2017 |
| WO | WO2017218707 A2 | 12/2017 |
| WO | 2018/045110 A1 | 3/2018 |
| WO | WO2019005640 A2 | 1/2019 |
| WO | 2019/212965 A1 | 11/2019 |

OTHER PUBLICATIONS

Van Blarcom et al., MABS 10(2): 256-268 (Year: 2018).*
Bates et al., 2019, "David vs. Goliath: The Structure, Function, and Clinical Prospects of Antibody Fragments," Antibodies 8(28):2-3188.
Chiu et al., 2016, "Engineering Antibody Therapeutics," Current Opinion in Structural Biology 38:163-173.
Cuesta et al., 2010, "Multivalent Antibodies: When Design Surpasses Evolution," Trends in Biology 28(7):355-362.
De Goei et al., 2016, "Efficient Payload Delivery by a Bispecific Anti-body Drug Conjugate Targeting HER2 and CD63" Mol Cancer Ther. 15(11):2688-2697.
Dimasi et al., 2019, "Molecular Engineering Strategies and Methods for the Expression and Purification of IgG1-Based Bispecific Bivalent Antibodies," Methods 154: 77-86.
Elgundi et al., 2017, "The State-of-play and Future of Antibody Therapeutics," Advanced Drug Delivery Reviews 122:2-19.
Gu et al., 2010, "Rationale and Development of Multispecific Antibody Drugs," Expert Review of Clinical Pharmacology 1-2.
Ha et al., 2016, "Immunoglobulin Fc Heterodimer Platform Technology: From Design to Applications in Therapeutic Antibodies and Proteins," Frontiers in Immunology 7:1-16.
Huang et al., 2016, "Bispecific Antibody Case Studies," Lake Pharma: The Biologics Company, PowerPoint 1-28.
Husain et al., 2018, "Expanding the Boundaries of Biotherapeutics with Bispecific Antibodies" Biodrugs 32(5):441-464.
Kareva et al., 2018, "Guiding Principles for Mechanistic Modeling of Bispecific Antibodies," ScienceDirect 139:59-72.
Klein et al., 2019, "Engineering Therapeutic Bispecific Antibodies Using CrossMab Technology," Methods 154:21-31.
Koch et al., 2017, "Recombinant Antibodies to Arm Cytotoxic Lymphocytes in Cancer Immunotherapy," Transfusion Medicine and Hemotherapy 44:337-350.
Kontermann et al., 2012, "Dual Targeting Strategies with Bispecific Antibodies," mAbs 4(2):182-197.
Kontermann et al., 2015, "Bispecific Antibodies," Drug Discovery Today 20(7):838-847.
Labrijn et al., 2019, "Bispecific Antibodies: a Mechanistic Review of the Pipeline," Nature Reviews Drug Discovery 1-24.
Liu et al., 2017, "Fc Engineering for Developing Therapeutic Bispecific Antibodies and Novel Scaffolds," Frontiers in Immunology 8(38): 1-15.
Mertens, Nico, 2011, "Tribodies: Fab-scFv Fusion Proteins as a Platform to Create Multi-functional Pharmaceuticals," Bispecific Antibodies 135-149.

(Continued)

*Primary Examiner* — Phuong Huynh
(74) *Attorney, Agent, or Firm* — Biospark Intellectual Property Law

(57) ABSTRACT

Multispecific binding molecules (MBMs) comprising an N-terminal scFv, a first Fab and a second Fab, MBM conjugates comprising the MBMs and cytotoxic or cytostatic agents, pharmaceutical compositions containing the MBMs and MBM conjugates, methods of using the MBMs, MBM conjugates and pharmaceutical compositions for treating cancer, nucleic acids encoding the MBMs, cells engineered to express the MBMs, and methods of producing MBMs.

Figure 1:
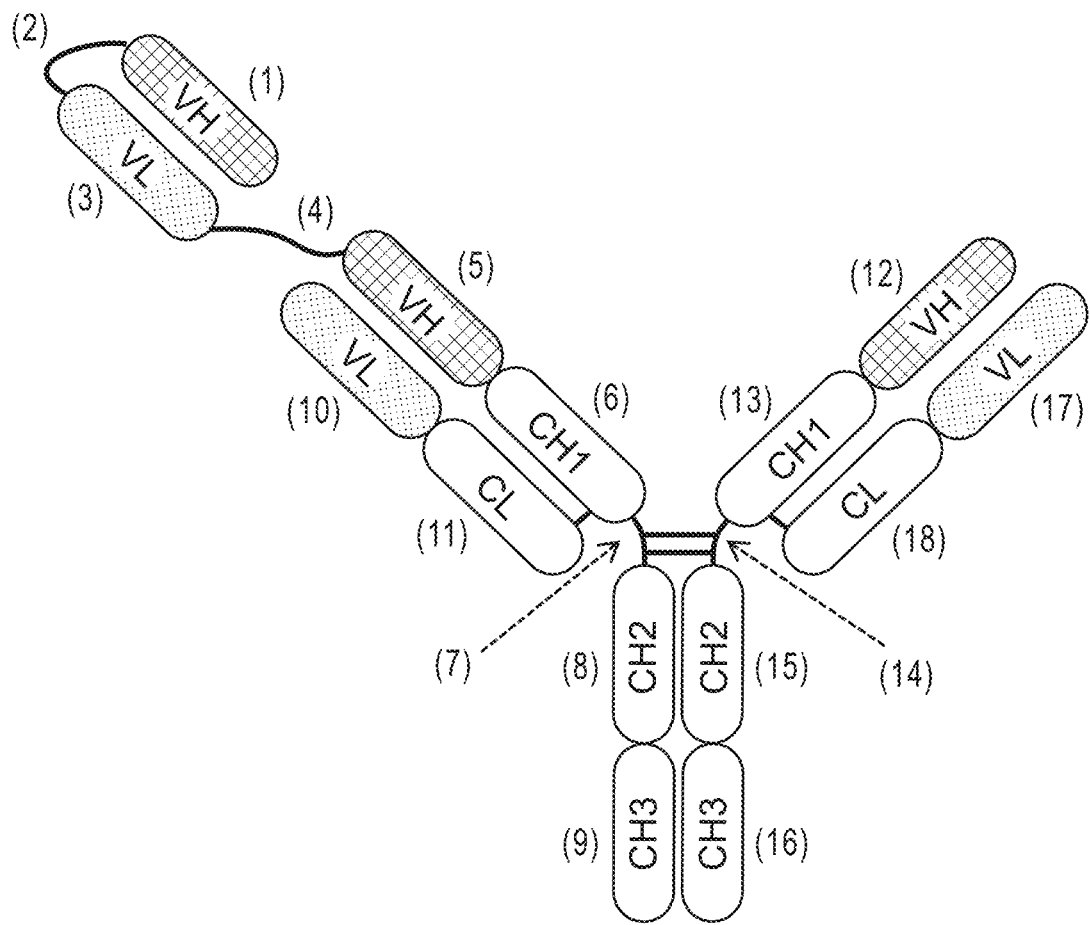

18 Claims, 25 Drawing Sheets
Specification includes a Sequence Listing.

(56) References Cited

OTHER PUBLICATIONS

Middleburg et al., 2021, "Overcoming Challenges for CD3-Bispecific Antibody Therapy in Solid Tumors," Cancers 13(287):1-25.

Moore et al., 2019, "A Robust Heterodimeric Fc Platform Engineered for Efficient Development of Bispecific Antibodies of Multiple Formats," Methods 154:38-50.

Notification of Transmittal of the International Search Report and Written Opinion of the International Searching Authority for International Application No. PCT/US2020/058798 dated Feb. 23, 2021, including International Search report and Written Opinion.

Nyakatura et al., 2018, "Design and Evaluation of Bio and Trispecific Antibodies Targeting Multiple Filovirus Glycoproteins," JBC Papers 1-19.

Padte et al., 2018, "Engineering Multi-specific Antibodies Against HIV-1," Retrovirology 15(60):1-17.

Runcie et al., 2018, "Bi-specific and Tri-specific Antibodies—the Next Big Thing in Solid Tumor Therapeutics," Molecular Medicine 24(50):1-15.

Schanzer et al., 2014, "A Novel Glycoengineering Bispecific Antibody Format for Targeted Inhibition of Epidermal Growth Factor Receptor (EGFR) and Insulin-like Growth Factor Receptor Type I (IGF-1R) Demonstrating Unique Molecular Properties," The Journal of Biological Chemistry 289(27): 18693-18706.

Smith et al., 2015, "A Novel, Native-format Bispecific Antibody Triggering T-cell Killing of B-cells is Robustly Active in Mouse Tumor Models and Cynomolgus Monkeys," Scientific Reports 5(17943):1-12.

Spiess et al., 2015, "Alternative Molecular Formats and Therapeutic Applications for Bispecific Antibodies," Molecular Immunology 67:95-106.

Steinmetz et al., 2016, "COVG-Ig, a Universal Bispecific Tetravalent and Multifunctional Immunoglobulin Format for Medical Applications," mAbs 8(5): 867-878.

Surguladze et al., 2019, "LY3076226, a novel anti-FGFR3 antibody drug conjugate exhibits potent and durable anti-tumor activity in tumor models harboring FGFR3 mutations or fusions" Cancer Res. 79(13S):4835.

Weidle et al., 2013, "The Intriguing Options of Multispecific Antibody Formats for Treatment of Cancer," Cancer Genomics & Proteomics 10: 1-18.

Weidle et al., 2014, "Tumor-Antigen-Binding Bispecific Antibodies for Cancer Treatment," Seminars in Oncology 41(5):653-660.

Wu et al., 2015, "Fab-based Bispecific Antibody Formats with Robust Biophysical Properties and Biological Activity," mAbs 7(3):470-482.

Wu et al., 2019, "Building Blocks for Bispecific and Trispecific Antibodies," Methods 154:3-9.

Yang et al., 2020, "Alternative format bispecific antibodies targeting multiple oncogenic FGFR3 mutations in bladder cancer through different mechanisms" Cancer Res. 80(16S):526.

You et al., 2021, "Bispecific Antibodies: A Smart Arsenal for Cancer Immunotherapies," Vaccines 724:1-28.

Edwards et al., 2003 "The Remarkable Flexibility of the Human Antibody Repertoire; Islocation of Over One Thousand Different Antibodies to a Single Protein, BLyS" J. Mol. Biol. 334: 103-118.

Lloyd et al., 2008 "Modelling the human immune response: performance of a 10" human antibody repertoire against a broad panel of therapeutically relevant antigens" Protein Engineering, Design & Selectioni, 22(3): 159-168.

Piche-Nicholas et al., 2018 "Changes in complementary-determining regions significantly alter IgG binding to the neonatal Fc receptor (FcRn) and pharmacokinetics" MABS 10(1): 81-94.

Yu et al., 2008 "Interaction between Bevacizumab and Murine VEGF-A: A Reassessment" Investigative Ophthalmology & Visual Science, 49(2):522-527.

DeVay et al., 2017, "Improved Lysosomal Trafficking Can Modulate the Potency of Antibody Drug Conjugates," Bioconjugate Chem. 28: 1102-1114.

* cited by examiner

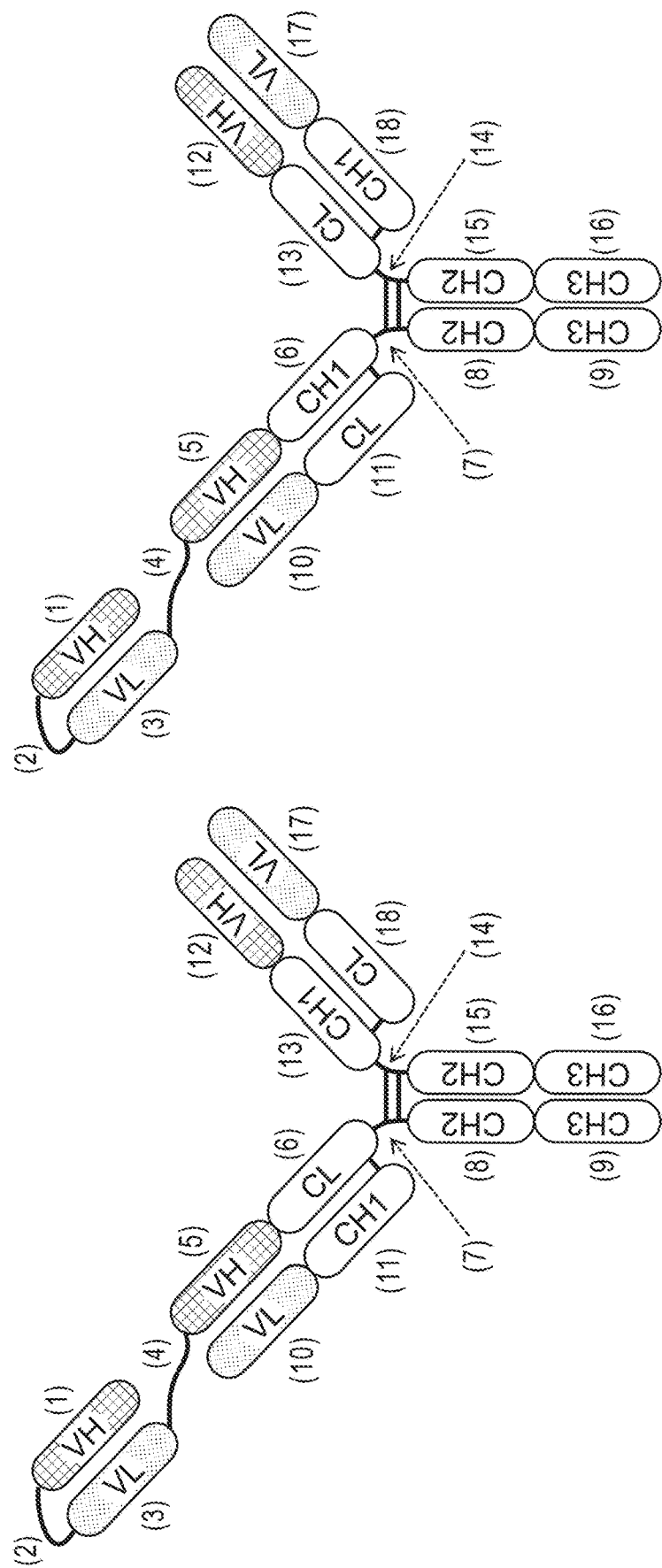

UVL: The VL of a universal light chain capable of pairing
with VH domain (5) and VH domain (12)

CH3*: CH3 with H435R Y436F modification

CH3(K) and CH3(H): CH3 with knob-in-hole modifications

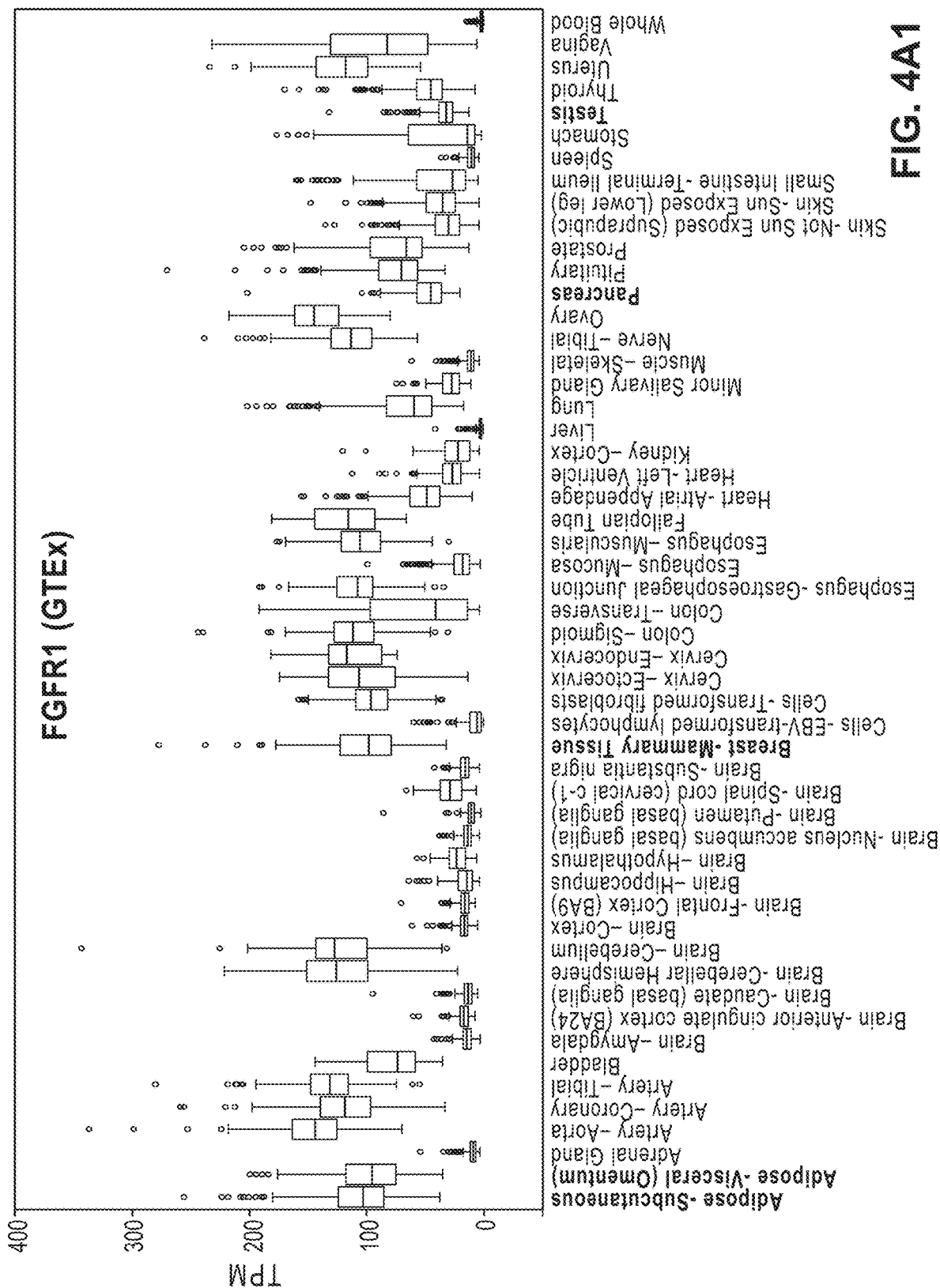
FIG. 4A1

Figure 2D:
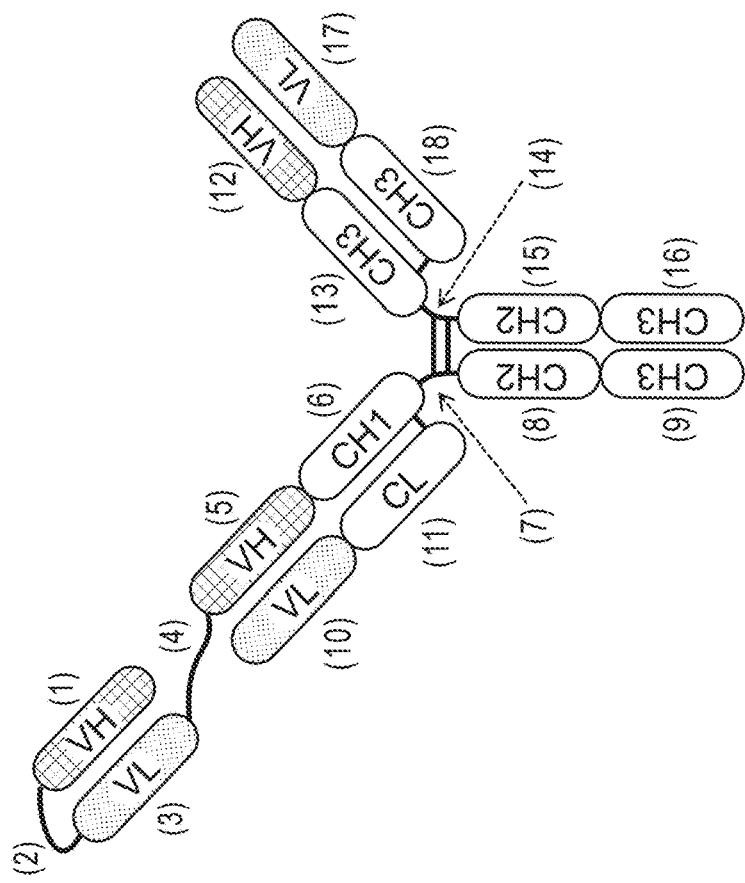

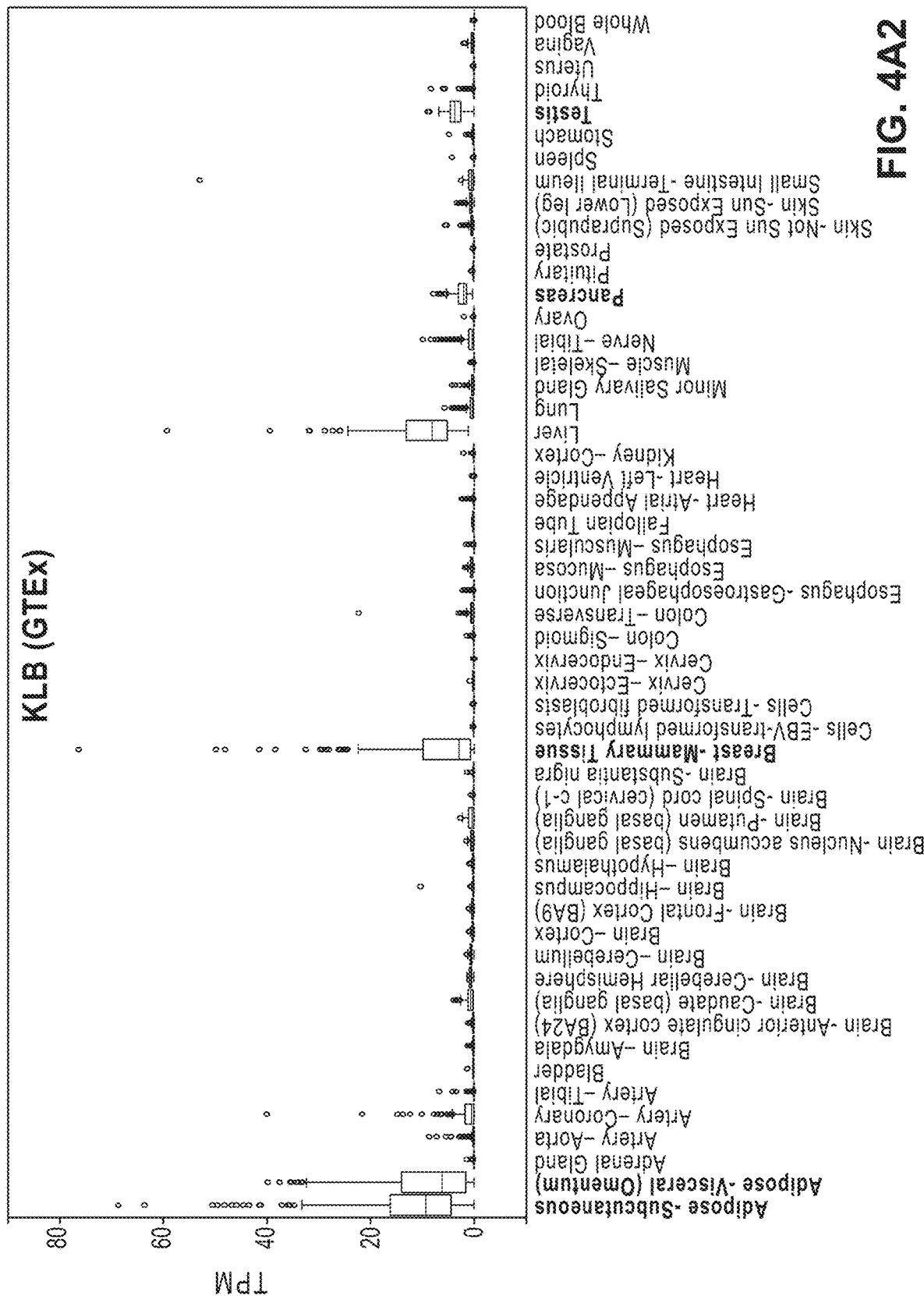
FIG. 4A2

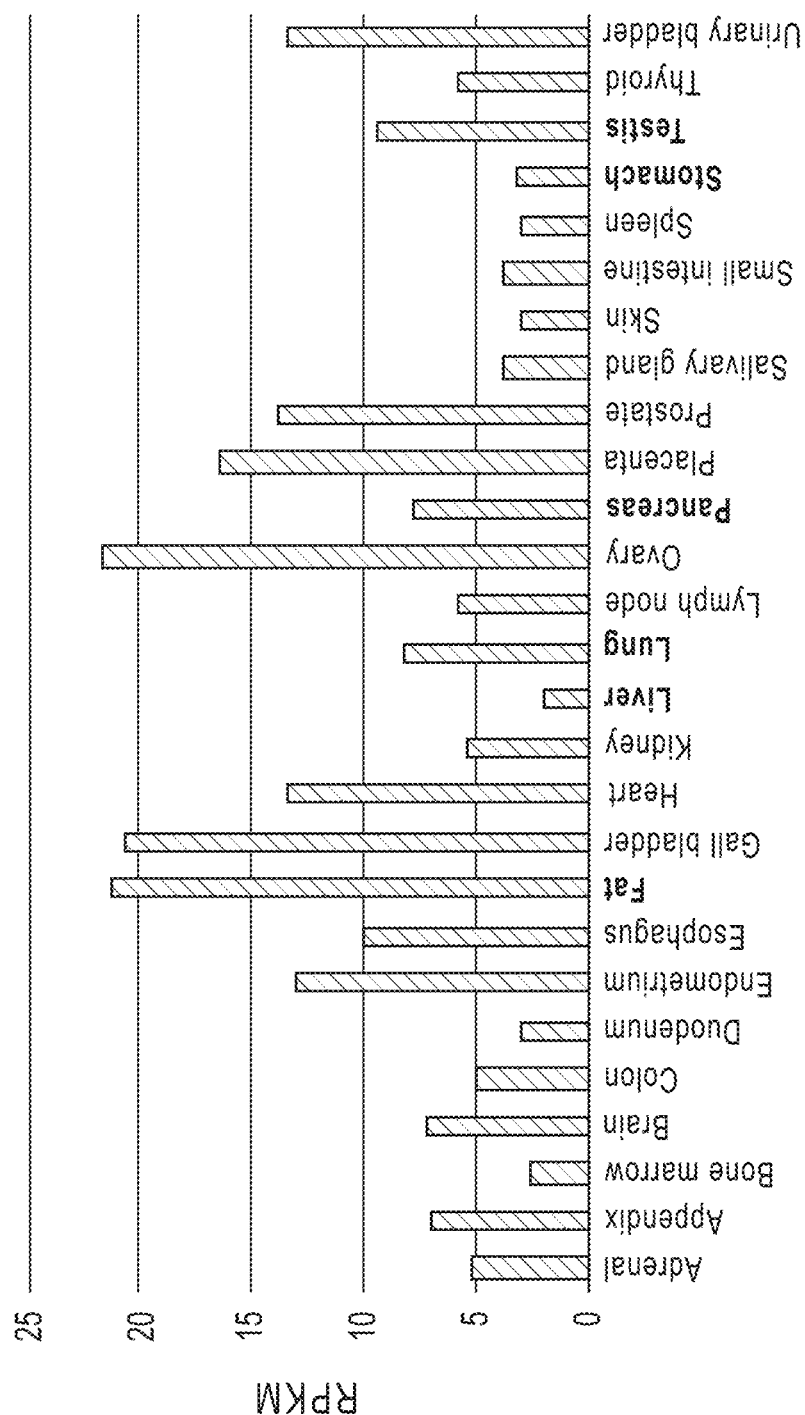
FIG. 4B1

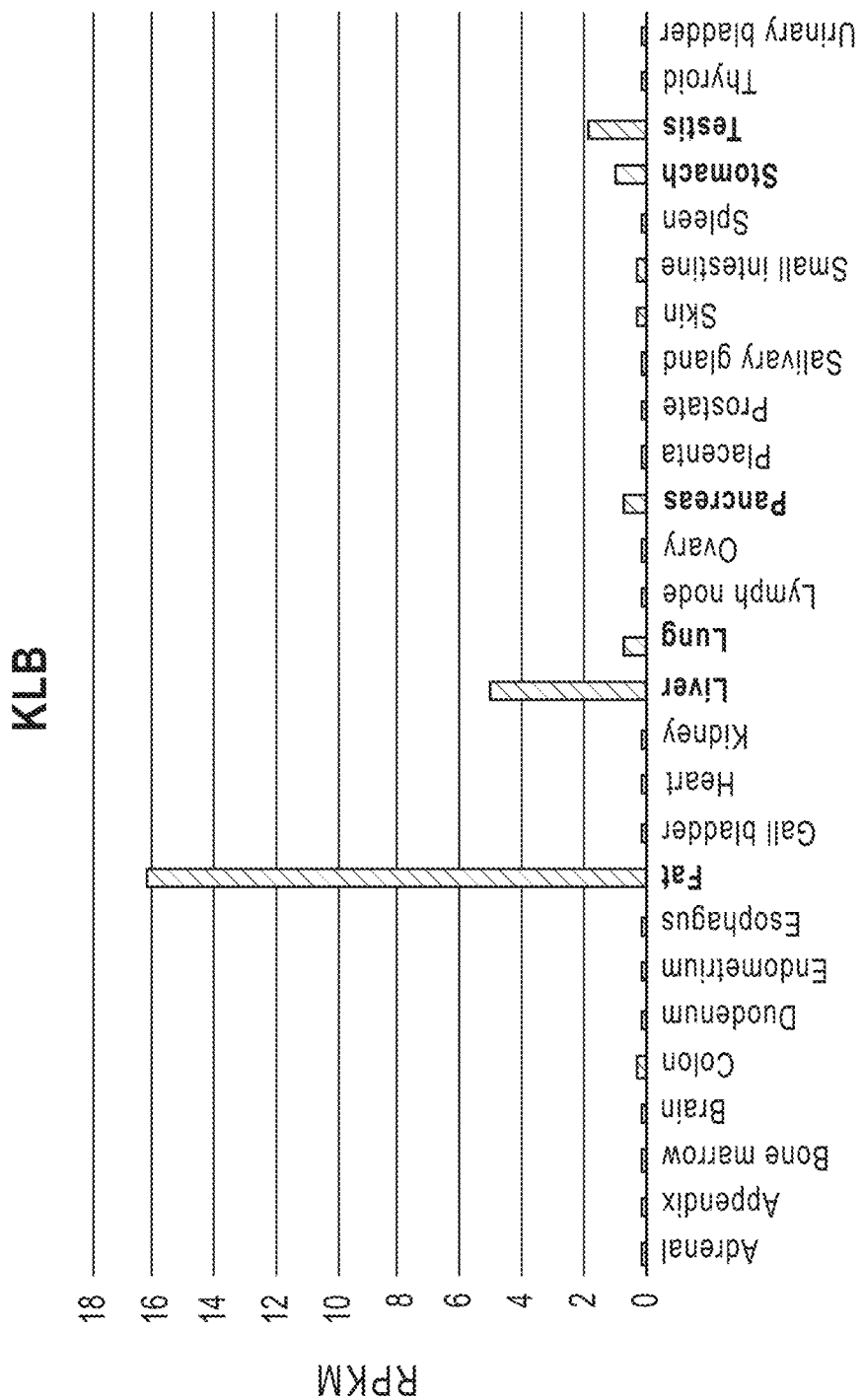
FIG. 4B2

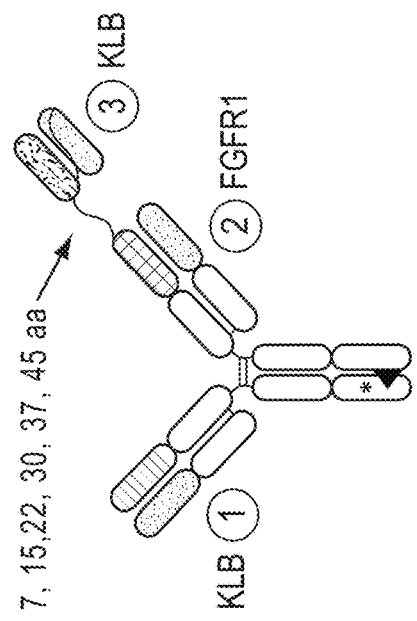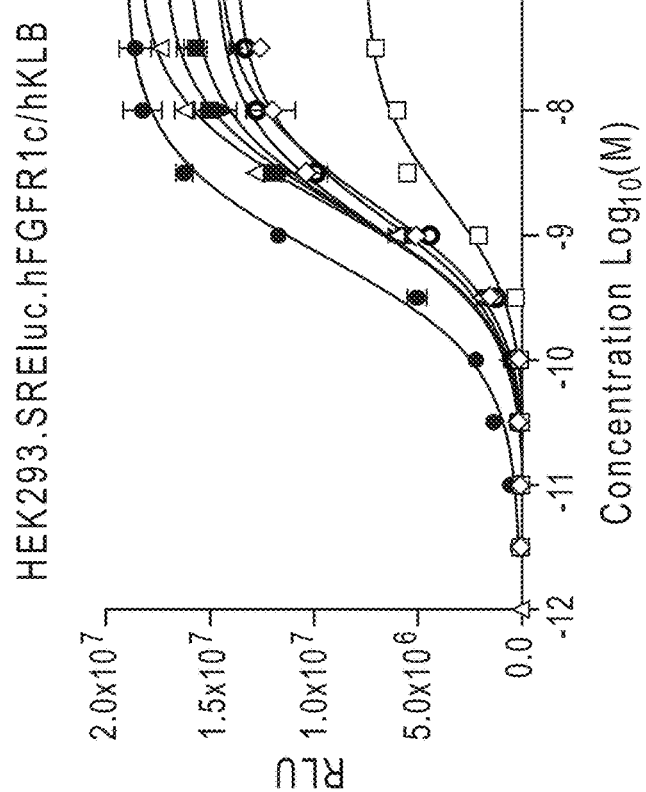
FIG. 9

N-TERMINAL scFv MULTISPECIFIC BINDING MOLECULES

1. CROSS-REFERENCE TO RELATED APPLICATIONS

This application claims the priority benefit of U.S. provisional application No. 62/930,916, filed Nov. 5, 2019, the contents of which are incorporated herein in their entireties by reference thereto.

2. SEQUENCE LISTING

The instant application contains a Sequence Listing which has been submitted electronically in ASCII format and is hereby incorporated by reference in its entirety. Said ASCII copy, created on Nov. 2, 2020, is named RGN-003US-_SL.txt and is 60.9 kilobytes in size.

3. BACKGROUND

Most naturally occurring antibody molecules in general comprise two so called light chain polypeptides (light chain) and two so called heavy chain polypeptides (heavy chain). Each of the heavy and light chain polypeptides contains a variable domain (variable region) (generally the amino terminal portion of the polypeptide chain) comprising binding regions that are able to interact with an antigen. Each of the heavy and light chain polypeptides comprises a constant region (generally the carboxyl terminal portion).

Recombinant monoclonal antibodies, which are produced by a single clone of cells or cell line, have emerged as a very successful class of biological drugs for the treatment of a variety of different diseases during the past two decades. Antibody-based therapeutics have been used successfully to treat a variety of diseases, including cancer and autoimmune/inflammatory disorders.

Due to the biological complexity of some diseases, antibodies that target more than one antigen or epitope can be more effective than single antibodies in treating certain conditions. See, e.g., Lindzen et al., 2010, Proc. Natl. Acad. Sci. 107(28): 12550-12563; Nagorsen and Baeuerle, 2011, Exp. Cell Res. 317(9): 1255-60. These antibodies offer the promise of greater therapeutic control. For example, a need exists to improve target specificity in order to reduce the off-target effects associated with many antibody therapies, particularly in the case of antibody based immunotherapies. In addition, multispecific antibodies offer new therapeutic strategies, such as synergistic targeting of multiple cell receptors, especially in an immunotherapy context.

4. SUMMARY

The present disclosure provides multispecific binding molecules ("MBMs"), containing at least three antigen-binding sites ("ABS"), two of which are Fabs and the third of which is an scFv attached to one of the Fabs at the N-terminus of the VH domain. The MBMs of the disclosure contain an Fc domain composed of two heavy chain Fc domains associated with one another. Each polypeptide chain comprising an Fc domain, and any associated polypeptide chains, is referred to herein as a "half antibody".

An exemplary MBM of the disclosure is illustrated in FIG. 1, with variations illustrated in FIG. 2 and FIG. 3.

Figure 2C:
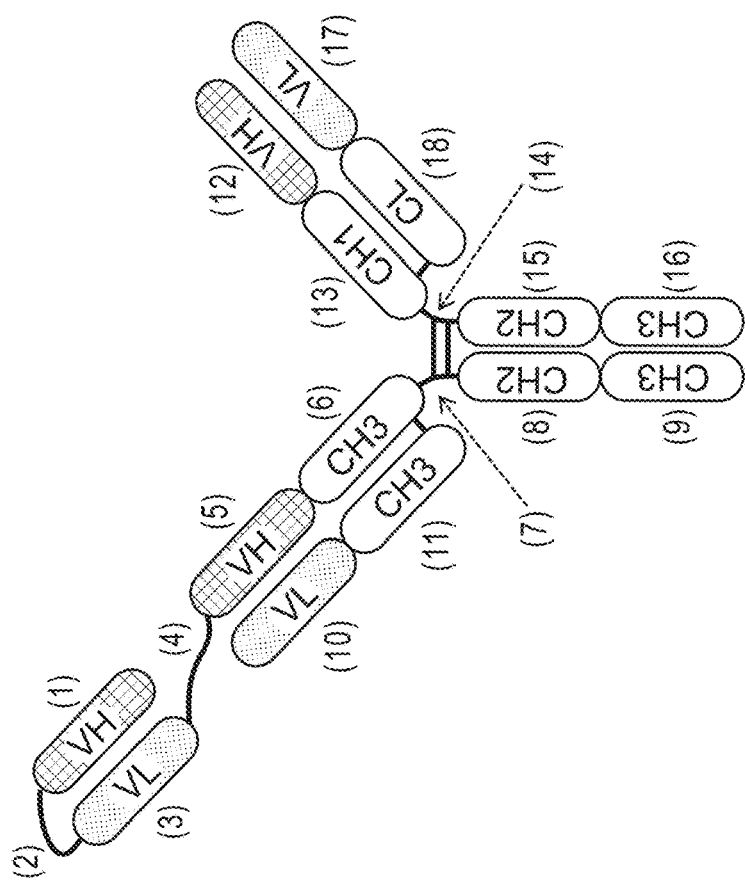
Figure 2E:
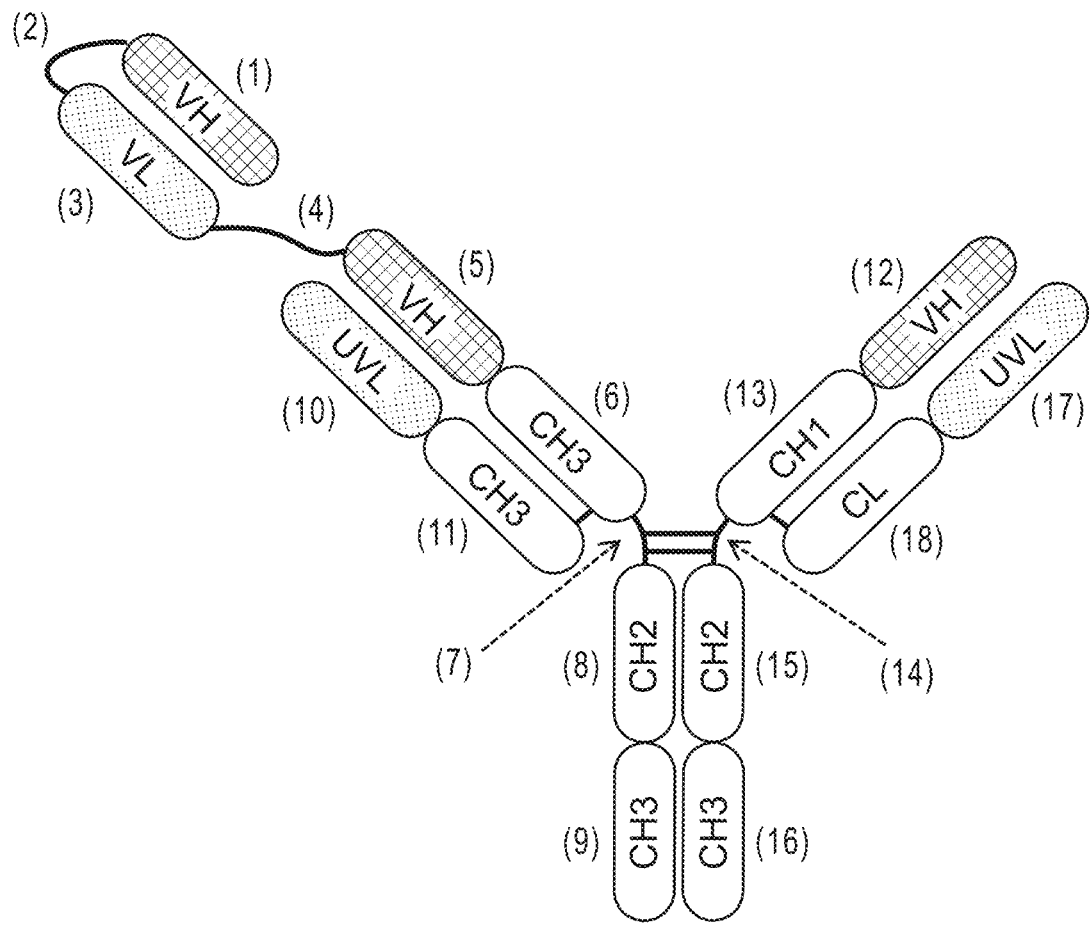
Figure 3A:
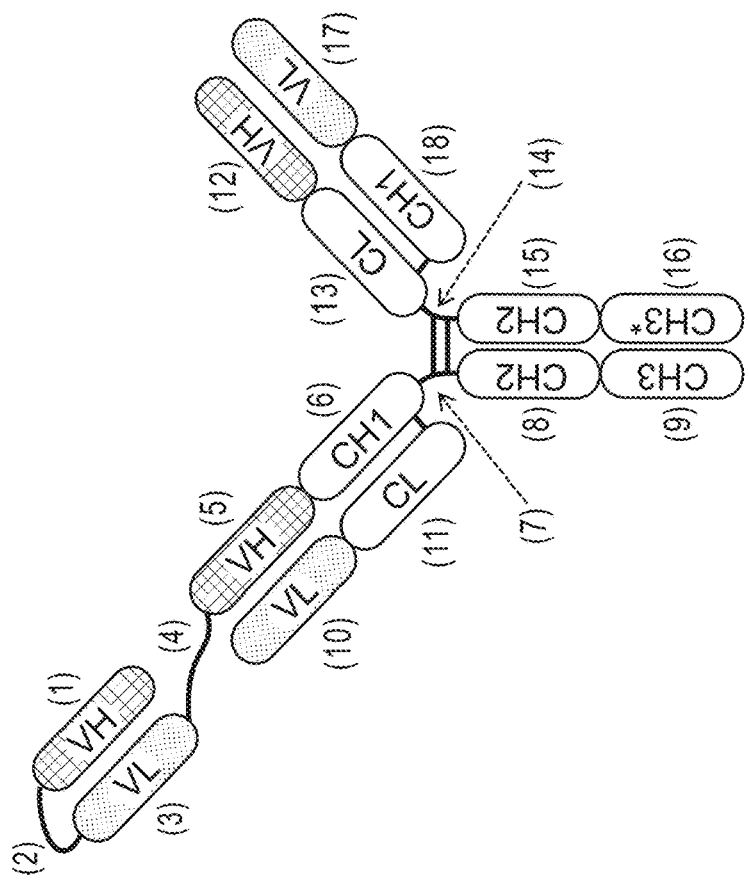
Figure 3B:
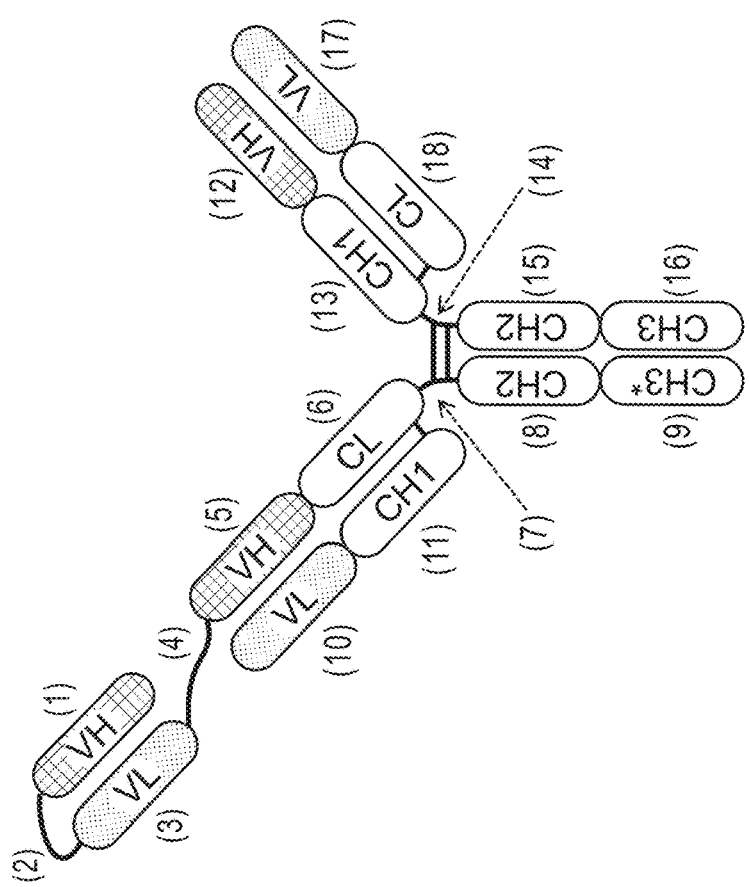
Figure 3C:
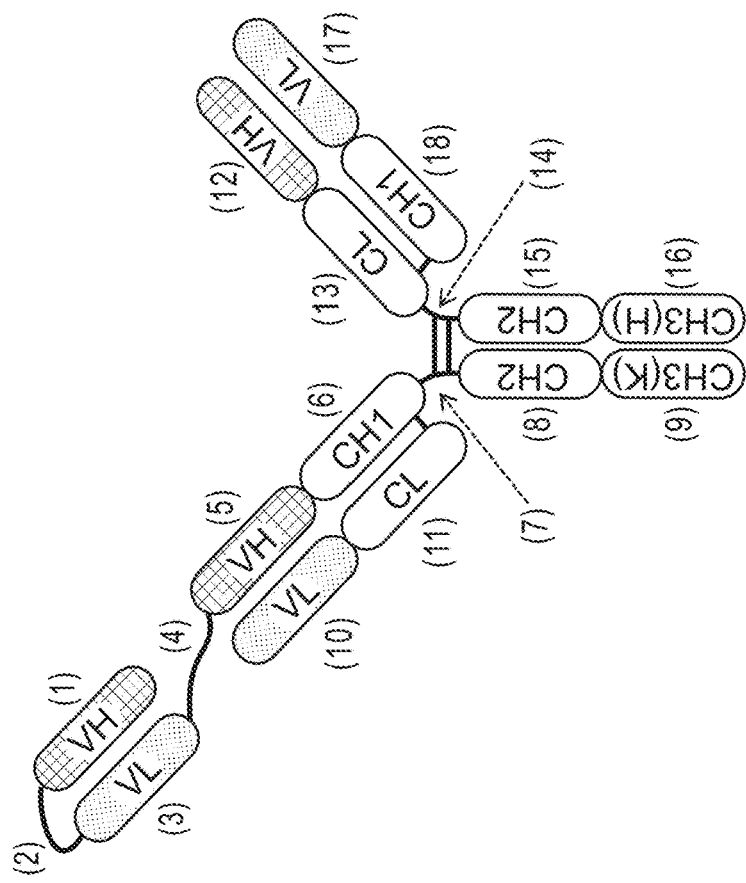

A typical MBM of the disclosure comprises two half antibodies associated through their Fc domains. The half antibody illustrated on the left of FIGS. 1-3 comprises, in the N- to C-terminal direction:

- an scFv composed of a VH (1) and a VL (3) (in either order) connected by an optional linker (2);
- an optional linker (4);
- a first Fab ("Fab1") composed of:
  - a VH (5) and a constant domain (6), which in the example of FIG. 1 is a CH1 domain but as shown in FIG. 2A and FIG. 2C can be a different type of constant domain such as a CL or a CH3 to facilitate Fab heterodimerization, associated with:
  - a VL (10) and a constant domain (11), which in the example of FIG. 1 is a CL but as shown in FIG. 2A and FIG. 3C can be a different type of constant domain such as a CH1 or a CH3;
- an optional hinge domain (7);
- an Fc domain composed of a CH2 domain (8) and a CH3 domain (9) which, as shown in FIG. 3, can contain one or more mutations (such as star mutations or knob-in-hole mutations) to facilitate heterodimerization.

The left half antibody is composed of two polypeptide chains, the first polypeptide chain comprising the VL (10) and constant domain (11) and associated with the second polypeptide chain comprising the remaining domains configured as illustrated in FIGS. 1-3.

The half antibody illustrated on the right of FIG. 1 comprises, in the N- to C-terminal direction:

- a second Fab ("Fab2") composed of:
  - a VH (12) and a constant domain (13), which in the example of FIG. 1 is a CH1 domain but as shown in FIG. 2B and FIG. 2D can be a different type of constant domain such as a CL or a CH3 to facilitate Fab heterodimerization, associated with:
  - a VL (17) and a constant domain (18), which in the example of FIG. 1 is a CL but as shown in FIG. 2B and FIG. 2D can be a different type of constant domain such as a CH1 or a CH3;
- an optional hinge domain (14);
- an Fc domain composed of a CH2 domain (15) and a CH3 domain (16) which, as shown in FIG. 3, can contain one or more mutations (such as star mutations or knob-in-hole mutations) to facilitate purification and/or assembly of heterodimers.

The right half antibody is composed of two polypeptide chains, the first polypeptide chain comprising the VL (17) and constant domain (18) and associated with the second polypeptide chain comprising the remaining domains configured as illustrated in FIGS. 1-3.

The complete MBM is formed by association of the two half antibodies through the two Fc domains to form an Fc region, resulting in an MBM with an scFv having a first antigen binding site ("ABS1"), a Fab1 having a second antigen binding site ("ABS2"), and a Fab3 has a third antigen binding site ("ABS3").

The variations of the MBMs of the disclosure shown in FIGS. 1-3 are not intended to be limiting; the MBMs, of the disclosure can include any combination of modifications illustrated in FIGS. 1-3 and in Section 6.2, infra, among others. Further, referencing a first or second polypeptide chain or a left or right half antibody is for the sake of convenience only and is not intended to convey that the polypeptide chains or half antibodies are produced or assembled in any particular order.

ABS1, ABS2, and ABS3 of MBMs, of the disclosure each bind to a target molecule, for example a cell-surface expressed antigen. Preferably, the scFv, Fab1, and Fab2 of an MBM are selected so that each of ABS1, ABS2, and ABS3 is capable of binding its respective target at the same time. In some embodiments, ABS1, ABS2, and ABS3 of an MBM can each bind a different target molecule or, alternatively, two of ABS1, ABS2, and ABS3 can bind to different regions on the same target molecule.

Advantageously, MBMs binding at least two or more different target molecules can be used, for example, to preferentially target a specific tissue type on which such two or more target molecules are expressed.

scFvs that can be used in the MBMs, of the disclosure are described in Section 6.2.1 and specific embodiments 1 to 12, 19 to 20, 31 to 35 and 55 to 60, infra. Fabs that can be used in the MBMs of the disclosure are described in Section 6.2.2 and specific embodiments 1 to 12, 19 to 20, 22 to 23, 28 to 30, and 36 to 54, infra. The scFv can be connected to Fab1, for example, by a peptide linker. Linkers that can be used to connect the scFv to Fab1 are described in Section 6.2.3 and specific embodiments 13 to 18, infra. Fc domains that can be used in the MBMs of the disclosure are described in Section 6.2.4 and specific embodiments 24 to 26, infra.

The present disclosure further provides drug conjugates comprising the MBMs of the disclosure (referred to herein as "antibody-drug conjugates" or "ADCs" for convenience). Exemplary features of ADCs are described in Section 6.3 and specific embodiment 61, infra.

The disclosure further provides nucleic acids encoding the MBMs of the disclosure. The nucleic acids encoding the MBMs can be a single nucleic acid (e.g., a vector encoding all polypeptide chains of a MBM) or a plurality of nucleic acids (e.g., two or more vectors encoding the different polypeptide chains of a MBM). The disclosure further provides host cells and cell lines engineered to express the nucleic acids and MBMs of the disclosure. The disclosure further provides methods of producing an MBM of the disclosure. Exemplary nucleic acids, host cells, cell lines, and methods of producing a MBM are described in Section 6.5 and specific embodiments 78 to 83, infra.

The disclosure further provides pharmaceutical compositions comprising the MBMs and ADCs of the disclosure. Exemplary pharmaceutical compositions are described in Section 6.6 and specific embodiment 62, infra.

Further provided herein are methods of using the MBMs, the ADCs, and the pharmaceutical compositions of the disclosure, e.g., for treating cancer. Exemplary methods are described in Section 6.7 and specific embodiments 63 to 77, infra.

5. BRIEF DESCRIPTION OF THE FIGURES

FIG. 1: Schematic representation of an exemplary MBM of the disclosure.

FIGS. 2A-2E: Schematic representation of exemplary MBM of the disclosure in which the Fabs contain modifications to promote appropriate VH and VL pairings. Additional strategies are set forth in Section 6.2.2 below.

Figure 3D:
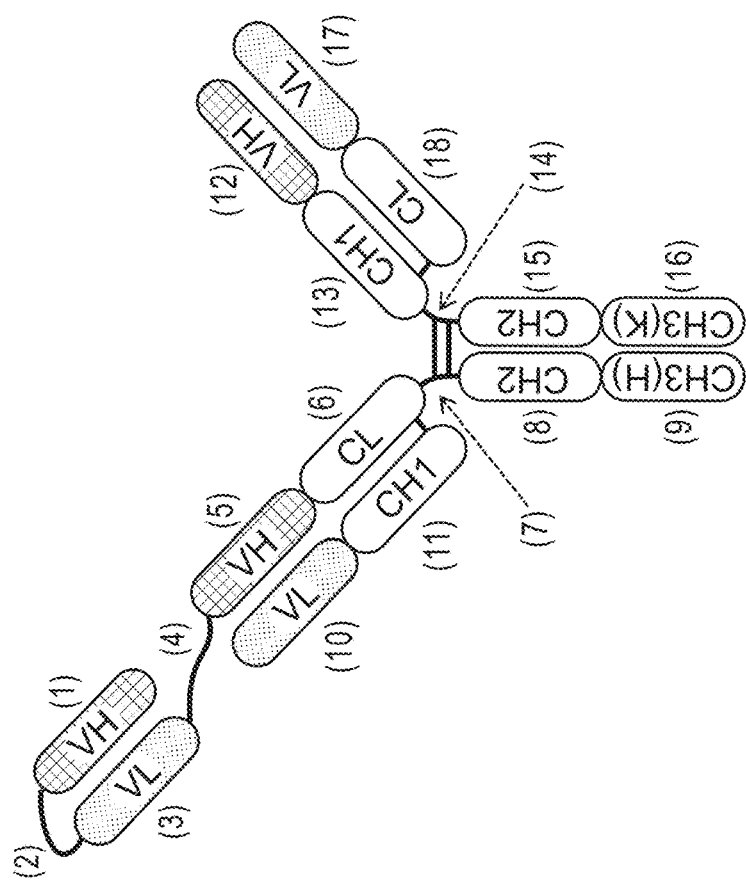

FIGS. 3A-3D: Schematic representation of exemplary MBMs of the disclosure in which the Fc domains contain modifications to promote heterodimerization or purification of properly paired heterodimers. FIG. 3A and FIG. 3B depict CH3 with a star mutation (CH3 with H435R Y436F modifications) as CH3(*) and FIG. 3C and FIG. 3D depict knob and hole mutations with (K) and (H) designations, respectively. Elsewhere in the drawings, star mutations are depicted with an asterisk (*) and knob-in-hole mutations are depicted with a triangle (e.g., ▶ or ◀). These two strategies (e.g., star mutations and knob-in-hole mutations) can be combined in a single MBM. Additional heterodimerization strategies are set forth in Section 6.2.4 below.

FIGS. 4A1-4B2: Expression profiles of an exemplary target molecule pair specifically bound by an MBM of the disclosure: KLB and FGFR1c, according to the Genotype-Tissue Expression (GTEx) project (FIG. 4A1-FIG. 4A2) and the Human Protein Atlas (FIG. 4B1-FIG. 4B2). The tissues in which there is overlapping expression are shown in bold font.

Figure 5:
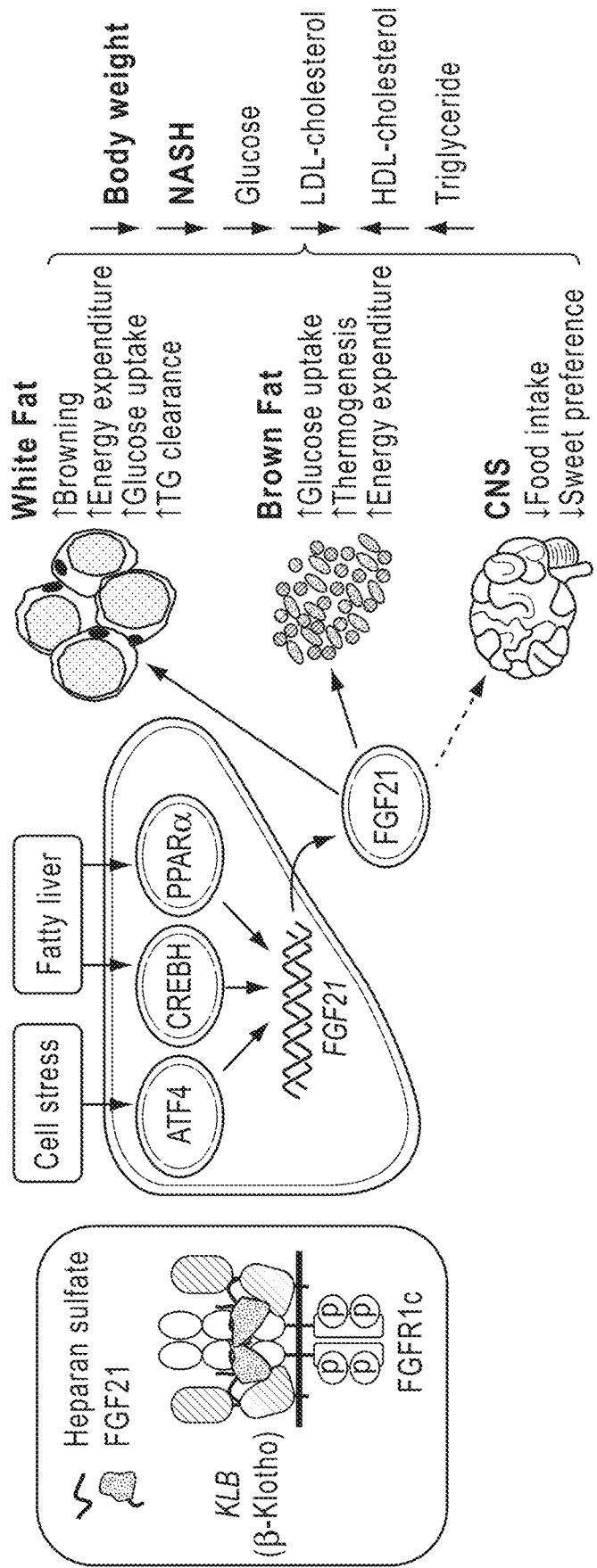

FIG. 5: Metabolic pathways modulated by FGF21 signaling.

Figure 6A:
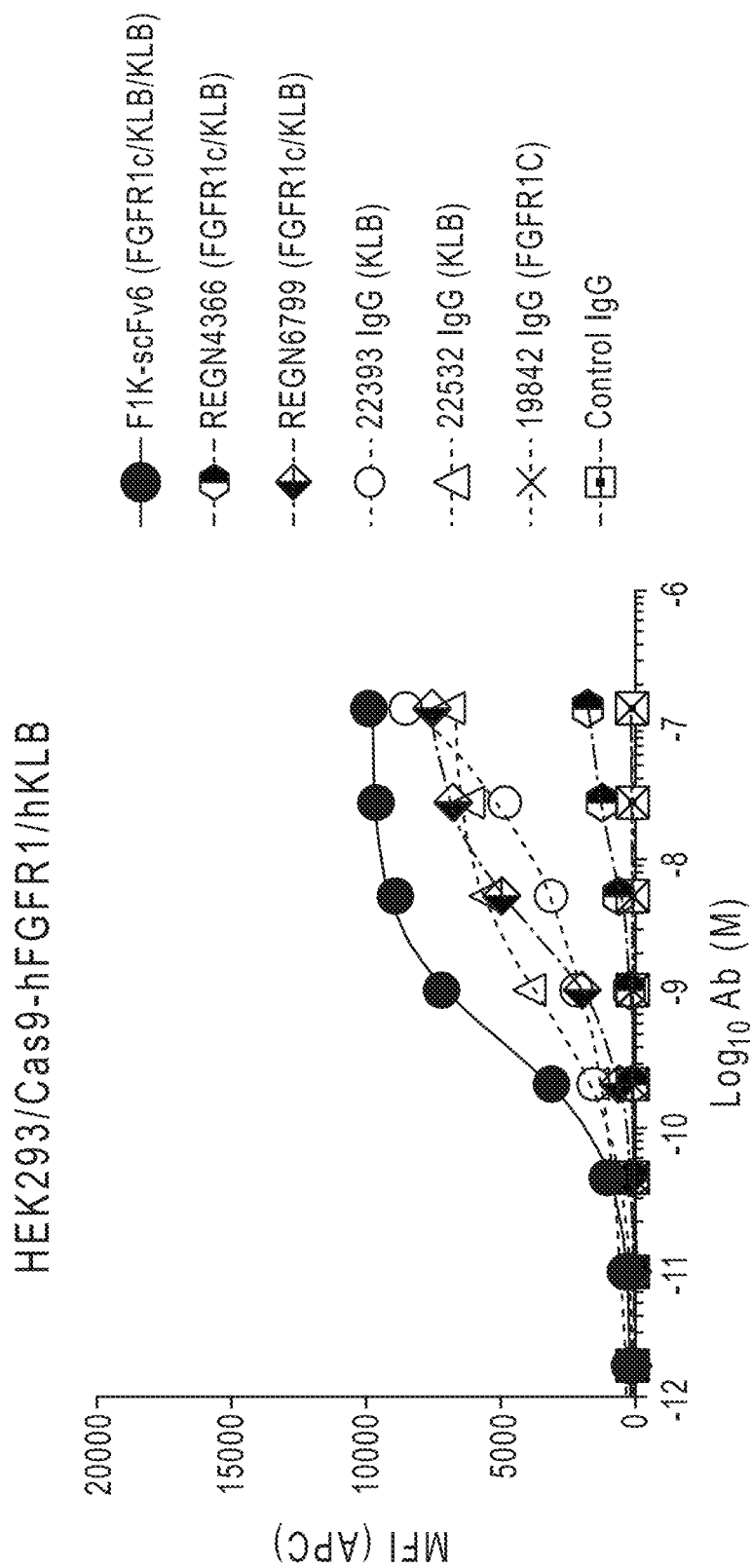
Figure 6B:
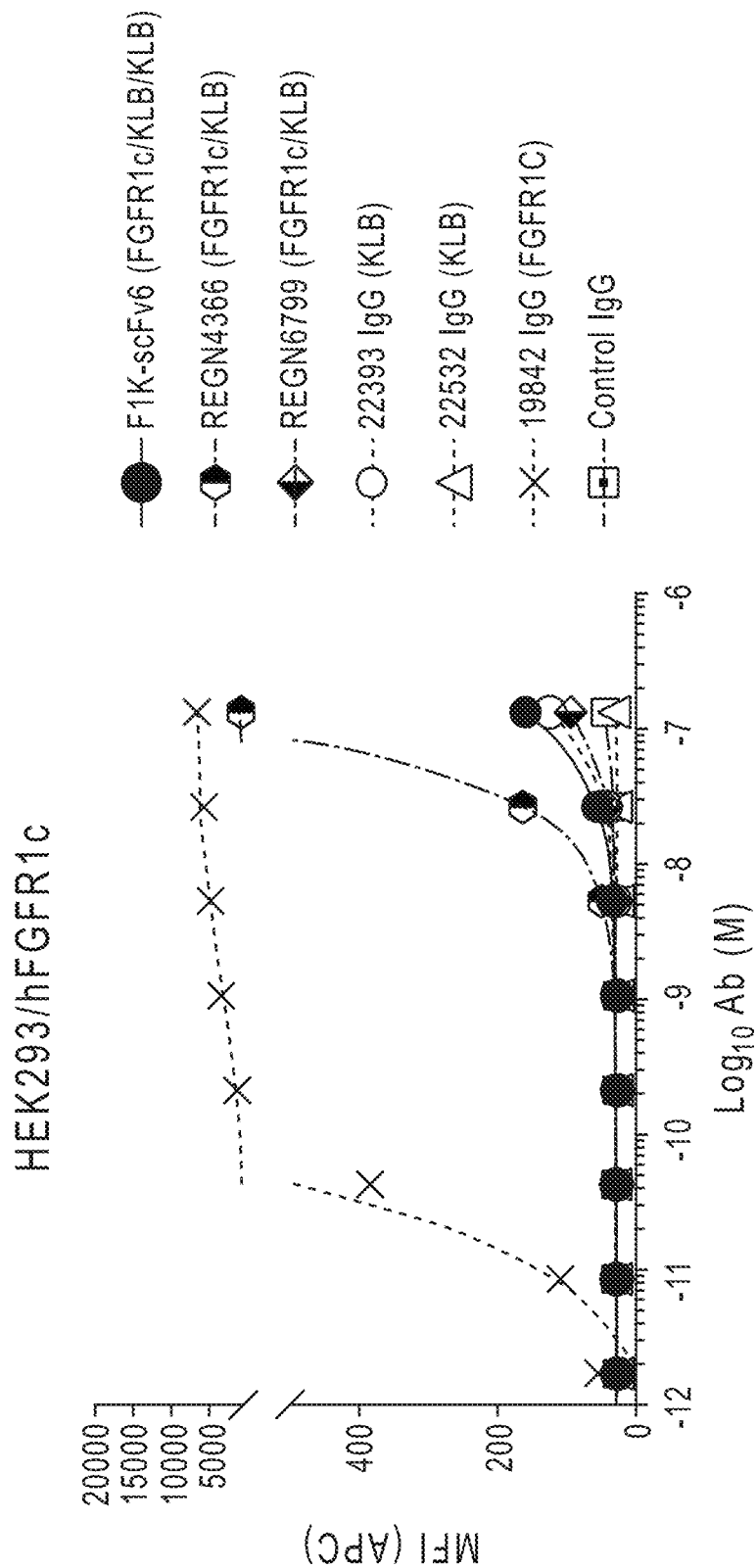
Figure 6C:
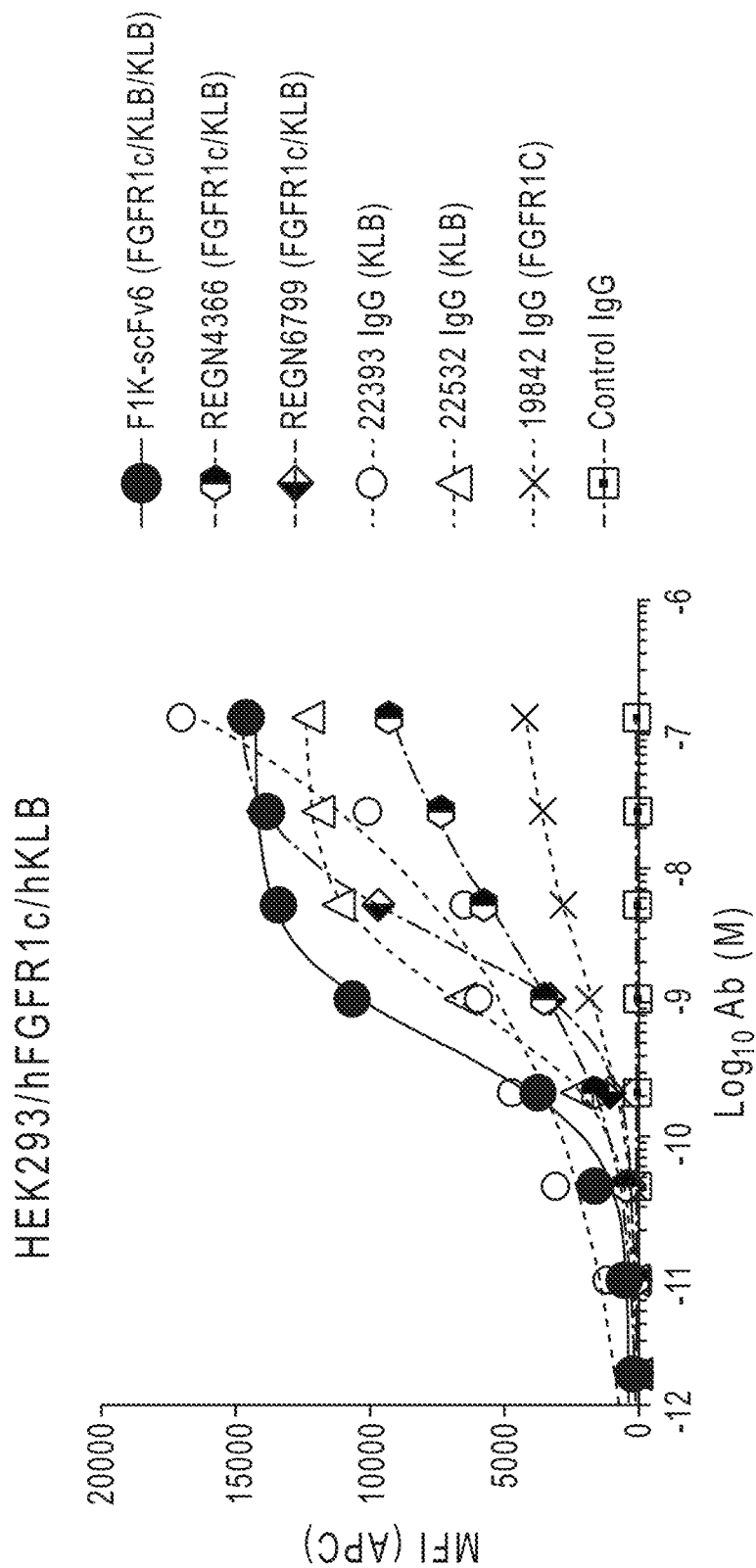

FIGS. 6A-6C: FACS binding assay results (Example 1). FIG. 6A: HEK293/Cas90hFGFR1/hKLB cells; FIG. 6B: HEK293/hFGFR1c cells; FIG. 6C: HEK293/hFGFR1c/hKLB cells. MFI: Mean Fluorescence Intensity; APC: Allophycocyanin.

Figure 7:
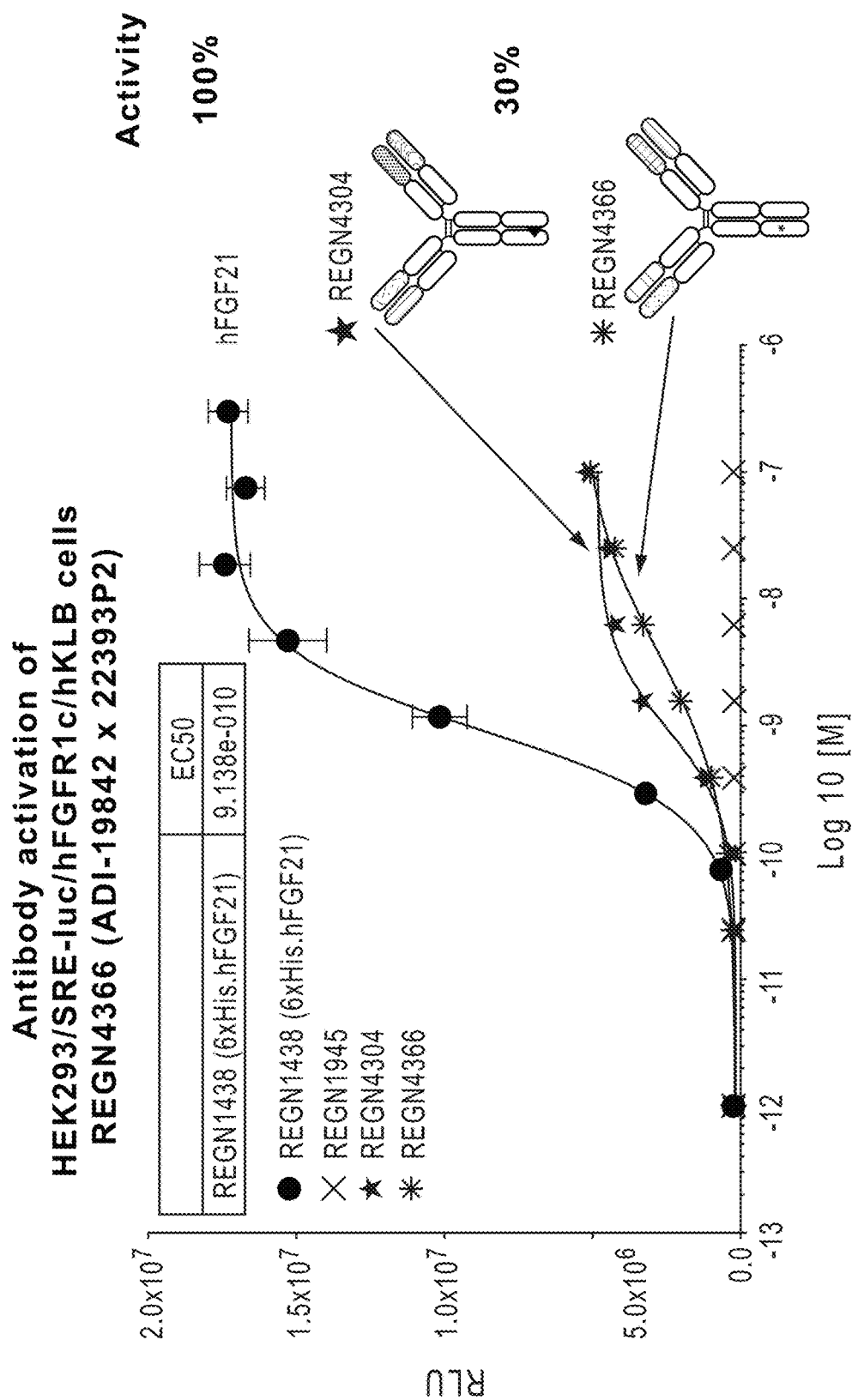

FIG. 7: Graph illustrating the modest activation by bispecific binding molecules (BBMs) REGN4366, an FGFR1c×KLB bispecific control and a comparator FGFR1c×KLB bispecific REGN4304 in HEK293/SRE-luc/hFGFR1c/hKLB cells as compared to FGFR21.

Figure 8:
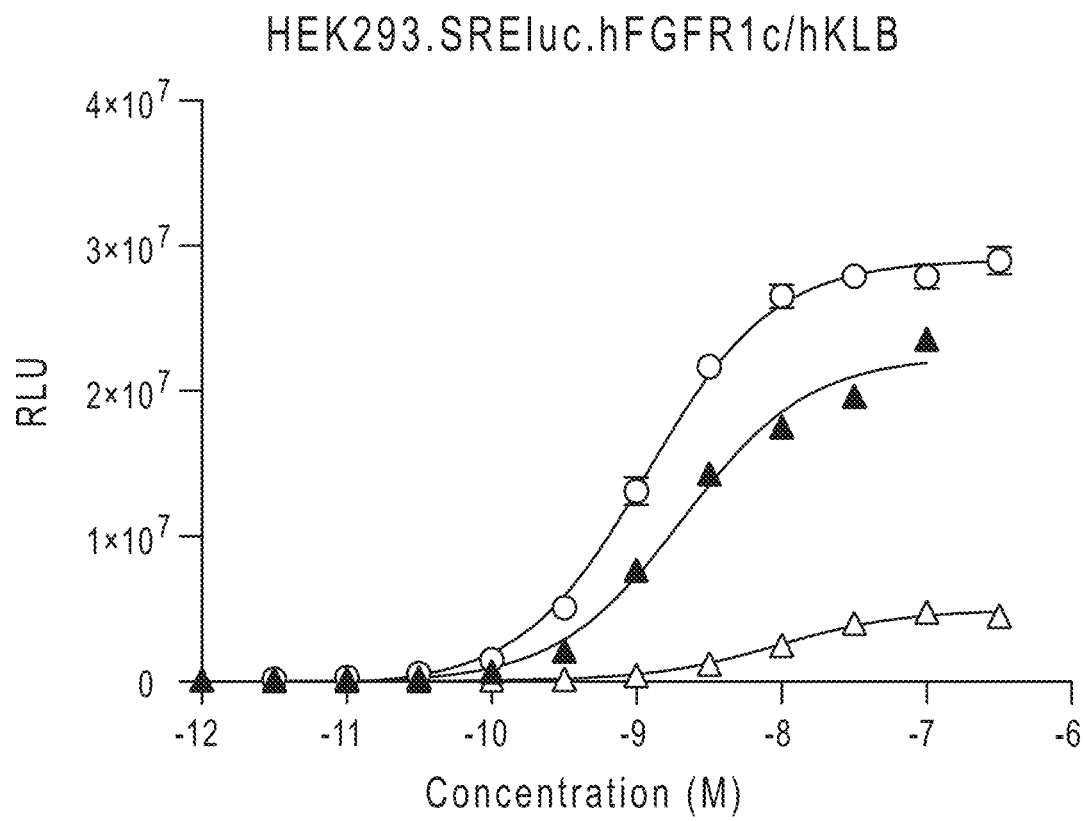

FIG. 8: Enhanced reporter activation in HEK293.SREluc.hFGFR1cHS/hKLB cells by trivalent F1K-scFv6 in comparison to bivalent REGN4366 (RLU: relative light unit) (Example 1).

FIG. 9: Graph showing the results of the study evaluating six linker length variants of the molecule designated scFv6 (containing the KLB binder designated 22393 or 393 at the (1) position, the FGFR1 binder designated ADI-19842 or 842 at the (2) position, and the KLB binder designated 22532 or 532, which does not block the binding of the KLB binder 22393 in the scFv format at the (3) position). The molecules contained linkers from 7 to 45 amino acids between the FGFR1 binding domain and the N-terminal 532 scFv domain compared. Trispecific binding molecules of all linker lengths exhibit greater activity than REGN4304, a comparator bispecific binding molecule.

Figure 10A:
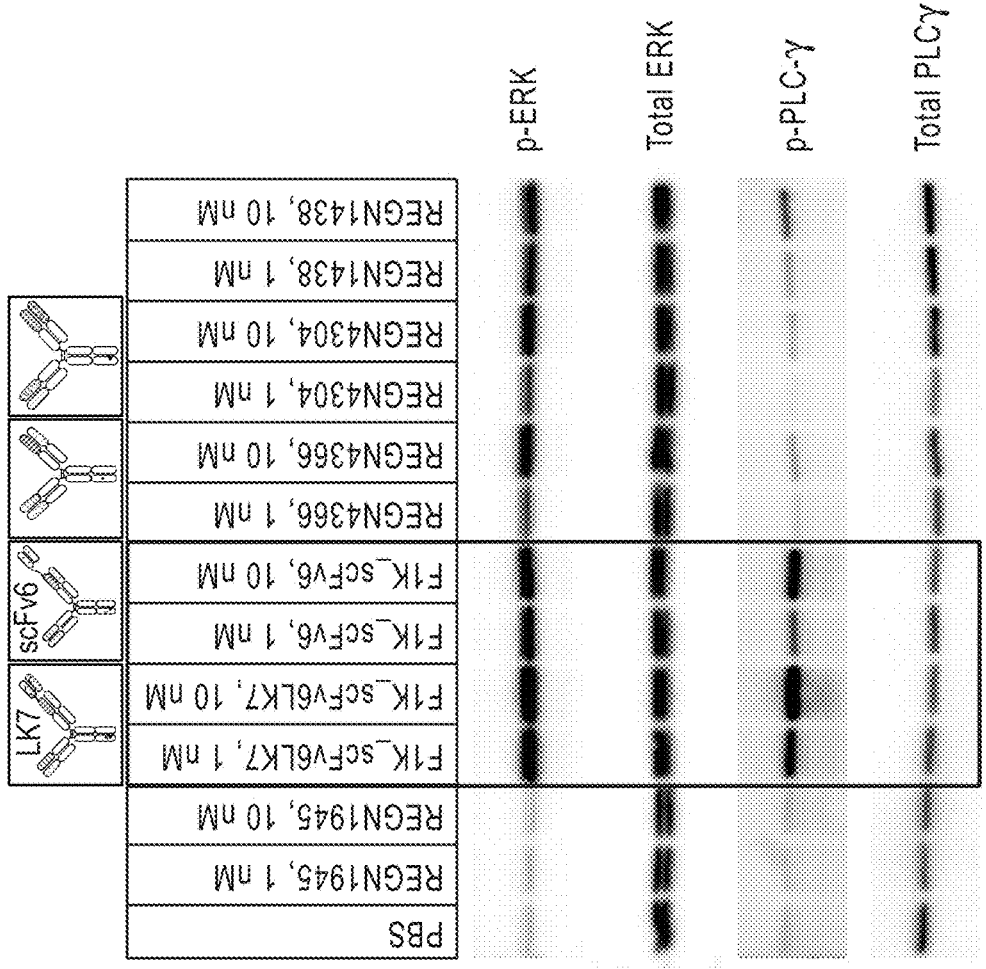
Figure 10B:
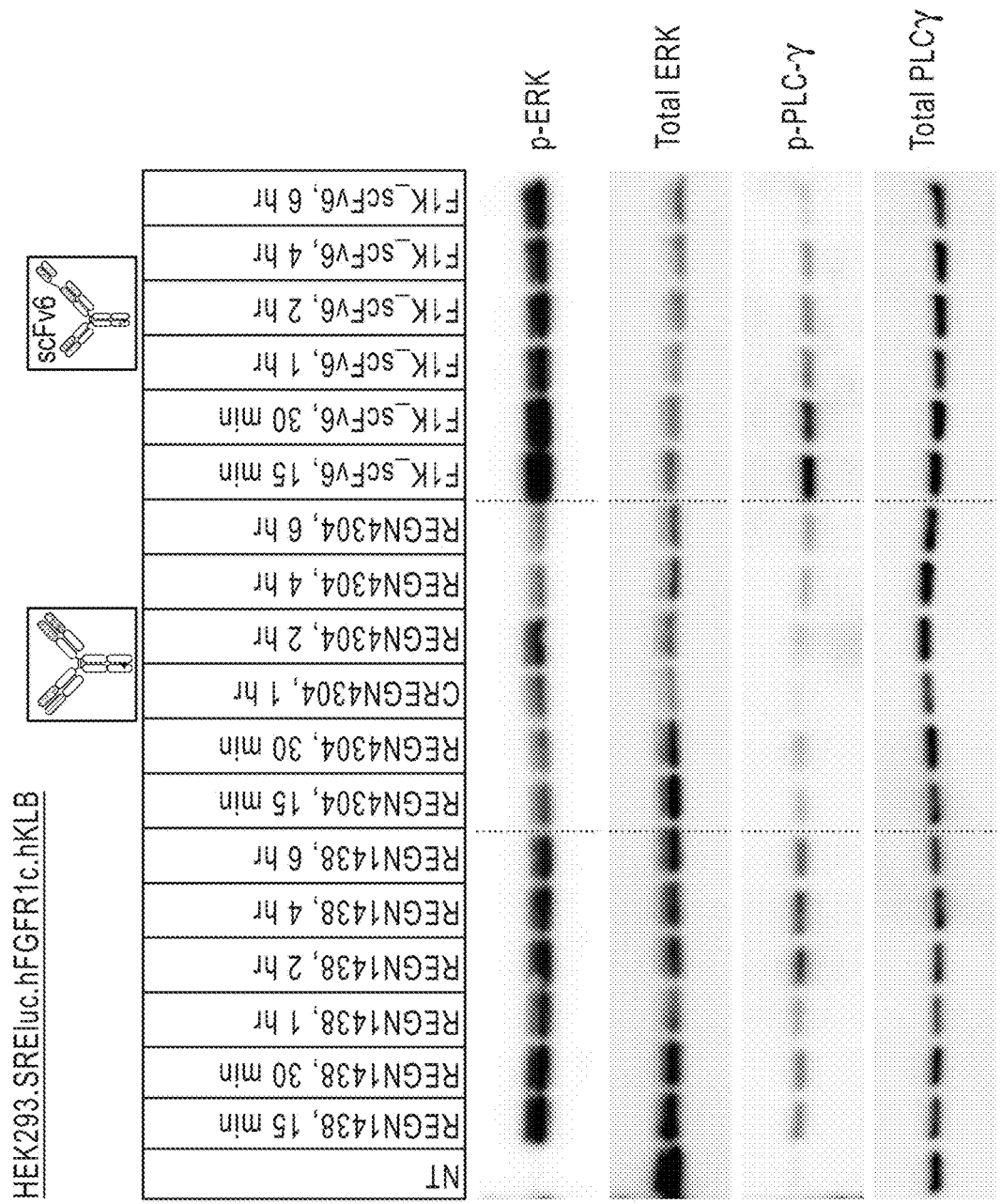

FIGS. 10A-10B: Figures demonstrate that the trispecific binders designated F1K_scFv6 and scFv6 LK7 (containing a 7 amino-acid linker) strongly activate FGFR1c signaling in HEK293 cells stably expressing hFGFR1c and hKLB. FIG. 10A: Western blot illustrating drug concentration-dependent FGFR1c signaling through ERK and PLCγ phosphorylation as a result of serum starvation for 16 hrs followed by drug treatment for 15 min at concentrations of 1 nM and 10 nM. FIG. 10B: Western blot illustrating time-dependent FGFR1c signaling through ERK and PLCγ phosphorylation as a result of serum starvation for 16 hrs followed by drug treatment at a concentration of 10 nM for 15, 30 min and 1, 2, 4 and 6-hr incubation periods.

Figure 11A:
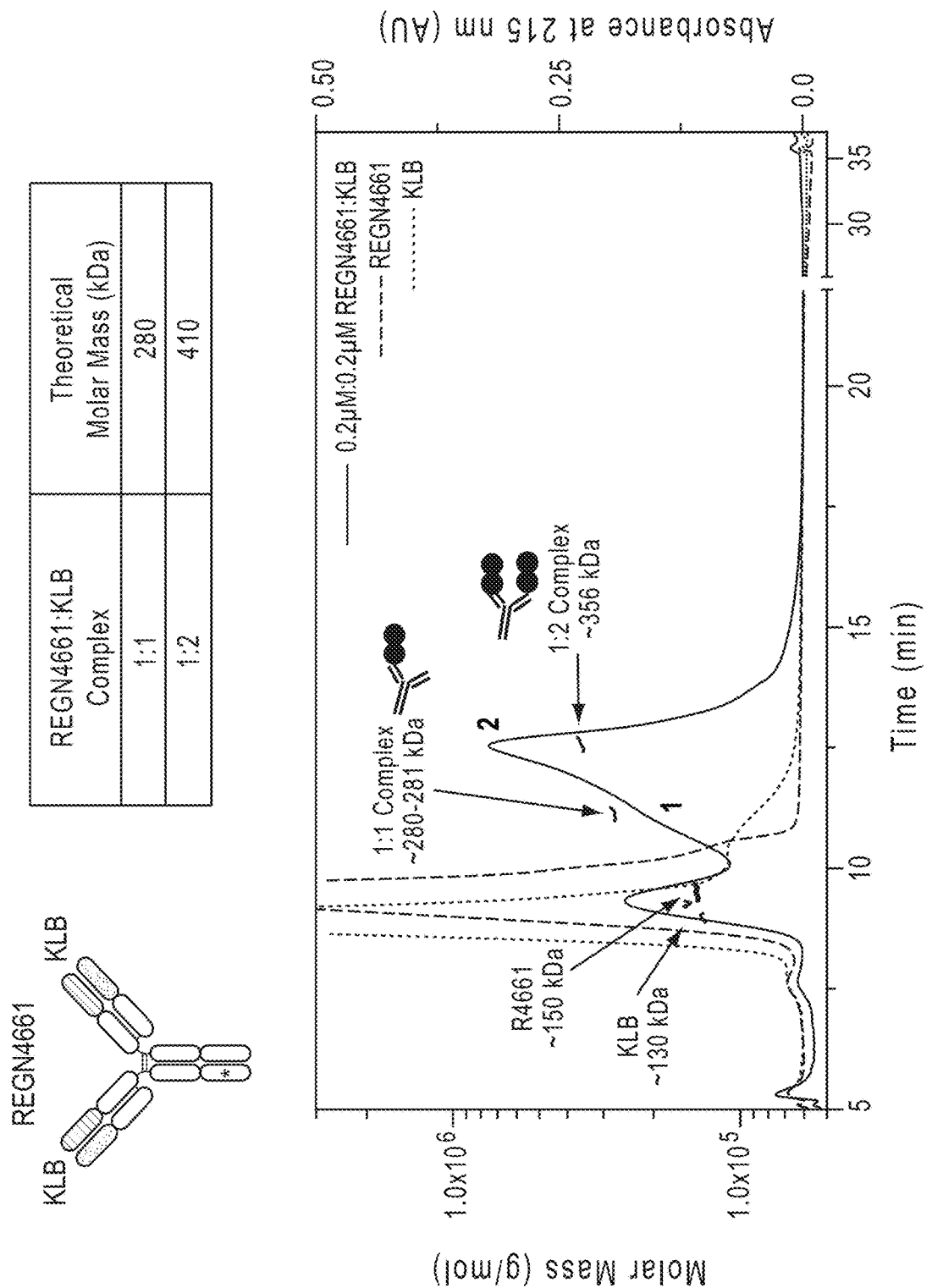
Figure 11B:
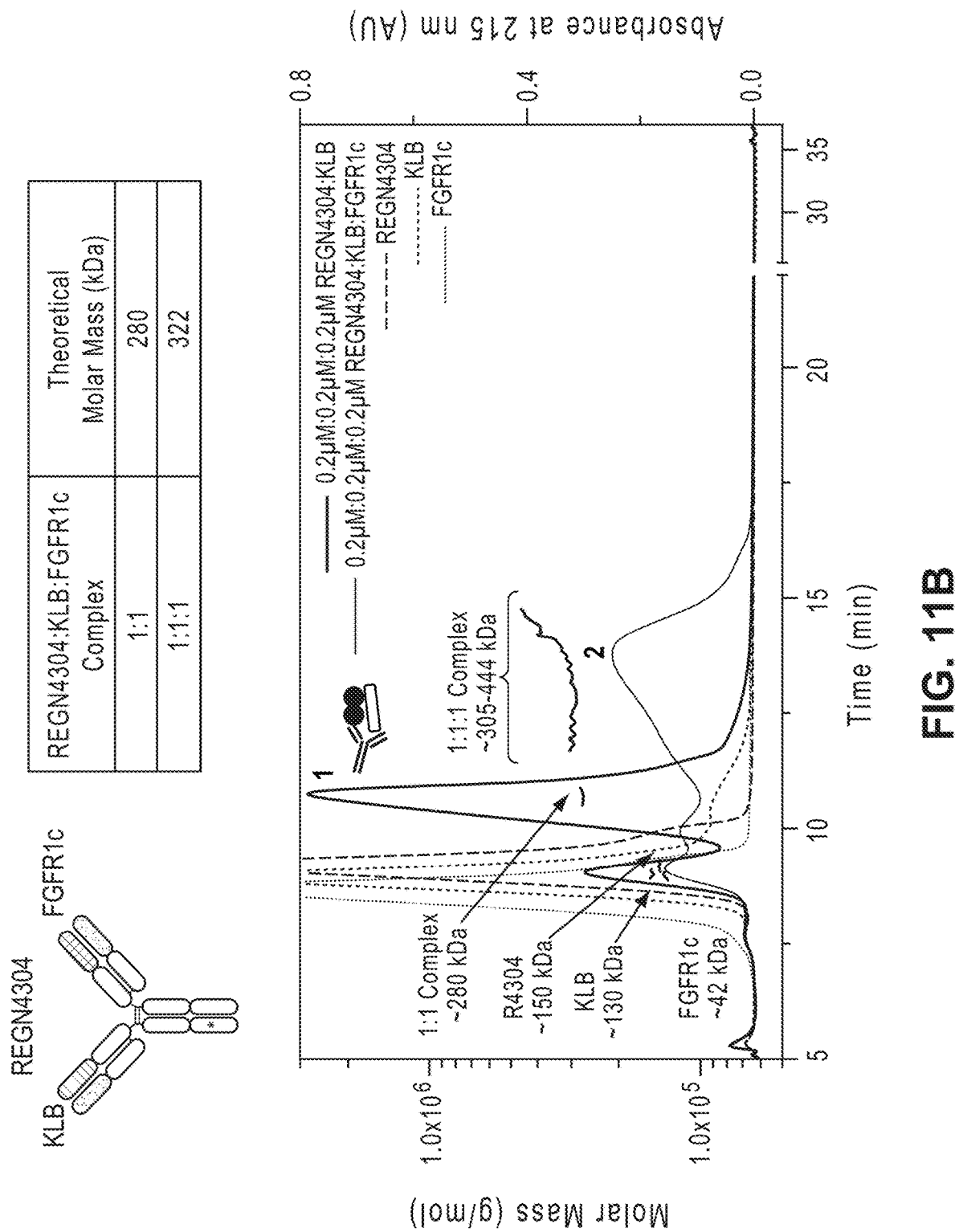
Figure 11C:
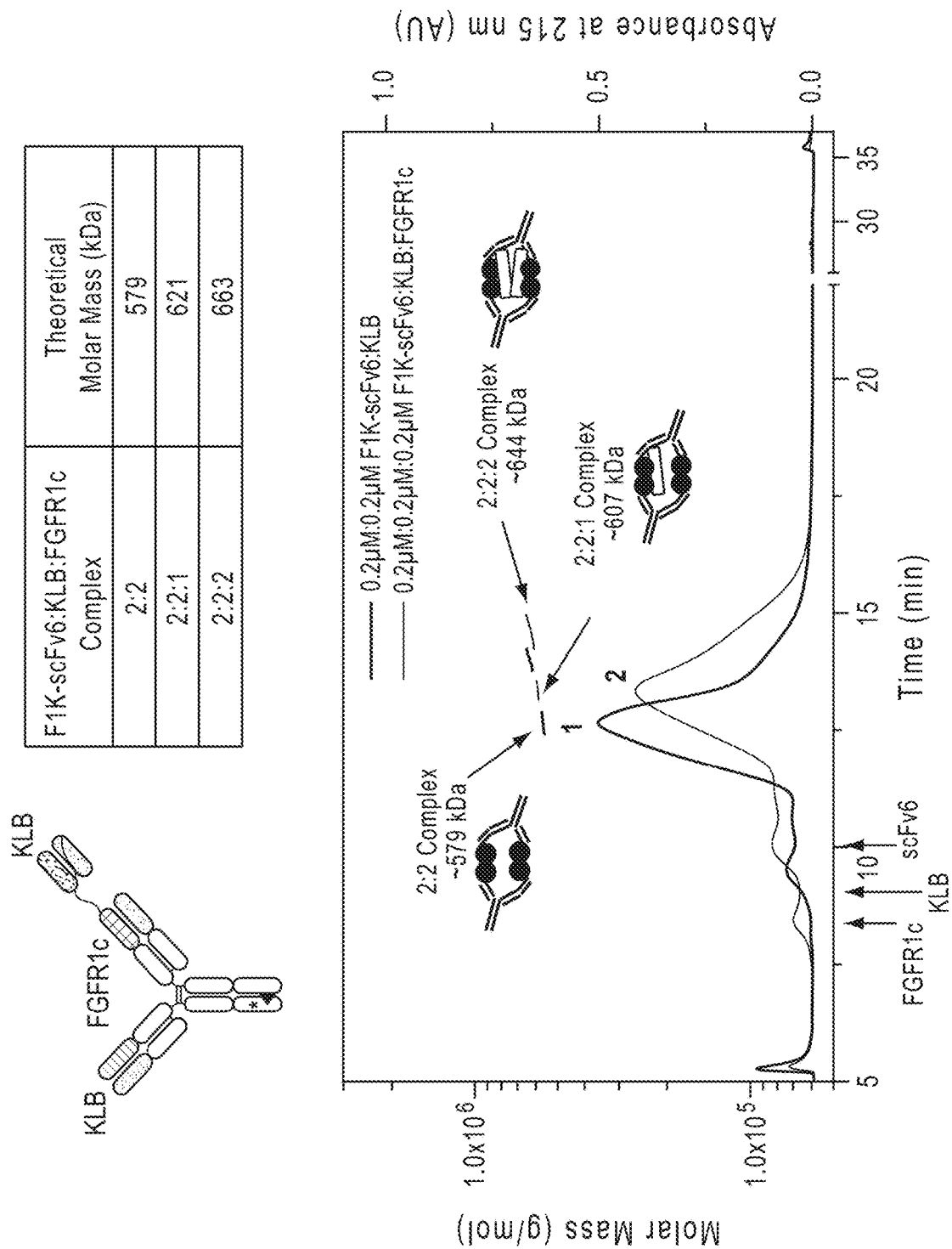

FIGS. 11A-11C: Monospecific (anti-KLB; REGN4661) and bispecific binding molecules (anti-KLBxFGFR1c; REGN4304) bind KLB (tandem filled circles)/FGFR1c (open rectangles) with different stoichiometries compared to trispecific mAbs (F1K.scFv6 IgG1 and F1K-Fab6 IgG1). FIG. 11A: REGN4661:KLB complexes (solid line) were analyzed by asymmetric flow field-flow fractionation coupled to multi-angle light scattering (A4F-MALS). Fractograms from individual samples of REGN4661 (dashed line) and KLB (dotted line) are also overlaid. Relative UV absorbance at 215 nm as a function of retention time is shown for each sample and the measured molar masses of resolved peaks are indicated. FIG. 11B: REGN4304:KLB complexes (thick solid line) and REGN4304:KLB:FGFR1c complexes (thin solid line) were analyzed by asymmetric flow field-flow fractionation coupled to multi-angle light scattering (A4F-MALS). Fractograms from individual samples of REGN4304 (dashed line), KLB (dotted line) and FGFR1c (grey dotted line) are also overlaid. Relative UV absorbance at 215 nm as a function of retention time is shown for each sample and the measured molar masses of resolved peaks are indicated. FIG. 11C: F1K-scFv6 IgG1: KLB complexes (thick solid line) and F1K-scFv6 IgG1: KLB:FGFR1c complexes (0.2 µM:0.2 µM:0.2 µM, thin solid line) were analyzed by asymmetric flow field-flow fractionation coupled to multi-angle light scattering (A4F-MALS). Relative UV absorbance at 215 nm as a function of retention time is shown for each sample and the measured molar masses of resolved peaks are indicated.

Figure 12A:
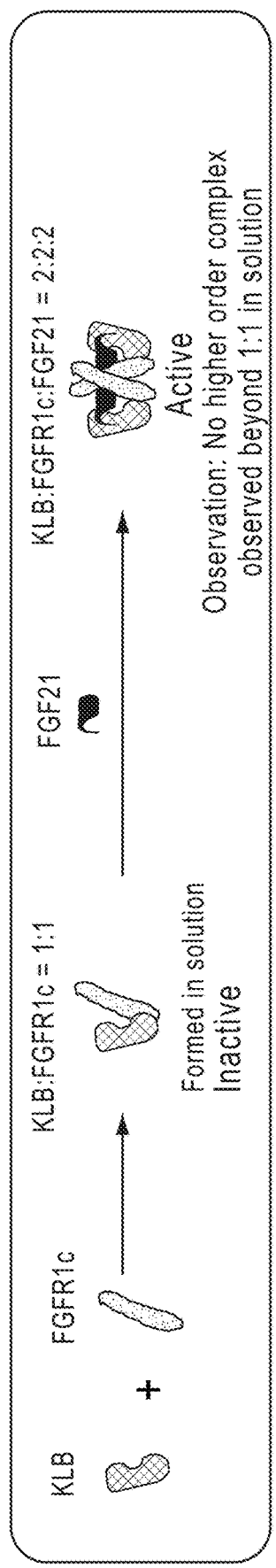
Figure 12B:
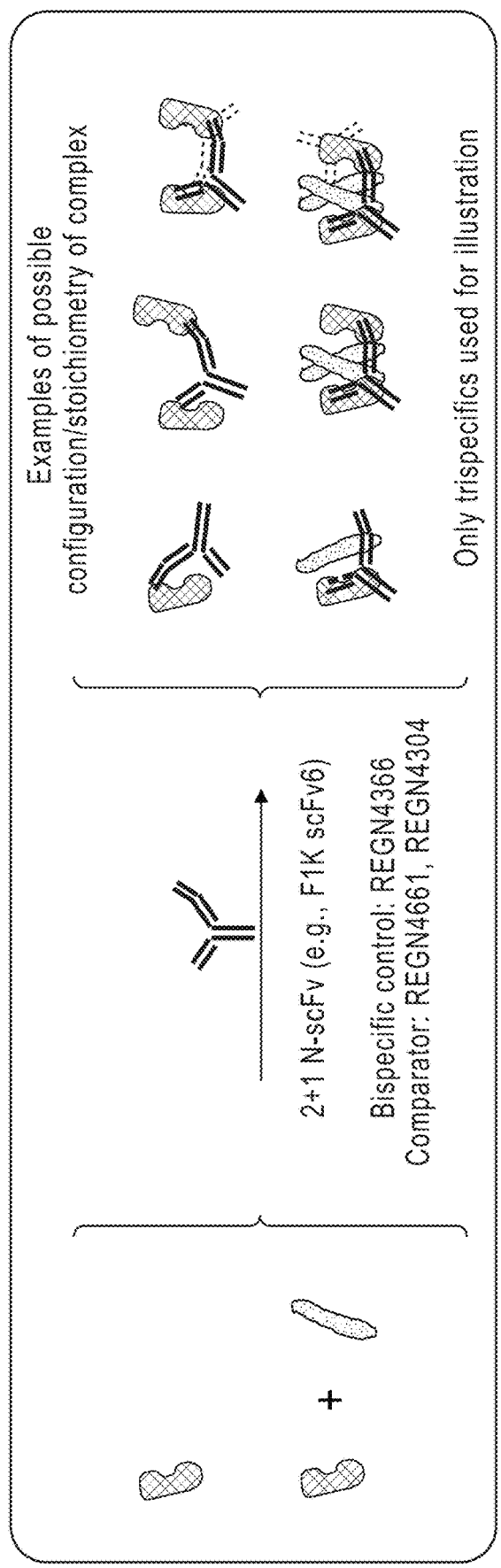

FIGS. 12A-12B: Schematic representation of how clusters of FGFR1c, KLB and FGF21 form active complexes (FIG. 12A) and the potential stoichiometric complexes formed between FGFR1c and KLB receptors and the 2+1 N-scFv trispecific binding molecules, e.g., F1K-scFv6, compared to bispecific binding molecules and monospecific controls (FIG. 12B).

Figure 13A:
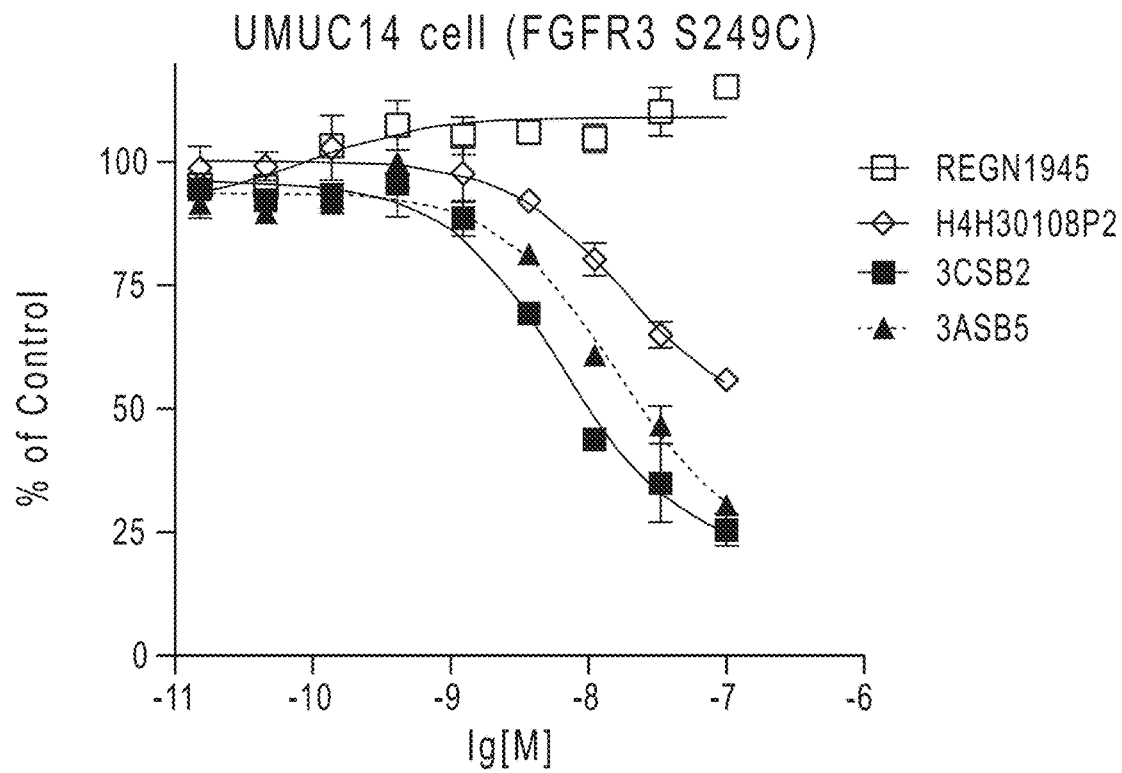
Figure 13B:
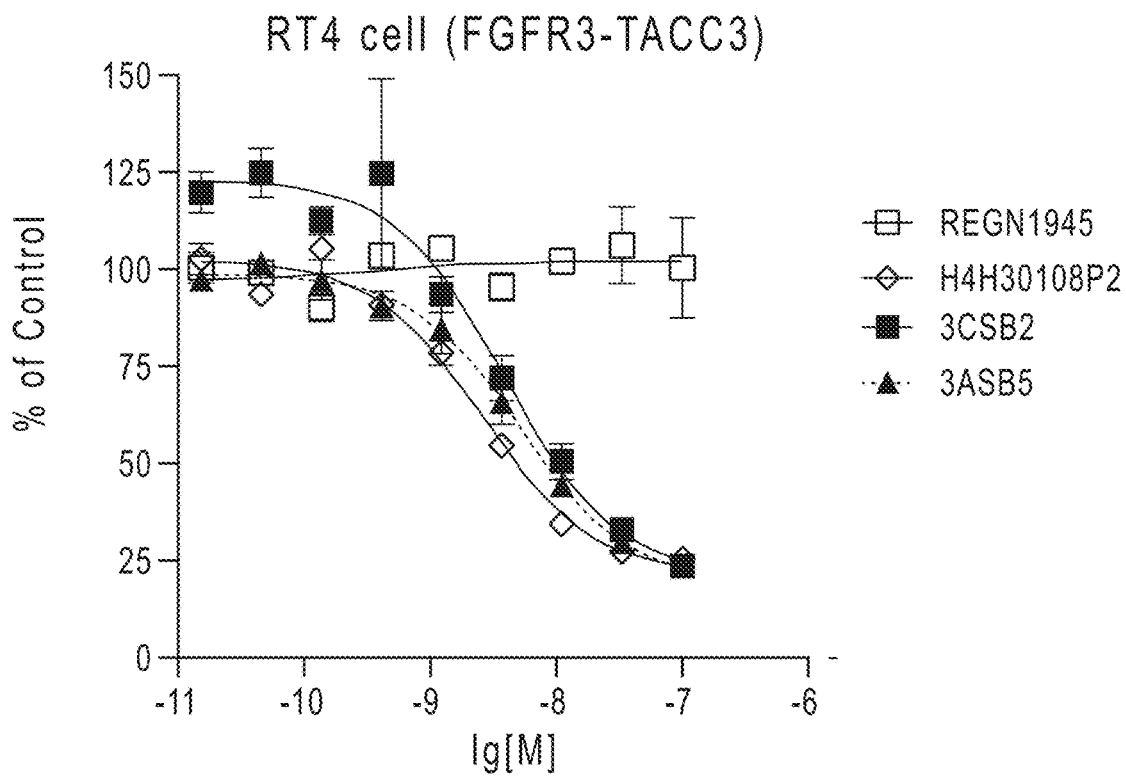

FIGS. 13A-13B: Proliferation assay with UMUC14 cells expressing FGFR3 S249C mutation (FIG. 13A) or FGFR3-TACC3 fusion mutation (FIG. 13B).

Figure 14:
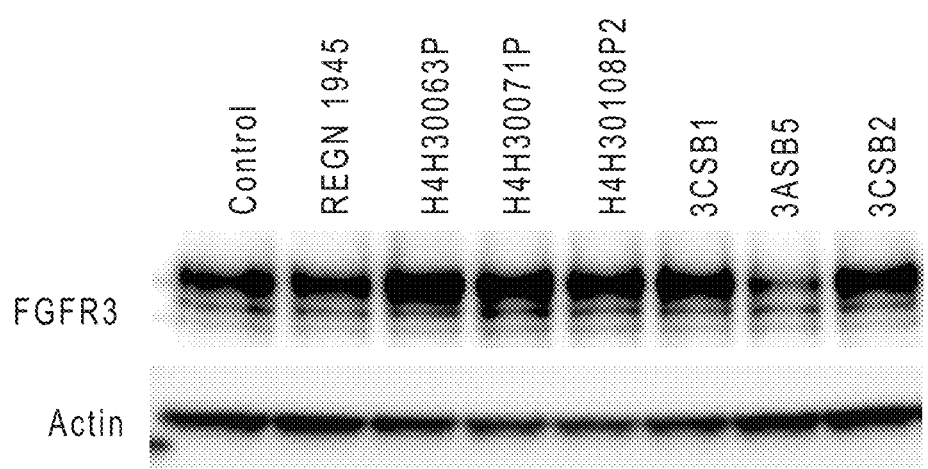

FIG. 14: Results of FGFR3 receptor degradation assay in UMUC14 cells.

6. DETAILED DESCRIPTION

6.1. Definitions

As used herein, the following terms are intended to have the following meanings:

Antigen Binding Site or ABS: The term "antigen binding site" or "ABS" as used herein refers to the portion of a MBM that is capable of specific, non-covalent, and reversible binding to a target molecule. The MBMs of the disclosure comprise a first ABS ("ABS1") which is part of an scFv, a second ABS ("ABS2") which is part of a Fab, and a third ABS ("ABS3") which is part of a Fab.

Associated: The term "associated" in the context of an MBM refers to a functional relationship between two or more polypeptide chains. In particular, the term "associated" means that two or more polypeptides are associated with one another, e.g., non-covalently through molecular interactions or covalently through one or more disulfide bridges or chemical cross-linkages, so as to produce a functional MBM in which ABS1, ABS2 and ABS3 can bind their respective targets. Examples of associations that might be present in an MBM of the disclosure include (but are not limited to) associations between homodimeric or heterodimeric Fc domains in an Fc region, associations between VH and VL regions in a Fab or scFv, associations between CH1 and CL in a Fab, and associations between CH3 and CH3 in a domain substituted Fab.

Complementarity Determining Reaction or CDR: The terms "complementarity determining region" or "CDR," as used herein, refer to the sequences of amino acids within antibody variable regions which confer antigen specificity and binding affinity. In general, there are three CDRs in each heavy chain variable region (CDR-H1, CDR-H2, HCDR-H3) and three CDRs in each light chain variable region (CDR1-L1, CDR-L2, CDR-L3). Exemplary conventions that can be used to identify the boundaries of CDRs include, e.g., the Kabat definition, the Chothia definition, the ABS definition and the IMGT definition. See, e.g., Kabat, 1991, "Sequences of Proteins of Immunological Interest," National Institutes of Health, Bethesda, Md. (Kabat numbering scheme); Al-Lazikani et al., 1997, J. Mol. Biol. 273:927-948 (Chothia numbering scheme); Martin et al., 1989, Proc. Natl. Acad. Sci. USA 86:9268-9272 (ABS numbering scheme); and Lefranc et al., 2003, Dev. Comp. Immunol. 27:55-77 (IMGT numbering scheme). Public databases are also available for identifying CDR sequences within an antibody.

Derived from: As used herein, the term "derived from" indicates a relationship between a first and a second molecule. It generally refers to structural similarity between the first molecule and a second molecule and does not connote or include a process or source limitation on a first molecule that is derived from a second molecule.

EC50: The term "EC50" refers to the half maximal effective concentration of an antibody or MBM which induces a response halfway between the baseline and maximum after a specified exposure time. The EC50 essentially represents the concentration of an antibody or MBM where 50% of its maximal effect is observed. In certain embodiments, the EC50 value equals the concentration of an antibody or MBM that gives half-maximal binding to cells expressing the target molecules that can be specifically bound by an antibody or MBM, e.g., as determined by FACS binding assay. Thus, reduced or weaker binding is observed with an increased EC50, or half maximal effective concentration value. EC50 values of MBMs of the disclosure can in some embodiments be characterized by EC50 values of about $10^{-5}$M or less (e.g., less than $10^{-5}$M, less than $10^{-6}$M, less than $10^{-7}$M, less than $10^{-8}$M, or less than $10^{-9}$M).

Epitope: An epitope, or antigenic determinant, is a portion of an antigen (e.g., target molecule) recognized by an antibody or other antigen-binding moiety as described herein. An epitope can be linear or conformational.

Fab: The term "Fab" in the context of an MBM of the disclosure refers to a pair of polypeptide chains, the first comprising a variable heavy (VH) domain of an antibody N-terminal to a first constant domain (referred to herein as C1), and the second comprising variable light (VL) domain of an antibody N-terminal to a second constant domain (referred to herein as C2) capable of pairing with the first constant domain. In a native antibody, the VH is N-terminal to the first constant domain (CH1) of the heavy chain and the VL is N-terminal to the constant domain of the light chain (CL). The Fabs of the disclosure can be arranged according to the native orientation or include domain substitutions or swaps on that facilitate correct VH and VL pairings, particularly where the MBMs of the disclosure comprise non-identical Fabs. For example, it is possible to replace the CH1 and CL domain pair in a Fab with a CH3-domain pair to facilitate correct modified Fab-chain pairing in heterodimeric MBMs. It is also possible to reverse CH1 and CL, so that the CH1 is attached to VL and CL is attached to the VH, a configuration generally known as Crossmab. Alternatively, or in addition to, the use of substituted or swapped constant domains, correct chain pairing can be achieved by the use of universal light chains that can pair with both variable regions of a heterodimeric MBM of the disclosure.

Fc Domain and Fc Region: The term "Fc domain" refers to a portion of the heavy chain that pairs with the corresponding portion of another heavy chain. The term "Fc region" refers to the region of antibody-based binding molecules formed by association of two heavy chain Fc domains. The two Fc domains within the Fc region may be the same or different from one another. In a native antibody the Fc domains are typically identical, but for the purpose of producing the MBMs of the disclosure, one or both Fc domains might advantageously be modified to allow for heterodimerization.

Half Antibody: The term "half antibody" refers to a molecule that comprises at least one ABS or ABS chain (e.g., one chain of a Fab) and can associate with another molecule comprising an ABS or ABS chain through, e.g., a disulfide bridge or molecular interactions (e.g., knob-in-hole interactions between Fc heterodimers). A half antibody can be composed of one polypeptide chain or more than one polypeptide chains (e.g., the two polypeptide chains of a Fab). In a preferred embodiment, a half-antibody comprises an Fc domain.

Host cell: The term "host cell" as used herein refers to cells into which a nucleic acid of the disclosure has been introduced. The terms "host cell" and "recombinant host cell" are used interchangeably herein. It is understood that such terms refer to the particular subject cell and to the progeny or potential progeny of such a cell. Because certain modifications may occur in succeeding generations due to either mutation or environmental influences, such progeny may not, in fact, be identical to the parent cell, but are still included within the scope of the term as used herein. Typical host cells are eukaryotic host cells, such as mammalian host cells. Exemplary eukaryotic host cells include yeast and mammalian cells, for example vertebrate cells such as a mouse, rat, monkey or human cell line, for example HKB11 cells, PER.C6 cells, HEK cells or CHO cells.

Multispecific Binding Molecule or MBM: The term "multispecific binding molecule" or "MBM" as used herein refers to molecules (e.g., assemblies of multiple polypeptide chains) comprising two half antibodies and which specifically bind to at least two different epitopes (and in some instances three or more different epitopes) and comprise an ABS1, and ABS2, and an ABS3.

Operably linked: The term "operably linked" as used herein refers to a functional relationship between two or more regions of a polypeptide chain in which the two or more regions are linked so as to produce a functional polypeptide.

Parental Antibody: The term "parental antibody" means an antibody from which a MBM of the disclosure is derived (as that term is defined herein), e.g., a parental monospecific or bispecific antibody lacking an N-terminal scFv domain present in the MBM of the disclosure. An MBM of the disclosure, e.g., in one or more of its ABSs, might share binding sequences, e.g., CDR, VH and/or VL sequences, with the "parental" antibody, but does not have to be prepared by modifying the parental antibody or its coding sequence.

Simile Chain Fv or scFv: The term "single chain Fv" or "scFv" as used herein refers to a polypeptide chain comprising the VH and VL domains of antibody, where these domains are present in a single polypeptide chain.

Specifically (or selectively) binds: The term "specifically (or selectively) binds" as used herein means that a MBM or antigen binding site ("ABS") thereof forms a complex with a target molecule that is relatively stable under physiologic conditions. Specific binding can be characterized by a KD of about $5\times10^{-2}$M or less (e.g., less than $5\times10^{-2}$M, less than $10^{-2}$M, less than $5\times10^{-3}$M, less than $10^{-3}$M, less than $5\times10^{-4}$M, less than $10^{-4}$M, less than $5\times10^{-5}$M, less than $10^{-5}$M, less than $5\times10^{-6}$M, less than $10^{-6}$M, less than $5\times10^{-7}$M, less than $10^{-7}$M, less than $5\times10^{-8}$M, less than $10^{-8}$M, less than $5\times10^{-9}$M, less than $10^{-9}$M, or less than $10^{-10}$M). Methods for determining the binding affinity of an antibody or an antibody fragment, e.g., an MBM or ABS, to a target molecule are well known in the art and include, for example, equilibrium dialysis, surface plasmon resonance (e.g., Biacore assays), fluorescent-activated cell sorting (FACS) binding assays and the like. A MBM or ABS thereof that specifically binds a target molecule from one species can, however, have cross-reactivity to the target molecule from one or more other species.

Target Molecule: The term "target molecule" as used herein refers to any biological molecule (e.g., protein, carbohydrate, lipid or combination thereof) expressed on a cell surface that can be specifically bound by an antigen binding site of a MBM.

Tissue: The term "tissue" as used herein refers a collection or aggregate of cells of a particular kind. A tissue can be derived from mesoderm (e.g., bone, muscle, connective tissue, kidneys, and related structures), endoderm (e.g., lungs, other respiratory structures, and digestive organs) or ectoderm (e.g., the nervous system, sensory organs, skin, and related structures). Examples of tissues useful for targeting by the MBMs of the disclosure include, but are not limited to, connective tissues (including fibrous connective tissues, skeletal connective tissues, and fluid connective tissues, blood, bone, tendon, ligament, adipose and areolar tissues, etc.), muscle tissues (including visceral or smooth muscle, skeletal muscle, and cardiac muscle, etc.), nervous or neural tissues (including from the central nervous system (brain, spinal cord, etc.), the peripheral nervous system (cranial nerves, spinal nerves, motor neurons, etc.), epithelial tissues (including skin, the airways, reproductive tract, digestive tract, simple squamous epithelium, stratified squamous epithelium, simple cuboidal epithelium, transitional epithelium, pseudostratified columnar epithelium, columnar epithelium, glandular epithelium, ciliated columnar epithelium, etc.), endothelial tissues (blood vessels, lymph vessels, etc.), as well as any cell or any component thereof (e.g., the extracellular matrix). The tissues targeted by an MBM of the disclosure can be (a) solid tissues or liquid tissues (e.g., blood or individual blood cell types); (b) normal tissues or disease tissues (e.g., cancer cells); and/or (c) present in the same organ (e.g., kidney or liver) or other bodily structure (e.g., tumor) or present in different organs or other bodily structures.

Tissue expression profile: The term "tissue expression profile" as used herein in reference to a target molecule refers to the expression pattern of the target molecule in the human body, for example as defined by the Human Protein Atlas (HPA) and/or the Genotype-Tissue Expression (GTEx) project. Tissue expression profiles can be protein expression profiles and/or mRNA expression profiles.

Trivalent: The term "trivalent" as used herein refers to refers to a MBM that has three antigen binding sites. In some embodiments, two of the antigen binding sites bind to the same epitope of the same target. In other embodiments, two of the antigen binding sites specifically bind to different epitopes of the same target molecule.

Universal Light Chain: The term "universal light chain" as used herein in the context of a MBM refers to a light chain polypeptide capable of pairing with the heavy chain region of Fab1 to form Fab1 and capable of pairing with the heavy chain region of Fab2 to form Fab2. Universal light chains are also known as "common light chains."

VH: The term "VH" refers to the variable region of an immunoglobulin heavy chain of an antibody, including the heavy chain of an scFv or a Fab.

VL: The term "VL" refers to the variable region of an immunoglobulin light chain, including the light chain of an scFv or a Fab.

6.2. Multispecific Binding Molecules (MBMs)

The MBMs of the disclosure comprising two half antibodies, one of which comprises at least one antigen binding site (e.g., a Fab) and the other of which comprises at least two antigen binding sites (e.g., a Fab with an scFv operably linked to the N-terminus of its VH).

The MBMs of the disclosure specifically bind to at least two different epitopes (and in some instances three or more different epitopes). The at least two different epitopes can be on the same target molecule or different target molecules. Generally, the MBMs of the disclosure specifically bind to two or more different target molecules (sometimes referred to herein as "antigens").

6.2.1. scFv

Single chain Fv or "scFv" antibody fragments comprise the VH and VL domains of an antibody in a single polypeptide chain, are capable of being expressed as a single chain polypeptide, and retain the specificity of the intact antibodies from which they are derived. Generally, the scFv polypeptide further comprises a polypeptide linker between the VH and VL domain that enables the scFv to form the desired structure for target binding. Examples of linkers suitable for connecting the VH and VL chains of an scFV are the linkers identified in Section 6.2.3.

Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The scFv can comprise VH and VL sequences from any suitable species, such as murine, human or humanized VH and VL sequences.

To create an scFv-encoding nucleic acid, the VH and VL-encoding DNA fragments are operably linked to another fragment encoding a linker, e.g., encoding any of the linkers described in Section 6.2.3 (typically a repeat of a sequence containing the amino acids glycine and serine, such as the amino acid sequence (Gly4-Ser)$_3$ (SEQ ID NO: 1), such that the VH and VL sequences can be expressed as a contiguous single-chain protein, with the VL and VH regions joined by the flexible linker (see, e.g., Bird et al., 1988, Science 242:423-426; Huston et al., 1988, Proc. Natl. Acad. Sci. USA 85:5879-5883; McCafferty et al., 1990, Nature 348: 552-554).

6.2.2. Fab1 and Fab2

The MBMs of the disclosure comprise at least one Fab domain in each half antibody. Fab domains were traditionally produced from by proteolytic cleavage of immunoglobulin molecules using enzymes such as papain. In the MBMs of the disclosure, the Fab domains are recombinantly expressed as part of a larger molecule.

The Fab domains can comprise constant domain and variable region sequences from any suitable species, and thus can be murine, chimeric, human or humanized.

Fab domains typically comprise a CH1 domain attached to a VH domain which pairs with a CL domain attached to a VL domain. In a wild-type immunoglobulin, the VH domain is paired with the VL domain to constitute the Fv region, and the CH1 domain is paired with the CL domain to further stabilize the binding module. A disulfide bond between the two constant domains can further stabilize the Fab domain.

For the MBMs of the disclosure, particularly when the light chain is not a common or universal light chain, it is advantageous to use Fab heterodimerization strategies to permit the correct association of Fab domains belonging to the same ABS and minimize aberrant pairing of Fab domains belonging to different ABSs. For example, the Fab heterodimerization strategies shown in Table 1 below can be used:

TABLE 1

Fab Heterodimerization Strategies

| STRATEGY | VH | CH1 | VL | CL | REFERENCE |
| --- | --- | --- | --- | --- | --- |
| CrossMabCH1-CL | WT | CL domain | WT | CH1 domain | Schaefer et al., 2011, Cancer Cell 2011; 20: 472-86; PMID: 22014573. |
| orthogonal Fab VHVRD1CH1CRD2-VLVRD1CλCRD2 | 39K, 62E | H172A, F174G | 1R, 38D, (36F) | L135Y, S176W | Lewis et al., 2014, Nat Biotechnol 32: 191-8 |
| orthogonal Fab VHVRD2CH1wt-VLVRD2CλWt | 39Y | WT | 38R | WT | Lewis et al., 2014, Nat Biotechnol 32: 191-8 |
| TCR CαCβ | 39K | TCR Cα | 38D | TCR Cβ | Wu et al., 2015, MAbs 7: 364-76 |
| CR3 | WT | T192E | WT | N137K, S114A | Golay at al., 2016, J Immunol 196: 3199-211. |
| MUT4 | WT | L143Q, S188V | WT | V133T, S176V | Golay at al., 2016, J Immunol 196: 3199-211. |
| DuetMab | WT | F126C | WT | S121C | Mazor et al., 2015, MAbs 7: 377-89; Mazor et al., 2015, MAbs 7: 461-669. |
| Domain exchanged | WT | CH3 + knob or hole mutation | WT | CH3 + hole or knob mutation | Wozniak-Knopp et al., 2018, PLoSONE13(4): e0195442 |

Accordingly, in certain embodiments, correct association between the two polypeptides of a Fab is promoted by exchanging the VL and VH domains of the Fab for each other or exchanging the CH1 and CL domains for each other, e.g., as described in WO 2009/080251.

Correct Fab pairing can also be promoted by introducing one or more amino acid modifications in the CH1 domain and one or more amino acid modifications in the CL domain of the Fab and/or one or more amino acid modifications in the VH domain and one or more amino acid modifications in the VL domain. The amino acids that are modified are typically part of the VH:VL and CH1:CL interface such that the Fab components preferentially pair with each other rather than with components of other Fabs.

In one embodiment, the one or more amino acid modifications are limited to the conserved framework residues of the variable (VH, VL) and constant (CH1, CL) domains as indicated by the Kabat numbering of residues. Almagro, 2008, Frontiers In Bioscience 13:1619-1633 provides a definition of the framework residues on the basis of Kabat, Chothia, and IMGT numbering schemes.

In one embodiment, the modifications introduced in the VH and CH1 and/or VL and CL domains are complementary to each other. Complementarity at the heavy and light chain interface can be achieved on the basis of steric and hydrophobic contacts, electrostatic/charge interactions or a combination of the variety of interactions. The complementarity between protein surfaces is broadly described in the literature in terms of lock and key fit, knob into hole, protrusion and cavity, donor and acceptor etc., all implying the nature of structural and chemical match between the two interacting surfaces.

In one embodiment, the one or more introduced modifications introduce a new hydrogen bond across the interface of the Fab components. In one embodiment, the one or more introduced modifications introduce a new salt bridge across the interface of the Fab components. Exemplary substitutions are described in WO 2014/150973 and WO 2014/082179, the contents of which are hereby incorporated by reference.

In some embodiments, the Fab domain comprises a 192E substitution in the CH1 domain and 114A and 137K substitutions in the CL domain, which introduces a salt-bridge between the CH1 and CL domains (see, e.g., Golay et al., 2016, J Immunol 196:3199-211).

In some embodiments, the Fab domain comprises a 143Q and 188V substitutions in the CH1 domain and 113T and 176V substitutions in the CL domain, which serves to swap hydrophobic and polar regions of contact between the CH1 and CL domain (see, e.g., Golay et al., 2016, J Immunol 196:3199-211).

In some embodiments, the Fab domain can comprise modifications in some or all of the VH, CH1, VL, CL domains to introduce orthogonal Fab interfaces which promote correct assembly of Fab domains (Lewis et al., 2014 Nature Biotechnology 32:191-198). In an embodiment, 39K, 62E modifications are introduced in the VH domain, H172A, F174G modifications are introduced in the CH1 domain, 1 R, 38D, (36F) modifications are introduced in the VL domain, and L135Y, S176W modifications are introduced in the CL domain. In another embodiment, a 39Y modification is introduced in the VH domain and a 38R modification is introduced in the VL domain.

Fab domains can also be modified to replace the native CH1:CL disulfide bond with an engineered disulfide bond, thereby increasing the efficiency of Fab component pairing. For example, an engineered disulfide bond can be introduced by introducing a 126C in the CH1 domain and a 121 C in the CL domain (see, e.g., Mazor et al., 2015, MAbs 7:377-89).

Fab domains can also be modified by replacing the CH1 domain and CL domain with alternative domains that promote correct assembly. For example, Wu et al., 2015, MAbs 7:364-76, describes substituting the CH1 domain with the constant domain of the a T cell receptor and substituting the CL domain with the b domain of the T cell receptor, and pairing these domain replacements with an additional charge-charge interaction between the VL and VH domains by introducing a 38D modification in the VL domain and a 39K modification in the VH domain.

In lieu of, or in addition to, the use of Fab heterodimerization strategies to promote correct VH-VL pairings, the VL of common light chain (also referred to as a universal light chain) can be used for each Fab VL region of a MBM of the disclosure. In various embodiments, employing a common light chain as described herein reduces the number of inappropriate species of MBMs as compared to employing original cognate VLs. In various embodiments, the VL domains of the MBMs are identified from monospecific antibodies comprising a common light chain. In various embodiments, the VH regions of the MBMs comprise human heavy chain variable gene segments that are rearranged in vivo within mouse B cells that have been previously engineered to express a limited human light chain repertoire, or a single human light chain, cognate with human heavy chains and, in response to exposure with an antigen of interest, generate an antibody repertoire containing a plurality of human VHs that are cognate with one or one of two possible human VLs, wherein the antibody repertoire specific for the antigen of interest. Common light chains are those derived from a rearranged human Vκ1-39Jκ5 sequence or a rearranged human Vκ3-20Jκ1 sequence, and include somatically mutated (e.g., affinity matured) versions. See, for example, U.S. Pat. No. 10,412, 940.

6.2.3. Linkers

In certain aspects, the present disclosure provides MBM in which two or more components of an ABS (e.g., a VH and a VL of an scFv), two or more ABSs (e.g., an scFv and a Fab of a half antibody), or an ABS and a non-ABS component (e.g., an Fc region) are connected to one another by a peptide linker. Such linkers are referred to herein an "ABS linkers", as opposed to the ADC linkers used to attach drugs to MBMs as described, for example, in Section 6.4.

A peptide linker can range from 2 amino acids to 60 or more amino acids, and in certain aspects a peptide linker ranges from 3 amino acids to 50 amino acids, from 4 to 30 amino acids, from 5 to 25 amino acids, from 10 to 25 amino acids, 10 amino acids to 60 amino acids, from 12 amino acids to 20 amino acids, from 20 amino acids to 50 amino acids, or from 25 amino acids to 35 amino acids in length.

In particular aspects, a peptide linker, e.g., a peptide linker separating an scFv domain and a heavy chain such as the scFv domain of ABS1 and the heavy chain variable region of ABS2, is at least 5 amino acids, at least 6 amino acids or at least 7 amino acids in length and optionally is up to 30 amino acids, up to 40 amino acids, up to 50 amino acids or up to 60 amino acids in length.

In some embodiments of the foregoing, the linker ranges from 5 amino acids to 50 amino acids in length, e.g., ranges from 5 to 50, from 5 to 45, from 5 to 40, from 5 to 35, from 5 to 30, from 5 to 25, or from 5 to 20 amino acids in length. In other embodiments of the foregoing, the linker ranges from 6 amino acids to 50 amino acids in length, e.g., ranges from 6 to 50, from 6 to 45, from 6 to 40, from 6 to 35, from 6 to 30, from 6 to 25, or from 6 to 20 amino acids in length. In yet other embodiments of the foregoing, the linker ranges from 7 amino acids to 50 amino acids in length, e.g., ranges from 7 to 50, from 7 to 45, from 7 to 40, from 7 to 35, from 7 to 30, from 7 to 25, or from 7 to 20 amino acids in length.

Charged (e.g., charged hydrophilic linkers) and/or flexible linkers are particularly preferred.

Examples of flexible ABS linkers that can be used in the MBMs of the disclosure include those disclosed by Chen et al., 2013, Adv Drug Deliv Rev. 65(10): 1357-1369 and Klein et al., 2014, Protein Engineering, Design & Selection 27(10): 325-330. Particularly useful flexible linkers are or comprise repeats of glycines and serines, e.g., a monomer or multimer of $G_nS$ (SEQ ID NO: 2) or $SG_n$ (SEQ ID NO: 3), where n is an integer from 1 to 10, e.g., 1 2, 3, 4, 5, 6, 7, 8, 9 or 10. In one embodiment, the linker is or comprises a monomer or multimer of repeat of $G_4S$ (SEQ ID NO: 4) e.g., $(GGGGS)_n$.

Polyglycine linkers can suitably be used in the MBMs of the disclosure. In some embodiments, the a peptide linker, e.g., a peptide linker separating an scFv domain and a heavy chain such as the scFv domain of ABS1 and the heavy chain variable region of ABS2, comprises two consecutive glycines (2Gly), three consecutive glycines (3Gly), four consecutive glycines (4Gly (SEQ ID NO: 5)), five consecutive glycines (5Gly (SEQ ID NO: 6)), six consecutive glycines (6Gly (SEQ ID NO: 7)), seven consecutive glycines (7Gly (SEQ ID NO: 8)), eight consecutive glycines (8Gly (SEQ ID NO: 9)) or nine consecutive glycines (9Gly (SEQ ID NO: 10)).

In particular embodiments the ABS linker, e.g., a peptide linker separating an scFv domain and a heavy chain such as the scFv domain of ABS1 and the heavy chain variable region of ABS2, is composed of both G4S (SEQ ID NO:4) or a multimer thereof and one or more additional glycines, e.g., 2Gly, 3Gly or 4Gly (SEQ ID NO:5). Examples of such linkers include $G_4S$ GG (SEQ ID NO:63), $4\times G_4S$ GG (SEQ ID NO:64) and $7\times G_4S$ GG (SEQ ID NO:65).

6.2.4. Hinge Regions

The MBMs of the disclosure can also comprise hinge regions, e.g., connecting an ABS module to an Fc region. The hinge region can be a native or a modified hinge region. Hinge regions are typically found at the N-termini of Fc regions.

A native hinge region is the hinge region that would normally be found between Fab and Fc domains in a naturally occurring antibody. A modified hinge region is any hinge that differs in length and/or composition from the native hinge region. Such hinges can include hinge regions from other species, such as human, mouse, rat, rabbit, shark, pig, hamster, camel, llama or goat hinge regions. Other modified hinge regions may comprise a complete hinge region derived from an antibody of a different class or subclass from that of the heavy chain Fc region. Alternatively, the modified hinge region may comprise part of a natural hinge or a repeating unit in which each unit in the repeat is derived from a natural hinge region. In a further alternative, the natural hinge region may be altered by converting one or more cysteine or other residues into neutral residues, such as serine or alanine, or by converting suitably placed residues into cysteine residues. By such means the number of cysteine residues in the hinge region may be increased or decreased. Other modified hinge regions may be entirely synthetic and may be designed to possess desired properties such as length, cysteine composition and flexibility.

A number of modified hinge regions have already been described for example, in U.S. Pat. No. 5,677,425, WO9915549, WO2005003170, WO2005003169, WO2005003170, WO9825971 and WO2005003171 and these are incorporated herein by reference.

In one embodiment, the Fc region of one or both half antibodies of the disclosure possesses an intact hinge region, e.g., a hinge domain, at its N-terminus. In some embodiments, "hinge domain" refers to the sequence from about Glu216 or about Cys226 to about Pro230 of human IgG1 (Burton, 1985 Molec. Immunol. 22:161-206), or the corresponding sequence in another antibody class or isotype.

In various embodiments, positions 233-236 within a hinge domain may be G, G, G and unoccupied; G, G, unoccupied, and unoccupied; G, unoccupied, unoccupied, and unoccupied; or all unoccupied, with positions numbered by EU numbering.

In some embodiments, the MBMs of the disclosure comprise a modified hinge domain that reduces binding affinity for an Fcγ receptor relative to a wild-type hinge domain of the same isotype (e.g., human IgG1 or human IgG4).

In one embodiment, the Fc region of one or both chains of the MBMs of disclosure possesses an intact hinge domain at its N-terminus.

In one embodiment both the Fc region and the hinge region of an MBM of the disclosure are derived from IgG4 and the hinge region comprises the modified sequence CPPC (SEQ ID NO: 11). The core hinge region of human IgG4 contains the sequence CPSC (SEQ ID NO: 12) compared to IgG1 that contains the sequence CPPC (SEQ ID NO: 11). The serine residue present in the IgG4 sequence leads to increased flexibility in this region, and therefore a proportion of molecules form disulfide bonds within the same protein chain (an intrachain disulfide) rather than bridging to the other heavy chain in the IgG molecule to form the interchain disulfide (Angel et al., 1993, Mol Immunol 30(1): 105-108). Changing the serine residue to a proline to give the same core sequence as IgG1 allows complete formation of inter-chain disulfides in the IgG4 hinge region, thus reducing heterogeneity in the purified product. This altered isotype is termed IgG4P.

6.2.4.1. Chimeric Hinge Sequences

The hinge region can be a chimeric hinge region.

For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region.

In particular embodiments, a chimeric hinge region comprises the amino acid sequence EPKSCDKTHTCPPCPAPPVA (SEQ ID NO: 13) (previously disclosed as SEQ ID NO:8 of WO2014/121087, which is incorporated by reference in its entirety herein) or ESKYGPPCPPCPAPPVA (SEQ ID NO: 14) (previously disclosed as SEQ ID NO:9 of WO2014/121087). Such chimeric hinge sequences can be suitably linked to an IgG4 CH2 region (for example by incorporation into an IgG4 Fc domain, for example a human or murine Fc domain, which can be further modified in the CH2 and/or CH3 domain to reduce effector function, for example as described in Section 6.2.5.1).

6.2.4.2. Hinge Sequences with Reduced Effector Function

In further embodiments, the hinge region can be modified to reduce effector function, for example as described in WO2016161010A2, which is incorporated by reference in its entirety herein. In various embodiments, the positions 233-236 of the modified hinge region are G, G, G and unoccupied; G, G, unoccupied, and unoccupied; G, unoccupied, unoccupied, and unoccupied; or all unoccupied, with positions numbered by EU numbering (as shown in FIG. 1 of WO2016161010A2). These segments can be represented as GGG-, GG--, G--- or ---- with "-" representing an unoccupied position.

Position 236 is unoccupied in canonical human IgG2 but is occupied by in other canonical human IgG isotypes. Positions 233-235 are occupied by residues other than G in all four human isotypes (as shown in FIG. 1 of WO2016161010A2).

The hinge modification within positions 233-236 can be combined with position 228 being occupied by P. Position 228 is naturally occupied by P in human IgG1 and IgG2 but is occupied by S in human IgG4 and R in human IgG3. An S228P mutation in an IgG4 antibody is advantageous in stabilizing an IgG4 antibody and reducing exchange of heavy chain light chain pairs between exogenous and endogenous antibodies. Preferably positions 226-229 are occupied by C, P, P and C respectively.

Exemplary hinge regions have residues 226-236, sometimes referred to as middle (or core) and lower hinge, occupied by the modified hinge sequences designated GGG-(233-236), GG--(233-236), G---(233-236) and no G(233-236). Optionally, the hinge domain amino acid sequence comprises CPPCPAPGGG-GPSVF (SEQ ID NO: 15) (previously disclosed as SEQ ID NO:1 of WO2016161010A2), CPPCPAPGG--GPSVF (SEQ ID NO: 16) (previously disclosed as SEQ ID NO:2 of WO2016161010A2), CPPCPAPG---GPSVF (SEQ ID NO: 17) (previously disclosed as SEQ ID NO:3 of WO2016161010A2), or CPPCPAP----GPSVF (SEQ ID NO: 18) (previously disclosed as SEQ ID NO:4 of WO2016161010A2).

The modified hinge regions described above can be incorporated into a heavy chain constant region, which typically include CH2 and CH3 domains, and which may have an additional hinge segment (e.g., an upper hinge) flanking the designated region. Such additional constant region segments present are typically of the same isotype, preferably a human isotype, although can be hybrids of different isotypes. The isotype of such additional human constant regions segments is preferably human IgG4 but can also be human IgG1, IgG2, or IgG3 or hybrids thereof in which domains are of different isotypes. Exemplary sequences of human IgG1, IgG2 and IgG4 are shown in FIGS. 2-4 of WO2016161010A2.

In specific embodiments, the modified hinge sequences can be linked to an IgG4 CH2 region (for example by incorporation into an IgG4 Fc domain, for example a human or murine Fc domain, which can be further modified in the CH2 and/or CH3 domain to reduce effector function, for example as described in Section 6.2.5.1).

6.2.5. Fc Domains

The MBMs of the disclosure can include an Fc region derived from any suitable species. In one embodiment the Fc region is derived from a human Fc domain.

The Fc domain can be derived from any suitable class of antibody, including IgA (including subclasses IgA1 and IgA2), IgD, IgE, IgG (including subclasses IgG1, IgG2, IgG3 and IgG4), and IgM. In one embodiment, the Fc domain is derived from IgG1, IgG2, IgG3 or IgG4. In one embodiment the Fc domain is derived from IgG1. In one embodiment the Fc domain is derived from IgG4.

The two Fc domains within the Fc region can be the same or different from one another. In a native antibody the Fc domains are typically identical, but for the purpose of producing multispecific binding molecules, e.g., the MBMs of the disclosure, the Fc domains might advantageously be different to allow for heterodimerization, as described in Section 6.2.5.2 below.

In native antibodies, the heavy chain Fc domain of IgA, IgD and IgG is composed of two heavy chain constant domains (CH2 and CH3) and that of IgE and IgM is composed of three heavy chain constant domains (CH2, CH3 and CH4). These dimerize to create an Fc region.

In MBMs of the present disclosure, the Fc region, and/or the Fc domains within it, can comprise heavy chain constant domains from one or more different classes of antibody, for example one, two or three different classes.

In one embodiment the Fc region comprises CH2 and CH3 domains derived from IgG1.

In one embodiment the Fc region comprises CH2 and CH3 domains derived from IgG2.

In one embodiment the Fc region comprises CH2 and CH3 domains derived from IgG3.

In one embodiment the Fc region comprises CH2 and CH3 domains derived from IgG4.

In one embodiment the Fc region comprises a CH4 domain from IgM. The IgM CH4 domain is typically located at the C-terminus of the CH3 domain.

In one embodiment the Fc region comprises CH2 and CH3 domains derived from IgG and a CH4 domain derived from IgM.

It will be appreciated that the heavy chain constant domains for use in producing an Fc region for the MBMs of the present disclosure may include variants of the naturally occurring constant domains described above. Such variants may comprise one or more amino acid variations compared to wild type constant domains. In one example the Fc region of the present disclosure comprises at least one constant domain that varies in sequence from the wild type constant domain. It will be appreciated that the variant constant domains may be longer or shorter than the wild type constant domain. Preferably the variant constant domains are at least 60% identical or similar to a wild type constant domain. In another example the variant constant domains are at least 70% identical or similar. In another example the variant constant domains are at least 80% identical or similar. In another example the variant constant domains are at least 90% identical or similar. In another example the variant constant domains are at least 95% identical or similar.

IgM and IgA occur naturally in humans as covalent multimers of the common H2L2 antibody unit. IgM occurs as a pentamer when it has incorporated a J-chain, or as a hexamer when it lacks a J-chain. IgA occurs as monomer and dimer forms. The heavy chains of IgM and IgA possess an 18 amino acid extension to the C-terminal constant domain, known as a tailpiece. The tailpiece includes a cysteine residue that forms a disulfide bond between heavy chains in the polymer, and is believed to have an important role in polymerization. The tailpiece also contains a glycosylation site. In certain embodiments, the MBMs of the present disclosure do not comprise a tailpiece.

The Fc domains that are incorporated into the MBMs of the present disclosure may comprise one or more modifications that alter the functional properties of the proteins, for example, binding to Fc-receptors such as FcRn or leukocyte receptors, binding to complement, modified disulfide bond architecture, or altered glycosylation patterns. Exemplary Fc modifications that alter effector function are described in Section 6.2.5.1

The Fc domains can also be altered to include modifications that improve manufacturability of asymmetric MBMs, for example by allowing heterodimerization, which is the preferential pairing of non-identical Fc domains over identical Fc domains. Heterodimerization permits the production of MBMs in which different ABSs are connected to one another by an Fc region containing Fc domains that differ in sequence. Examples of heterodimerization strategies are exemplified in Section 6.2.5.2.

It will be appreciated that any of the modifications mentioned above can be combined in any suitable manner to achieve the desired functional properties and/or combined with other modifications to alter the properties of the MBMs.

6.2.5.1. Fc Domains with Altered Effector Function

In some embodiments, the Fc domain comprises one or more amino acid substitutions that reduces binding to an Fc receptor and/or effector function.

In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of complement dependent cytotoxicity (CDC), antibody-dependent cell-mediated cytotoxicity (ADCC), antibody-dependent cellular phagocytosis (ADCP), and cytokine secretion. In a particular embodiment, the effector function is ADCC.

In one embodiment, the Fc region comprises an amino acid substitution at a position selected from the group of E233, L234, L235, N297, P331 and P329 (numberings according to Kabat EU index). In a more specific embodiment, the Fc region comprises an amino acid substitution at a position selected from the group of L234, L235 and P329 (numberings according to Kabat EU index). In some embodiments, the Fc region comprises the amino acid substitutions L234A and L235A (numberings according to Kabat EU index). In one such embodiment, the Fc region is an Igd Fc region, particularly a human Igd Fc region. In one embodiment, the Fc region comprises an amino acid substitution at position P329. In a more specific embodiment, the amino acid substitution is P329A or P329G, particularly P329G (numberings according to Kabat EU index). In one embodiment, the Fc region comprises an amino acid substitution at position P329 and a further amino acid substitution at a position selected from E233, L234, L235, N297 and P331 (numberings according to Kabat EU index). In a more specific embodiment, the further amino acid substitution is E233P, L234A, L235A, L235E, N297A, N297D or P331S. In particular embodiments, the Fc region comprises amino acid substitutions at positions P329, L234 and L235 (numberings according to Kabat EU index). In more particular embodiments, the Fc region comprises the amino acid mutations L234A, L235A and P329G ("P329G LALA", "PGLALA" or "LALAPG").

Typically, the same one or more amino acid substitution is present in each of the two Fc domains of an Fc region. Thus, in a particular embodiment, each Fc domain of the Fc region comprises the amino acid substitutions L234A, L235A and P329G (Kabat EU index numbering), i.e. in each of the first and the second Fc domains in the Fc region the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

In one embodiment, the Fc domain is an IgG1 Fc domain, particularly a human IgG1 Fc domain.

Typically, the same one or more amino acid substitution is present in each of the two Fc domains of an Fc region. Thus, in a particular embodiment, each Fc domain of the Fc region comprises the amino acid substitutions L234A, L235A and P329G (Kabat EU index numbering), i.e. in each of the first and the second Fc domains in the Fc region the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

In one embodiment, the Fc domain is an IgG1 Fc domain, particularly a human IgG1 Fc domain. In some embodiments, the IgG1 Fc domain is a variant IgG1 comprising D265A, N297A mutations (EU numbering) to reduce effector function.

In another embodiment, the Fc domain is an IgG4 Fc domain with reduced binding to Fc receptors. Exemplary IgG4 Fc domains with reduced binding to Fc receptors may comprise an amino acid sequence selected from Table A below. In some embodiments, the Fc domain includes only the bolded portion of the sequences shown below:

TABLE A

| Fc Domain | Sequence | SEQ ID NO: |
|---|---|---|
| SEQ ID NO: 1 of WO2014/121087 | Asp Lys Arg Val Glu Ser Lys Tyr Gly Pro Pro Cys Pro Pro Cys Pro Ala Pro Pro Val Ala Gly Pro Ser Val Phe Leu Phe Pro Pro Lys Pro Lys Asp Thr Leu Met Ile Ser Arg Thr Pro Glu Val Thr Cys Val Val Val Asp Val Ser Gln Glu Asp Pro Glu Val Gln Phe Asn Trp Tyr Val Asp Gly Val Glu Val His Asn Ala Lys Thr Lys Pro Arg Glu Glu Gln Phe Asn Ser Thr Tyr Arg Val Val Ser Val Leu Thr Val Leu His Gln Asp Trp Leu Asn Gly Lys Glu Tyr Lys Cys Lys Val Ser Asn Lys Gly Leu Pro Ser Ser Ile Glu Lys Thr Ile Ser Lys Ala Lys Gly Gln Pro Arg Glu Pro Gln Val Tyr Thr Leu Pro Pro Ser Gln Glu Glu Met Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Arg Leu Thr Val Asp Lys Ser Arg Trp Gln Glu Gly Asn Val Phe Ser Cys Ser Val Met His Glu Ala Leu His Asn His Tyr Thr Gln Lys Ser Leu Ser Leu Ser Leu Gly Lys | 19 |

TABLE A-continued

| Fc Domain | Sequence | SEQ ID NO: |
|---|---|---|
| SEQ ID NO: 2 of WO2014/121087 | Asp Lys Lys Val Glu Pro Lys Ser Cys Asp Lys Thr His Thr Cys Pro Pro Cys Pro Ala Pro Pro Val Ala Gly Pro Ser Val Phe Leu Phe Pro Pro Lys Pro Lys Asp Thr Leu Met Ile Ser Arg Thr Pro Glu Val Thr Cys Val Val Val Asp Val Ser Gln Glu Asp Pro Glu Val Gln Phe Asn Trp Tyr Val Asp Gly Val Glu Val His Asn Ala Lys Thr Lys Pro Arg Glu Glu Gln Phe Asn Ser Thr Tyr Arg Val Val Ser Val Leu Thr Val Leu His Gln Asp Trp Leu Asn Gly Lys Glu Tyr Lys Cys Lys Val Ser Asn Lys Gly Leu Pro Ser Ser Ile Glu Lys Thr Ile Ser Lys Ala Lys Gly Gln Pro Arg Glu Pro Gln Val Tyr Thr Leu Pro Pro Ser Arg Asp Glu Leu Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly Lys | 20 |
| SEQ ID NO: 30 of WO2014/121087 | Ala Ser Thr Lys Gly Pro Ser Val Phe Pro Leu Ala Pro Ser Ser Lys Ser Thr Ser Gly Gly Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Ser Leu Gly Thr Gln Thr Tyr Ile Cys Asn Val Asn His Lys Pro Ser Asn Thr Lys Val Asp Lys Lys Val Glu Pro Lys Ser Cys Asp Lys Thr His Thr Cys Pro Pro Cys Pro Ala Pro Pro Val Ala Gly Pro Ser Val Phe Leu Phe Pro Pro Lys Pro Lys Asp Thr Leu Met Ile Ser Arg Thr Pro Glu Val Thr Cys Val Val Val Asp Val Ser Gln Glu Asp Pro Glu Val Gln Phe Asn Trp Tyr Val Asp Gly Val Glu Val His Asn Ala Lys Thr Lys Pro Arg Glu Glu Gln Phe Asn Ser Thr Tyr Arg Val Val Ser Val Leu Thr Val Leu His Gln Asp Trp Leu Asn Gly Lys Glu Tyr Lys Cys Lys Val Ser Asn Lys Gly Leu Pro Ser Ser Ile Glu Lys Thr Ile Ser Lys Ala Lys Gly Gln Pro Arg Glu Pro Gln Val Tyr Thr Leu Pro Pro Ser Arg Asp Glu Leu Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly Lys | 21 |
| SEQ ID NO: 31 of WO2014/121087 | Ala Ser Thr Lys Gly Pro Ser Val Phe Pro Leu Ala Pro Cys Ser Arg Ser Thr Ser Glu Ser Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Ser Leu Gly Thr Lys Thr Tyr Thr Cys Asn Val Asp His Lys Pro Ser Asn Thr Lys Val Asp Lys Arg Val Glu Ser Lys Tyr Gly Pro Pro Cys Pro Pro Cys Pro Ala Pro Pro Val Ala Gly Pro Ser Val Phe Leu Phe Pro Pro Lys Pro Lys Asp Thr Leu Met Ile Ser Arg Thr Pro Glu Val Thr Cys Val Val Val Asp Val Ser Gln Glu Asp Pro Glu Val Gln Phe Asn Trp Tyr Val Asp Gly Val Glu Val His Asn Ala Lys Thr Lys Pro Arg Glu Glu Gln Phe Asn Ser Thr Tyr Arg Val Val Ser Val Leu Thr Val Leu His Gln Asp Trp Leu Asn Gly Lys Glu Tyr Lys Cys Lys Val Ser Asn Lys Gly Leu Pro Ser Ser Ile Glu Lys Thr Ile Ser Lys Ala Lys Gly Gln Pro Arg Glu Pro Gln Val Tyr Thr Leu Pro Pro Ser Gln Glu Glu Met Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Arg Leu Thr Val Asp Lys Ser Arg Trp Gln Glu Gly Asn Val Phe Ser Cys Ser Val Met His Glu Ala Leu His Asn His Tyr Thr Gln Lys Ser Leu Ser Leu Ser Leu Gly Lys | 22 |
| SEQ ID NO: 37 of WO2014/121087 | Ala Ser Thr Lys Gly Pro Ser Val Phe Pro Leu Ala Pro Ser Ser Lys Ser Thr Ser Gly Gly Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Ser Leu Gly Thr Gln Thr Tyr Ile Cys Asn Val Asn His Lys Pro Ser Asn Thr Lys Val Asp Lys Lys Val Glu Pro Lys Ser Cys Asp Lys Thr His Thr Cys Pro Pro Cys Pro Ala Pro Pro Val Ala Gly Pro Ser Val Phe Leu Phe Pro Pro Lys Pro Lys Asp Thr Leu Met Ile Ser Arg Thr Pro Glu | 23 |

TABLE A-continued

| Fc Domain | Sequence | SEQ ID NO: |
|---|---|---|
| | Val Thr Cys Val Val Val Asp Val Ser Gln Glu Asp Pro Glu Val<br>Gln Phe Asn Trp Tyr Val Asp Gly Val Glu Val His Asn Ala Lys<br>Thr Lys Pro Arg Glu Glu Gln Phe Asn Ser Thr Tyr Arg Val Val<br>Ser Val Leu Thr Val Leu His Gln Asp Trp Leu Asn Gly Lys<br>Glu Tyr Lys Cys Lys Val Ser Asn Lys Gly Leu Pro Ser Ser Ile<br>Glu Lys Thr Ile Ser Lys Ala Lys Gly Gln Pro Arg Glu Pro Gln<br>Val Tyr Thr Leu Pro Pro Ser Arg Asp Glu Leu Thr Lys Asn<br>Gln Val Ser Leu Thr Cys Leu Val Lys Gly Phe Tyr Pro Ser<br>Asp Ile Ala Val Glu Trp Glu Ser Asn Gly Gln Pro Glu Asn Asn<br>Tyr Lys Thr Thr Pro Pro Val Leu Asp Ser Asp Gly Ser Phe<br>Phe Leu Tyr Ser Lys Leu Thr Val Asp Lys Ser Arg Trp Gln<br>Gln Gly Asn Val Phe Ser Cys Ser Val Met His Glu Ala Leu His<br>Asn Arg Phe Thr Gln Lys Ser Leu Ser Leu Ser Pro Gly Lys | |
| SEQ ID NO: 38 of WO2014/121087 | Ala Ser Thr Lys Gly Pro Ser Val Phe Pro Leu Ala Pro Cys Ser<br>Arg Ser Thr Ser Glu Ser Thr Ala Ala Leu Gly Cys Leu Val Lys<br>Asp Tyr Phe Pro Glu Pro Val Thr Val Ser Trp Asn Ser Gly Ala<br>Leu Thr Ser Gly Val His Thr Phe Pro Ala Val Leu Gln Ser Ser Gly<br>Leu Tyr Ser Leu Ser Ser Val Val Thr Val Pro Ser Ser Ser Leu Gly<br>Thr Lys Thr Tyr Thr Cys Asn Val Asp His Lys Pro Ser Asn Thr<br>Lys Val Asp Lys Arg Val Glu Ser Lys Tyr Gly Pro Pro Cys Pro<br>Pro Cys Pro Ala Pro Pro Val Ala Gly Pro Ser Val Phe Leu Phe<br>Pro Pro Lys Pro Lys Asp Thr Leu Met Ile Ser Arg Thr Pro Glu<br>Val Thr Cys Val Val Val Asp Val Ser Gln Glu Asp Pro Glu Val<br>Gln Phe Asn Trp Tyr Val Asp Gly Val Glu Val His Asn Ala Lys<br>Thr Lys Pro Arg Glu Glu Gln Phe Asn Ser Thr Tyr Arg Val Val<br>Ser Val Leu Thr Val Leu His Gln Asp Trp Leu Asn Gly Lys<br>Glu Tyr Lys Cys Lys Val Ser Asn Lys Gly Leu Pro Ser Ser Ile<br>Glu Lys Thr Ile Ser Lys Ala Lys Gly Gln Pro Arg Glu Pro Gln<br>Val Tyr Thr Leu Pro Pro Ser Gln Glu Glu Met Thr Lys Asn<br>Gln Val Ser Leu Thr Cys Leu Val Lys Gly Phe Tyr Pro Ser<br>Asp Ile Ala Val Glu Trp Glu Ser Asn Gly Gln Pro Glu Asn Asn<br>Tyr Lys Thr Thr Pro Pro Val Leu Asp Ser Asp Gly Ser Phe<br>Phe Leu Tyr Ser Arg Leu Thr Val Asp Lys Ser Arg Trp Gln<br>Glu Gly Asn Val Phe Ser Cys Ser Val Met His Glu Ala Leu His<br>Asn Arg Phe Thr Gln Lys Ser Leu Ser Leu Ser Leu Gly Lys | 24 |

In a particular embodiment, the IgG4 with reduced effector function comprises the bolded portion of the amino acid sequence of SEQ ID NO:31 of WO2014/121087, sometimes referred to herein as IgG4s or hIgG4s.

For heterodimeric MBMs, it is possible to incorporate a combination of the variant IgG4 Fc sequences set forth above, for example an Fc region comprising a combination of SEQ ID NO:30 of WO2014/121087 (or the bolded portion thereof) and SEQ ID NO:37 of WO2014/121087 (or the bolded portion thereof) or an Fc region comprising a combination of SEQ ID NO:31 of WO2014/121087 (or the bolded portion thereof) and SEQ ID NO:38 of WO2014/121087 (or the bolded portion thereof).

6.2.5.2. Fc Heterodimerization Variants

Many multispecific molecule formats entail dimerization between two Fc domains that, unlike a native immunoglobulin, are operably linked to non-identical antigen-binding domains (or portions thereof, e.g., a VH or VH-CH1 of a Fab). Inadequate heterodimerization of two Fc regions to form an Fc domain has can be an obstacle for increasing the yield of desired multispecific molecules and represents challenges for purification. A variety of approaches available in the art can be used in for enhancing dimerization of Fc domains that might be present in the MBMs of the disclosure, for example as disclosed in EP 1870459A1; U.S. Pat. Nos. 5,582,996; 5,731,168; 5,910,573; 5,932,448; 6,833,441; 7,183,076; U.S. Patent Application Publication No. 2006204493A1; and PCT Publication No. WO2009/089004A1.

The present disclosure provides MBMs comprising Fc heterodimers, i.e., Fc regions comprising heterologous, non-identical Fc domains. Heterodimerization strategies are used to enhance dimerization of Fc regions operably linked to different ABSs (or portions thereof, e.g., a VH or VH-CH1 of a Fab) and reduce dimerization of Fc domains operably linked to identical ABSs. Typically, each Fc domain in the Fc heterodimer comprises a CH3 domain of an antibody. The CH3 domains are derived from the constant region of an antibody of any isotype, class or subclass, and preferably of IgG (IgG1, IgG2, IgG3 and IgG4) class, as described in the preceding section.

Heterodimerization of the two different heavy chains at CH3 domains give rise to the desired MBM, while homodimerization of identical heavy chains will reduce yield of the desired MBM. Thus, in a preferred embodiment, the two half antibodies that associate to form an MBM of the disclosure will contain CH3 domains with modifications that favor heterodimeric association relative to unmodified chains.

In a specific embodiment said modification promoting the formation of Fc heterodimers is a so-called "knob-into-hole" or "knob-in-hole" modification, comprising a "knob" modification in one of the Fc domains and a "hole" modification in the other Fc domain. The knob-into-hole technology is described e.g. in U.S. Pat. Nos. 5,731,168; 7,695,936; Ridgway et al., 1996, Prot Eng 9:617-621, and Carter, 2001, Immunol Meth 248:7-15. Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g., tyrosine or tryptophan). Compensatory cavities of identical or similar size to the protuberances are created in the interface of the second polypeptide by replacing large amino acid side chains with smaller ones (e.g., alanine or threonine).

Accordingly, in some embodiments, an amino acid residue in the CH3 domain of the first subunit of the Fc domain is replaced with an amino acid residue having a larger side chain volume, thereby generating a protuberance within the CH3 domain of the first subunit which is positionable in a cavity within the CH3 domain of the second subunit, and an amino acid residue in the CH3 domain of the second subunit of the Fc domain is replaced with an amino acid residue having a smaller side chain volume, thereby generating a cavity within the CH3 domain of the second subunit within which the protuberance within the CH3 domain of the first subunit is positionable. Preferably said amino acid residue having a larger side chain volume is selected from the group consisting of arginine (R), phenylalanine (F), tyrosine (Y), and tryptophan (W). Preferably said amino acid residue having a smaller side chain volume is selected from the group consisting of alanine (A), serine (S), threonine (T), and valine (V). The protuberance and cavity can be made by altering the nucleic acid encoding the polypeptides, e.g. by site-specific mutagenesis, or by peptide synthesis. An exemplary substitution is Y470T.

In a specific such embodiment, in the first Fc domain the threonine residue at position 366 is replaced with a tryptophan residue (T366W), and in the Fc domain the tyrosine residue at position 407 is replaced with a valine residue (Y407V) and optionally the threonine residue at position 366 is replaced with a serine residue (T366S) and the leucine residue at position 368 is replaced with an alanine residue (L368A) (numbering according to Kabat EU index). In a further embodiment, in the first Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second Fc domain additionally the tyrosine residue at position 349 is replaced by a cysteine residue (Y349C) (numbering according to Kabat EU index). In a particular embodiment, the first Fc domain comprises the amino acid substitutions S354C and T366W, and the second Fc domain comprises the amino acid substitutions Y349C, T366S, L368A and Y407V (numbering according to Kabat EU index).

In some embodiments, electrostatic steering (e.g., as described in Gunasekaran et al., 2010, J Biol Chem 285(25): 19637-46) can be used to promote the association of the first and the second subunit of the Fc domain.

As an alternative, or in addition, to the use of Fc domains that are modified to promote heterodimerization, an Fc domain can be modified to allow a purification strategy that enables selections of Fc heterodimers. In one such embodiment, one half antibody comprises a modified Fc domain that abrogates its binding to Protein A, thus enabling a purification method that yields a heterodimeric protein. See, for example, U.S. Pat. No. 8,586,713. As such, the MBMs comprise a first CH3 domain and a second Ig CH3 domain, wherein the first and second Ig CH3 domains differ from one another by at least one amino acid, and wherein at least one amino acid difference reduces binding of the MBM to Protein A as compared to a corresponding MBM lacking the amino acid difference. In one embodiment, the first CH3 domain binds Protein A and the second CH3 domain contains a mutation/modification that reduces or abolishes Protein A binding such as an H95R modification (by IMGT exon numbering; H435R by EU numbering). The second CH3 may further comprise a Y96F modification (by IMGT; Y436F by EU). Thus class of modifications is referred to herein as "star" mutations.

6.3. Target Molecules

ABS1, ABS2, and ABS3 of the MBMs of the disclosure each specifically bind to a target molecule, for example a cell-surface expressed antigen such as a protein, carbohydrate, or lipid. In some embodiments, the target molecules bound by ABS1, ABS2, and ABS3 are protein molecules. Exemplary target molecules include human klotho beta ("KLB"), human fibroblast growth factor receptor 1c isoform ("FGFR1c"), human fibroblast growth factor receptor 3 ("FGFR3"), human CD63, and human amyloid precursor-like protein 2 (APLP2).

Preferably, the scFv, Fab1, and Fab2 are selected so that each of ABS1, ABS2, and ABS3 is capable of specifically binding its respective target at the same time. In some embodiments, ABS1, ABS2, and ABS3 each specifically bind a different target molecule. In other embodiments, two of ABS1, ABS2, and ABS3 can bind to different epitopes on the same target molecule.

When two of ABS1, ABS2, and ABS3 bind to different epitopes on the same target molecule, binding to the target molecule is preferably non-competitive, i.e., the ABSs do not compete for binding to the target molecule (which might occur, e.g., if the epitopes were overlapping). Assays for measuring binding competition between antibodies and antibody fragments are known in the art and include, for example, enzyme-linked immunosorbent assays (ELISA), fluorescence activated cell sorting (FACS) assays and surface plasmon resonance assays.

Competition for binding to a target molecule can be determined, for example, using a real time, label-free bio-layer interferometry assay on the Octet HTX biosensor platform (Pall ForteBio Corp.). In a specific embodiment of the assay, the entire assay is performed at 25° C. in a buffer of 10 mM HEPES, 150 mM NaCl, 3 mM EDTA, 1 mg/mL BSA, 0.05% v/v Surfactant Tween-20, pH 7.4 (HBS-EBT buffer) with the plate shaking at the speed of 1000 rpm. To assess whether two antibodies or antigen-binding fragments thereof are able to compete with one another for binding to their respective epitopes on their specific target antigen, a penta-His tagged target antigen ("penta-His" disclosed as SEQ ID NO: 25) is first captured on to anti-penta-His antibody ("penta-His" disclosed as SEQ ID NO: 25) coated Octet biosensor tips (Fortebio Inc, #18-5122) by submerging the biosensor tips in wells containing the penta-His tagged target antigen ("penta-His" disclosed as SEQ ID NO: 25). The antigen captured biosensor tips are then saturated with a first antibody or antigen-binding fragment thereof (subsequently referred to as Ab-1) by dipping into wells containing a solution of Ab-1 (e.g., a 50 µg/mL solution). The biosensor tips are then subsequently dipped into wells containing a solution (e.g., a 50 µg/mL solution) of a second antibody or antigen-binding fragment thereof (subsequently referred to as Ab-2). The biosensor tips are washed in HBS-EBT buffer in between every step of the assay. The real-time binding response can be monitored during the entire course of the assay and the binding response at the end of every step can be recorded. The response of Ab-2 binding to the target antigen pre-complexed with Ab-1 can be compared and competitive/non-competitive behavior of different antibodies/antigen-binding fragments against the same target antigen can be determined.

MBMs binding at least two or more different target molecules can be used, for example, to preferentially target a specific tissue type on which the two or more target molecules are expressed while minimizing binding to other tissue types to which binding is not desirable. For example, when one or two of ABS1, ABS2, and ABS3 bind to a first target molecule with a first tissue expression profile and at least one of ABS1, ABS2, and ABS3 binds to a second, different target molecule with a second expression profile that overlaps with, but is not identical to the first tissue expression profile, the MBM can be targeted the common tissue(s) of the first and second expression profiles.

MBMs having more than one ABS that bind to the same target molecule (whether on the same epitope or on different epitopes) can be useful for clustering and activating cell surface receptors.

The expression profiles can be determined empirically or obtained from public databases, such as the Genotype-Tissue Expression (GTEx) project and the Human Protein Atlas. The target selection can be based on protein expression profiles, mRNA expression profiles, or both. To minimize MBM activity at undesirable tissue sites, the tissue expression overlap between any two or all three of ABS1, ABS2 and ABS3 is preferably less than 10 tissues, for example 9 tissues, 8 tissues, 7 tissues, 6 tissues, 5 tissues, 4 tissues, 3 tissues, 2 tissues or 1 tissue. An exemplary tissue profile analysis is shown for an exemplary target pair bound by the MBMs of the disclosure, KLB and FGFR1c, is shown in FIGS. 4A (based on the GTEx database) and 4B (based on the HPA database).

In various embodiments:
ABS1 and ABS2 bind to the same or different epitopes on the same target molecule and ABS3 binds to a different target molecule;
ABS1 and ABS3 bind to the same or different epitopes on the same target molecule and ABS2 binds to a different target molecule;
ABS2 and ABS3 bind to the same or different epitopes on the same target molecule and ABS1 binds to a different target molecule;
ABS1, ABS2 and ABS3 bind to different target molecules; or
ABS1, ABS2 and ABS3 bind to the same or different epitopes on the same target molecule.

When two or more of ABS1, ABS2 and ABS3 bind to the same epitope on a target molecule, such ABSs can have the same or different VH sequences and/or VL sequences.

Without being bound by theory, it is believed that MBMs of the disclosure have the advantage of binding to a target molecule (or cell expressing a target molecule) with greater affinity than a parental monospecific antibody or bispecific antibody lacking the all three ABS's. Accordingly, the MBMs of the disclosure can in some embodiments bind to one or more target molecules and/or a cell expressing one or more target molecules with greater affinity than a parental monospecific antibody or bispecific antibody lacking all three ABS's, for example a bispecific antibody lacking the scFv of ABS1. For example, MBMs can in some embodiments having a lower KD for binding to a target molecule and/or have more potent EC50 values in a cell based binding assay than a corresponding parental monospecific antibody or bispecific antibody (e.g., as described in Section 7).

The agonist or antagonist activity of a given antibody or MBM depends on target selection, epitope coverage and choice of format. Identification of agonistic and antagonistic antibodies can be achieved, for example, through functional based screening. N-terminal scFv MBMs of the disclosure typically have agonist or antagonist activity when the parental antibody or the parental bispecific antibody before scFv fusion have agonist or antagonist activity, respectively. Without being bound by theory, it is believed that the MBMs of the disclosure are characterized by enhanced activity (e.g. agonist or antagonist activities) as compared to traditional bispecific molecules (e.g., parental bispecific molecules containing two Fabs but lacking an N-terminal scFv domain), e.g., due to novel binding stoichiometries conferred by the additional N-terminal scFv domain.

6.3.1. KLB-FGFR1c Binders

MBMs of the disclosure can in some embodiments contain one of more ABSs that bind to human KLB and one or more ABSs that bind to human FGFR1c (e.g., to loop D2 or D3). Human tissues that express both KLB and FGFR1c include adipose tissue, mammary tissue, liver, lung, pancreas, stomach, and testis (see, FIGS. 4A-4B). Thus, MBMs of the disclosure having one of more ABSs that bind to human KLB and one or more ABSs that bind to human FGFR1c can preferentially target these tissue types. FGF21, a member of the FGF family, signals through a receptor complex composed of FGFR1c and KLB and so acts as endocrine hormone. In one exemplary configuration of this target pair, ABS1 and ABS3 bind to different epitopes of KLB and ABS2 binds to FGFR1c. Without being bound by theory, it is believed that the binding of an MBM having this configuration agonizes the receptor complexes and results in the metabolic benefits illustrated in FIG. 5.

Exemplary anti-KLB antibodies are provided in Table 2A and VH and VL sequences of exemplary anti-KLB antibodies that can be used in the MBMs of the disclosure are provided in Table 2B. A MBM of the disclosure can include, for example, CDR or VH and/or VL sequences of any of the anti-KLB antibodies provided in Table 2A or Table 2B. Exemplary anti-FGFR1c antibodies are provided in Table 3A and VH and VL sequences of exemplary anti-FGFR1c antibodies that can be used in the MBMs of the disclosure are provided in Table 3B. A MBM of the disclosure can include, for example, CDR or VH and/or VL sequences of any of the anti-FGFR1c antibodies provided in Table 3A or Table 3B.

TABLE 2A

KLB Binders

| Name | Reference | Sequence in Patent Reference |
|---|---|---|
| 39F7 (Amgen) | U.S. Pat. No. 8,263,074; J. Biol. Chem. (2018) 293, 14678 | Heavy chain: Seq ID No. 82; Light chain: Seq ID No. 27 |
| mimAb1 (Amgen) | US 2011/0135657; Sci. Transl. Med. (2012) 4, 162ra153 | |
| 8C5.K4H3.M4L.KNV (Genentech) | US 2015/0218276 | Heavy chain: Seq ID No. 129; Light chain: Seq ID No. 131 |
| 5H23_humanized (NGM) | U.S. Pat. No. 9,738,716 | Heavy chain: Seq ID No. 317; Light chain: Seq ID No. 319 |

TABLE 2B

KLB Binders-VH and VL sequences

| Binder | Chain | Sequence | SEQ ID NO: |
|---|---|---|---|
| 39F7 (Amgen) | VH | QVQLVESGGGVVQPGRSLRLSCAASGFTFSNYGIHWVRQA PGKGLEWVAVIWYDGSIKYYADSVKGRFTISRDNSKNTLYL QMNSLRAEDTAVYYCARDRAAAGLHYYYGMDVWGQGTTV TVSS | 26 |
| | VL | EIVLTQSPGTLSLSPGERATLSCRASQSVSSTYLAWYQQKP GQAPRLLIYGASSRATGIPDRFSGSGSGTDFTLTISRLEPED FAVYYCQQSGSSPLTFGGGTEVEIK | 27 |
| 5H23 (NGM) | VH (vH3) | QVQLQQSGAEVKKPGASVKVSCKASGYTFTSYDINWVRQA PGQGLEWIGWIYPGDGSTKYNEKFKGKATITRDTSASTAYM ELSSLRSEDTAVYFCARSDYYGSRSFAYWGQGTLVTVSS | 28 |
| | VL (vL2) | DIVMTQSPDSLAVSLGERATINCRASKSVSTSGYVYMHWYQ QKPGQPPKLLIYLASYLESGVPDRFSGSGSGTDFTLTISSVQ AEDVAVYYCQHSRDLTFPFGGGTKLEIK | 29 |

20

TABLE 3A

FGFR1c Binders

| Name | Epitope | Reference | Sequence in Patent Reference |
|---|---|---|---|
| YW182.5_YGDY (Genentech) | loop D2 | US 2015/0218276 | Heavy chain: Seq ID No. 133; Light chain: Seq ID No. 135 |
| R1Mab1 (Genentech) | loop D2 | U.S. Pat. No. 9,085,626 | Heavy chain: Seq ID No. 2; Light chain: Seq ID No. 6 |
| R1Mab2 (Genentech) | loop D2 | U.S. Pat. No. 9,085,626 | Heavy chain: Seq ID No. 3; Light chain: Seq ID No. 6 |
| R1Mab3 (Genentech) | loop D2 | U.S. Pat. No. 9,085,626 | Heavy chain: Seq ID No. 4; Light chain: Seq ID No. 6 |
| FR1-H7 (ImClone/Eli Lilly) | loop D2 | U.S. Pat. No. 8,263,074 | Heavy chain: FIG. 1A; Light chain: FIG. 1B |
| FR1-A1 (ImClone/Eli Lilly) | loop D3 | U.S. Pat. No. 8,263,074 | Heavy chain: FIG. 2A; Light chain: FIG. 2B |

TABLE 3B

FGFR1c Binders-VH and VL sequences

| Binder | Chain | Sequence | SEQ ID NO: |
|---|---|---|---|
| FR1-H7 (ImClone/Eli Lilly) | VH | EVQLVQSGAEVKKPGASVKVSCKVSGYTFTDYYMHWVQ QAPGKGLEWMGLVDPEDGETIYAEKFQGRVTITADTSTDT AYMELSSLRSEDTAVYYCARDDYMDVWGKGTLVTVSS | 30 |
| | VL | ETTLTQSPDTLSLSPGEGATLSCRASQSVSGSALAWYQQ KPGQAPRLLIYDASSRATGVPDRFSGSGSGADFSLTISRL EPEDFAVYSCQQYGSSPLTFGPGTKVDVK | 31 |
| FR1-A1 (ImClone/Eli Lilly) | VH | QVQLVQSGAEVKKPGSSVKVSCKASGQTFTGYYMHWVR QAPGQGLEWMGRIPILGIANYAQKFQGRVTITADKSTSTA YMELSSLRSEDTAVYYCARGGDLGGMDVWGQG | 32 |
| | VL | EIVLTQSPLSLPVTPGEPASISCRSSQSLRHSNGYNYLDW YLQKPGQSPQLLIYLASNRASGVPDRFSGSGSGTDFTLKI SRVEAEDVGVYYCMQALQIPPTFGPGTKVDK | 33 |
| R1Mab1 (Genentech) | VH | EVQLVESGGGLVQPGGSLRLSCAASGFTFTSTWISWVPG KGLEWVGEIDPYDGDTYYADSVKGRFTISADTSKNLQMN SLRAEDTAVYYCASSGYGGSDYAMDYWGQ | 34 |
| | VL | DIQMTQSPSSLSASVGDRVTITCRASQDVSTAVAWYQQK PGKAPKLLIYSASFLYSGVPSRFSGSGSGTDFTLTISSLQP EDFATYYCQQSYTTPPTFGQGTKWEIK | 35 |

TABLE 3B-continued

FGFR1c Binders-VH and VL sequences

| Binder | Chain | Sequence | SEQ ID NO: |
|---|---|---|---|
| R1Mab2 (Genentech) | VH | EVQLVESGGGLVQPGGSLRLSCAASGFTFSNNYIHWVPG KGLEWVADIYPNDGDTDYADSVKGRFTISADTSKNLQMN SLRAEDTAVYYCAREHFDAWVHYYVMDYWGQ | 36 |
| | VL | DIQMTQSPSSLSASVGDRVTITCRASQDVSTAVAWYQQK PGKAPKLLIYSASFLYSGVPSRFSGSGSGTDFTLTISSLQP EDFATYYCQQSYTTPPTFGQGTKWEIK | 35 |
| R1Mab3 (Genentech) | VH | EVQLVESGGGLVQPGGSLRLSCAASGFTFTSNWISWVPG KGLEWVAEIDPYDGATDYADSVKGRFTISADTSKNLQMNS LRAEDTAVYYCATGTDWMDYWGQ | 37 |
| | VL | DIQMTQSPSSLSASVGDRVTITCRASQDVSTAVAWYQQK PGKAPKLLIYSASFLYSGVPSRFSGSGSGTDFTLTISSLQP EDFATYYCQQSYTTPPTFGQGTKWEIK | 35 |

6.3.2. FGFR3-APLP2 Binders

MBMs of the disclosure can in some embodiments contain one of more ABSs that bind to human FGFR3 and one or more ABSs that bind to human APLP2. FGFR3 is a clinically validated onco-driver in bladder cancer. APLP2 has been identified as a cell surface receptor that can undergo rapid internalization and degradation. To induce both FGFR3 blockade and enhanced downregulation of FGFR3 via APLP2, an MBM of the disclosure can have one or more ABSs that bind to human FGFR3 and one or more ABSs that bind to human APLP2. In one exemplary configuration of this target pair, ABS2 and ABS3 bind to the same epitope of FGFR3 and ABS1 binds to APLP2. Without being bound by theory, it is believed that the binding of an MBM having this configuration results in blockade and/or degradation of the FGFR3 receptor complex.

Exemplary anti-FGFR3 antibody sequences are provided in Table 4. A MBM of the disclosure can include, for example, CDR or VH and/or VL sequences of any of the anti-FGFR3 antibodies provided in Table 4. Exemplary anti-APLP2 antibodies are provided in Table 5. A MBM of the disclosure can include, for example, CDR or VH and/or VL sequences of any of the anti-APLP2 antibodies provided in Table 5.

TABLE 4

FGFR3 Binders

| Binder | Chain | Sequence | SEQ ID NO: |
|---|---|---|---|
| V ofatamab (Rainier) | HC | EVQLVESGGGLVQPGGSLRLSCAASGFTFTSTGISWVR QAPGKGLEWVGRIYPTSGSTNYADSVKGRFTISADTSK NTAYLQMNSLRAEDTAVYYCARTYGIYDLYVDYTEYVM DYWGQGTLVTVSSASTKGPSVFPLAPSSKSTSGGTAAL GCLVKDYFPEPVTVSWNSGALTSGVHTFPAVLQSSGLY SLSSVVTVPSSSLGTQTYICNVNHKPSNTKVDKKVEPKS CDKTHTCPPCPAPELLGGPSVFLFPPKPKDTLMISRTPE VTCVVVDVSHEDPEVKFNWYVDGVEVHNAKTKPREEQ YNSTYRVVSVLTVLHQDWLNGKEYKCKVSNKALPAPIEK TISKAKGQPREPQVYTLPPSRDELTKNQVSLTCLVKGFY PSDIAVEWESNGQPENNYKTTPPVLDSDGSFFLYSKLTV DKSRWQQGNVFSCSVMHEALHNHYTQKSLSLSPGK | 38 |
| | LC | DIQMTQSPSSLSASVGDRVTITCRASQDVDTSLAWYKQ KPGKAPKLLIYSASFLYSGVPSRFSGSGSGTDFTLTISSL QPEDFATYYCQQSTGHPQTFGQGTKVEIKRTVAAPSVFI FPPSDEQLKSGTASVVCLLNNFYPREAKVQWKVDNALQ SGNSQESVTEQDSKDSTYSLSSTLTLSKADYEKHKVYA CEVTHQGLSSPVTKSFNRGEC | 39 |
| IMC-D11 (Eli Lilly/ImClone) | VH | EVQLVQSGAEVKKPGASVKVSCKASGYMFTSYGISWVR QAPGQGLEWMGWVSTYNGDTNYAQKFQGRVTVTTDT STSTAYMELRSLRSEDTAVYYCAR VLGYYDSIDGYYYGMDVWGQGTTVTVSS | 40 |
| | VL | QSVLTQPPSLSVAPGKTATFTCGGNNIGDKSVHWYRQK PGQAPVLVMYLDTERPSGIPERMSGSNFGNTATLTITRV EAGDEADYYCQVWDSGSDHWFGGGTKLTVLG | 41 |

TABLE 4-continued

FGFR3 Binders

| Binder | Chain | Sequence | SEQ ID NO: |
|---|---|---|---|
| H4xH21362 P2 (Regeneron) | VH | EVQLVESGGGLVQPGGSLRLSCAASGFTFSTYVMSWVR QAPGKGPEWVSGISGRTGTTYYADSVKGRFTISRDNSKN TLYLQMNSLRAEDTAVYYCASRITAAGRGYYYYYGMDV WGRGTTVTVSS | 42 |
| | VL | DIQMTQSPSSLSASVGDRVTITCRASQSISSYLNWYQQK PGKAPKLLIYAASSLQSGVPSRFSGSGSGTDFTLTISSLQ PEDFATYYCQQSYSTPPITFGQGTRLEIK | 43 |
| H4xH21387 P2 (Regeneron) | VH | EVQLVESGGGLVQPGRSLRLSCVASGFTFADYAMHWVR QAPGKGLEWVSGISWNSGNIDYADSVKGRFTISRDNAKN SLYLQMNSLRTEDTALYYCAKVRIVVAGYYYYYGMDVW GQGTTVTVSS | 44 |
| | VL | DIQMTQSPSSLSASVGDRVTITCRASQSISSYLNWYQQK PGKAPKLLIYAASSLQSGVPSRFSGSGSGTDFTLTISSLQ PEDFATYYCQQSYSTPPITFGQGTRLEIK | 43 |
| H4xH21371 P2 (Regeneron) | VH | QVQLVQSGVEVKKPGASVKVSCKASGYTFTDYGISWVR QAPGQGLEWMGWISAHNGNTNYAQKLQGRVTMTTDTS TNTAYMELRSLRSDDTAVYYCARRNWKYFDYWGQGTLV TVSS | 45 |
| | VL | DIQMTQSPSSLSASVGDRVTITCRASQSISSYLNWYQQK PGKAPKLLIYAASSLQSGVPSRFSGSGSGTDFTLTISSLQ PEDFATYYCQQSYSTPPITFGQGTRLEIK | 43 |

6.3.3. FGFR3-CD63 Binders

MBMs of the disclosure can in some embodiments contain one of more ABSs that bind to human FGFR3 and one or more ABSs that bind to human CD63. FGFR3 is a clinically validated onco-driver in bladder cancer. CD63 is ubiquitously expressed cell-surface tetraspanin that can regulate the trafficking of associated partners. To induce both FGFR3 blockade and enhanced downregulation or surface retention of FGFR3 via CD63, an MBM of the disclosure can have one or more ABSs that bind to human FGFR3 and one or more ABSs that bind to human CD63. In one exemplary configuration of this target pair, ABS2 and ABS3 bind to the same epitope of FGFR3 and ABS1 binds to CD63. Without being bound by theory, it is believed that the binding of an MBM having this configuration results in blockade and/or degradation of the FGFR3 receptor complex.

Exemplary anti-FGFR3 antibody sequences are provided in Table 4, above. A MBM of the disclosure can include, for example, CDR or VH and/or VL sequences of any of the anti-FGFR3 antibodies provided in Table 4. VH and VL sequences of exemplary anti-CD63 antibodies that can be used in the MBMs of the disclosure are provided in Table 6. A MBM of the disclosure can include, for example, CDR or VH and/or VL sequences of any of the anti-CD3 antibodies provided in Table 6.

TABLE 6

CD63 Binders-VH and VL sequences

| Binder | Chain | Sequence | SEQ ID NO: |
|---|---|---|---|
| H5C6 | VH | EVKLVESGGGLVQPGGSLKLSCATSGFTFSDYYMSWVR QTPEKRLEWVAYISSSGGSTYYSDTVKGQFTISRDNAKN TLYLQMSRLKSEDTAMYYCARREDYDGRLTYWGQGTLV TISA | 46 |
| | VL | DIVLTQSPASLAVSLGQRATISCRASKSVSTSGYSYMNW YQQKPGQPPKVLIYLASKLESGVPARFSGSGSGTDFTLNI HPVEEEDAATYYCQHSRELPYTFGGGTKLEIK | 47 |
| NVG-2 | VH | EVQLVESGGGLVQPGKSLKLTCATSGLTFNTAVVMHWVR QSPDKRLEWIGRIKDKSNNYAADYVESVRGRFTISRDDS KSSIYLQMNSLKEEDSATYFCFHNSLAYWGQGTMVTVSS | 48 |
| | VL | NIVMTQSPKSMSISVGDRVTMNCKASQNVDNSIAWYQQ KPGQSPKLLIYYATNRYTGVPDRFTGGGFGTDFTLTISSV QPEDAASYYCQRIYDCPNTFGGGTKLELK | 49 |
| H1M 12451N (Regeneron) | VH | QVQLQESGPGLMKPSETLSLTCTVSGGSFSSYYWNWIR QSPGKGLEWIGYIRYSGDTNYKPSLKSRFTISIDTSKNLFS LRLKSVTAADTAVYYCARMGLGSDAFDIWGQGTMVTVS S | 50 |
| | VL | EIVLTQSPGTLSLSPGERATLSCRASQSVNNNYLAWYQQ KPGQAPRLLIYGVFNRATNIPDRFSGSGSGTDFTLTISRL EPEDFAVYYCQQYGSSPVVTFGQGTKVEIK | 51 |

TABLE 6-continued

CD63 Binders-VH and VL sequences

| Binder | Chain | Sequence | SEQ ID NO: |
|---|---|---|---|
| H2M 12395N (Regeneron) | VH | QVQLQESGPRLVKPSETLSLTCIVSGGSISNFYWNWIRQ SPGKGLEWIGYFFYTGTIDYNPSLKSRVTISLDTSKNQFS LNLRLLTAADAAVYYCARMGLGANAFDIWGHGTMVTVSS | 52 |
| | VL | EIVLTQSPGTLSLSPGERATLSCRASQHVSSNYLAWYQQ KPGQAPRLLIYGGSSRATGIPDRFSGSGSGTDFTLTISRL EPADFAVFYCQQYGNSPVVTFGQGTKVEMK | 53 |
| H4H 12450N (Regeneron) | VH | QVQLQESGPKVVKPSETLSLTCTVSGGSISSYYWNWIRQ SPGKGLEWIGYTKRGYTDYNPSLRSRVTISEDTSKNQFS LRISSVTAADTAVYYCAQMGWGSHAFDMWGQGTMVAV SS | 54 |
| | VL | EIVLTQSPGTLSLSPGERATLSCRASQSVSSSYLAWYQQ KPGQAPRLLIYGASSRATGIPDRFSGSGSGTDFTLTISRL EPEDFAVYYCQQYGSSPVVTFGQGTKVEIK | 55 |
| H2M 12450N (Regeneron) | VH | QVQLQESGPKVVKPSETLSLTCTVSGGSISSYYWNWIRQ SPGKGLEWIGYTKRGYTDYNPSLRSRVTISEDTSKNQFS LRISSVTAADTAVYYCAQMGWGSHAFDMWGQGTMVAV SS | 54 |
| | VL | EIVLTQSPGTLSLSPGERATLSCRASQSVNSRYLAWYQQ KPGQAPRLLIYGASSRATGIPDRCSGSGSGTDFTLTISRL EPEDFAVYYCQQYGSSPVVTFGQGTKVEIK | 56 |

6.4. Antibody Drug Conjugates

The MBMs of the disclosure can be conjugated, e.g., via a linker, to a drug moiety, particularly where the MBM is intended for use as a cancer therapeutic. Such conjugates are referred to herein as antibody-drug conjugates (or "ADCs") for convenience.

In certain aspects, the drug moiety exerts a cytotoxic or cytostatic activity. In one embodiment, the drug moiety is chosen from a maytansinoid, a kinesin-like protein KIF11 inhibitor, a V-ATPase (vacuolar-type H+-ATPase) inhibitor, a pro-apoptotic agent, a Bcl2 (B-cell lymphoma 2) inhibitor, an MCL1 (myeloid cell leukemia 1) inhibitor, a HSP90 (heat shock protein 90) inhibitor, an IAP (inhibitor of apoptosis) inhibitor, an mTOR (mechanistic target of rapamycin) inhibitor, a microtubule stabilizer, a microtubule destabilizer, an auristatin, a dolastatin, a MetAP (methionine aminopeptidase), a CRM1 (chromosomal maintenance 1) inhibitor, a DPPIV (dipeptidyl peptidase IV) inhibitor, a proteasome inhibitor, an inhibitor of a phosphoryl transfer reaction in mitochondria, a protein synthesis inhibitor, a kinase inhibitor, a CDK2 (cyclin-dependent kinase 2) inhibitor, a CDK9 (cyclin-dependent kinase 9) inhibitor, a kinesin inhibitor, an HDAC (histone deacetylase) inhibitor, a DNA damaging agent, a DNA alkylating agent, a DNA intercalator, a DNA minor groove binder, a RNA polymerase inhibitor, a topoisomerase inhibitor, or a DHFR (di hydrofolate reductase) inhibitor.

In some embodiments, the cytotoxic agent is a maytansinoid having the structure:

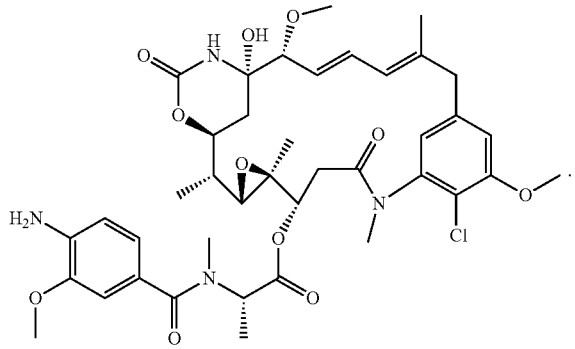 [SMILES: COc1cc(C(=O)N(C)[C@@H](C)C(=O)O[C@H]2CC(=O)N(C)c3cc(cc(OC)c3Cl)C/C(C)=C/C=C/[C@@H](OC)[C@@]3(O)C[C@H](OC(=O)N3)[C@@H](C)[C@@H]3O[C@@]23C)ccc1N]

In some embodiments, the cytotoxic agent is a maytansinoid having the structure:

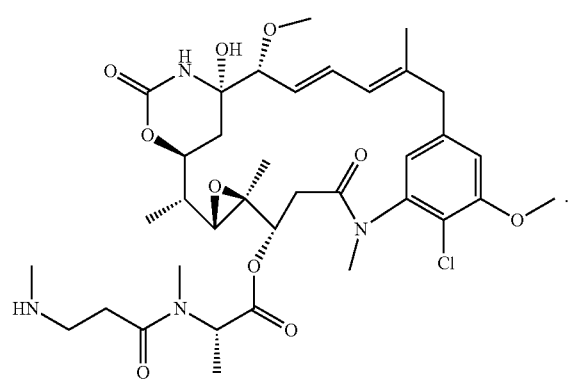 [SMILES: CNCCC(=O)N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

In some embodiments, the ADC comprises an MBM of the disclosure and

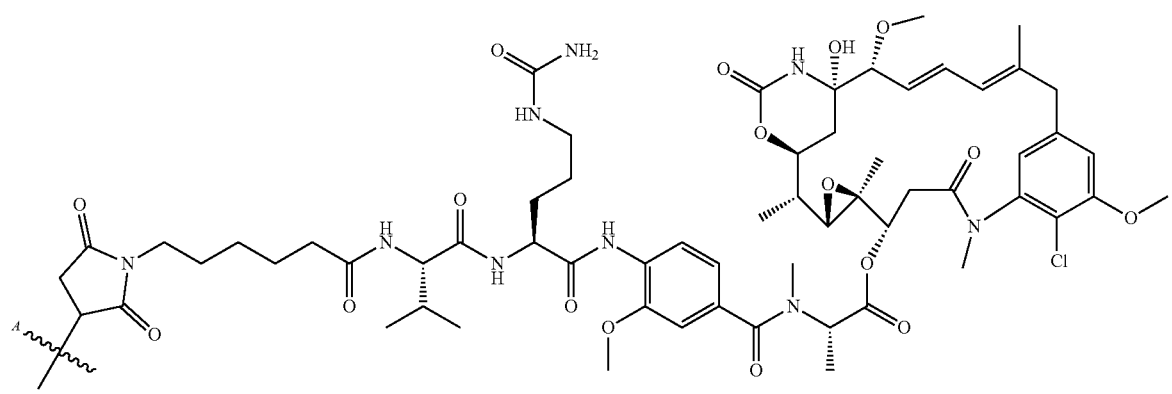
wherein
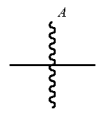
is a bond to the MBM.
In some embodiments, the antibody-drug conjugate comprises an MBM of the disclosure, and
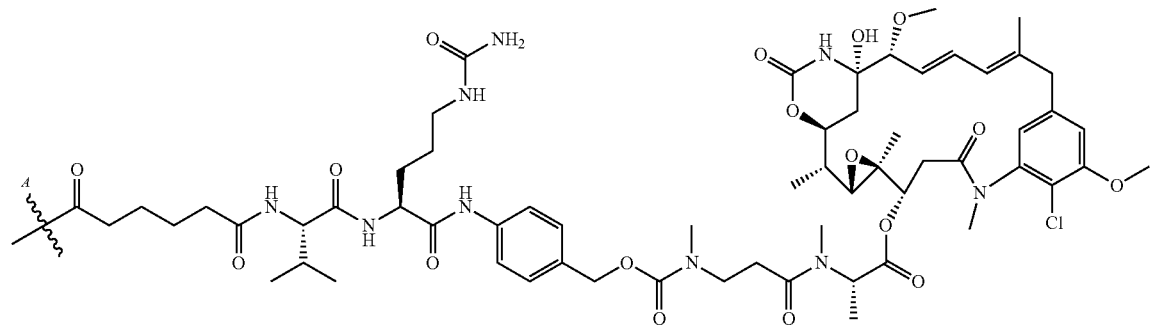
wherein
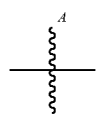
is a bond to the MBM.
In some embodiments, the ADC comprises an MBM of the disclosure and

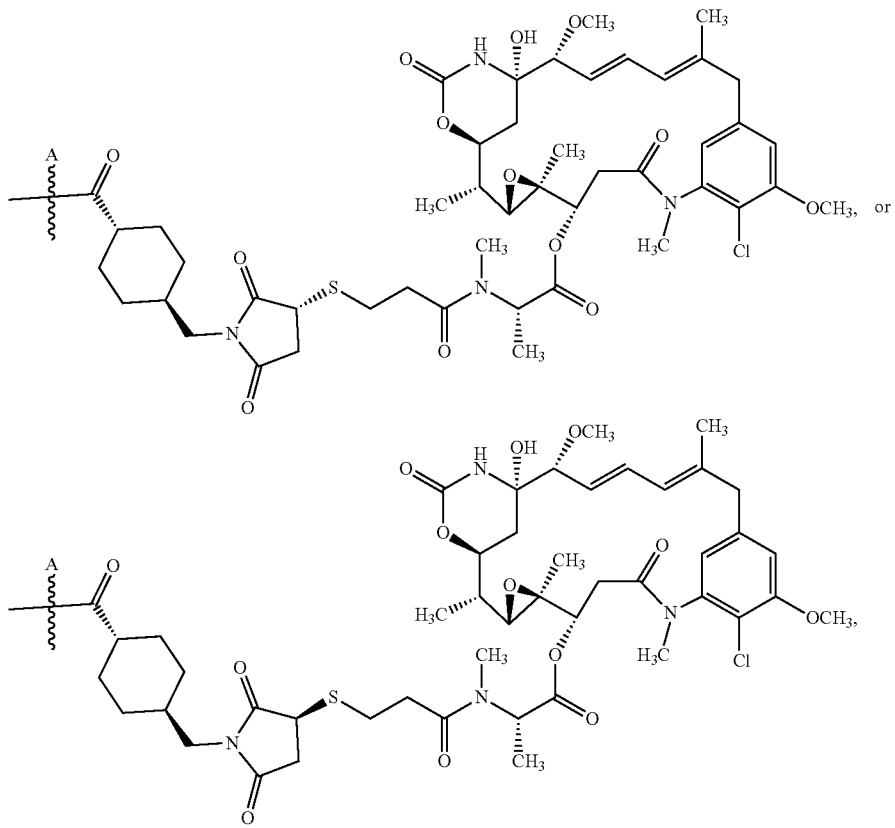

or
a mixture thereof,
wherein

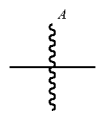

is a bond to the MBM of the disclosure.

In some embodiments, the bond is linked to the MBM via a sulfur constituent of a cysteine residue.

In some embodiments, the bond is linked the MBM via a nitrogen constituent of a lysine residue.

In the ADCs of the disclosure, the cytotoxic and/or cytostatic agents are linked to the MBM by way of ADC linkers. The ADC linker linking a cytotoxic and/or cytostatic agent to the MBM of an ADC may be short, long, hydrophobic, hydrophilic, flexible or rigid, or may be composed of segments that each independently have one or more of the above-mentioned properties such that the linker may include segments having different properties. The linkers may be polyvalent such that they covalently link more than one agent to a single site on the MBM, or monovalent such that covalently they link a single agent to a single site on the MBM.

In certain aspects, the linker is chosen from a cleavable linker, a non-cleavable linker, a hydrophilic linker, a procharged linker, or a dicarboxylic acid based linker.

As will be appreciated by skilled artisans, the ADC linkers link cytotoxic and/or cytostatic agents to the MBM by forming a covalent linkage to the cytotoxic and/or cytostatic agent at one location and a covalent linkage to the MBM at another. The covalent linkages are formed by reaction between functional groups on the ADC linker and functional groups on the agents and MBM.

The ADC linkers are preferably, but need not be, chemically stable to conditions outside the cell, and may be designed to cleave, immolate and/or otherwise specifically degrade inside the cell. Alternatively, ADC linkers that are not designed to specifically cleave or degrade inside the cell may be used. Choice of stable versus unstable ADC linker may depend upon the toxicity of the cytotoxic and/or cytostatic agent. For agents that are toxic to normal cells, stable linkers are preferred. Agents that are selective or targeted and have lower toxicity to normal cells may utilize, chemical stability of the ADC linker to the extracellular milieu is less important. A wide variety of ADC linkers useful for linking drugs to MBMs in the context of ADCs are known in the art. Any of these ADC linkers, as well as other ADC linkers, may be used to link the cytotoxic and/or cytostatic agents to the MBM of the ADCs of the disclosure.

Exemplary polyvalent ADC linkers that may be used to link many cytotoxic and/or cytostatic agents to a single MBM molecule are described, for example, in WO 2009/073445; WO 2010/068795; WO 2010/138719; WO 2011/120053; WO 2011/171020; WO 2013/096901; WO 2014/008375; WO 2014/093379; WO 2014/093394; WO 2014/093640, the contents of which are incorporated herein by reference in their entireties. For example, the Fleximer linker technology developed by Mersana et al. has the potential to enable high-DAR ADCs with good physicochemical properties. The Mersana technology is based on incorporating drug molecules into a solubilizing poly-acetal backbone via a sequence of ester bonds. The methodology renders highly-loaded ADCs (DAR up to 20) while maintaining good physicochemical properties.

Exemplary monovalent ADC linkers that may be used are described, for example, in Nolting, 2013, Antibody-Drug Conjugates, Methods in Molecular Biology 1045:71-100; Ducry et al., 2010, Bioconjugate Chem. 21:5-13; Zhao et al., 2011, J. Med. Chem. 54:3606-3623; U.S. Pat. Nos. 7,223,837; 8,568,728; 8,535,678; and WO2004010957, each of which is incorporated herein by reference.

By way of example and not limitation, some cleavable and noncleavable ADC linkers that may be included in the ADCs of the disclosure are described below.

In certain embodiments, the ADC linker selected is cleavable in vivo. Cleavable ADC linkers may include chemically or enzymatically unstable or degradable linkages. Cleavable ADC linkers generally rely on processes inside the cell to liberate the drug, such as reduction in the cytoplasm, exposure to acidic conditions in the lysosome, or cleavage by specific proteases or other enzymes within the cell. Cleavable ADC linkers generally incorporate one or more chemical bonds that are either chemically or enzymatically cleavable while the remainder of the ADC linker is noncleavable. In certain embodiments, an ADC linker comprises a chemically labile group such as hydrazone and/or disulfide groups. Linkers comprising chemically labile groups exploit differential properties between the plasma and some cytoplasmic compartments. The intracellular conditions to facilitate drug release for hydrazone containing ADC linkers are the acidic environment of endosomes and lysosomes, while the disulfide containing ADC linkers are reduced in the cytosol, which contains high thiol concentrations, e.g., glutathione. In certain embodiments, the plasma stability of an ADC linker comprising a chemically labile group may be increased by introducing steric hindrance using substituents near the chemically labile group.

Cleavable ADC linkers may include noncleavable portions or segments, and/or cleavable segments or portions may be included in an otherwise non-cleavable ADC linker to render it cleavable. By way of example only, polyethylene glycol (PEG) and related polymers may include cleavable groups in the polymer backbone. For example, a polyethylene glycol or polymer ADC linker may include one or more cleavable groups such as a disulfide, a hydrazone or a dipeptide.

Other degradable linkages that may be included in ADC linkers include ester linkages formed by the reaction of PEG carboxylic acids or activated PEG carboxylic acids with alcohol groups on a biologically active agent, wherein such ester groups generally hydrolyze under physiological conditions to release the biologically active agent. Hydrolytically degradable linkages include, but are not limited to, carbonate linkages; imine linkages resulting from reaction of an amine and an aldehyde; phosphate ester linkages formed by reacting an alcohol with a phosphate group; acetal linkages that are the reaction product of an aldehyde and an alcohol; orthoester linkages that are the reaction product of a formate and an alcohol; and oligonucleotide linkages formed by a phosphoramidite group, including but not limited to, at the end of a polymer, and a 5' hydroxyl group of an oligonucleotide.

In certain embodiments, the ADC linker comprises an enzymatically cleavable peptide moiety, for example a tripeptide or a dipeptide. In particular embodiments, the dipeptide is selected from: Val-Cit; Cit-Val; Ala-Ala; Ala-Cit; Cit-Ala; Asn-Cit; Cit-Asn; Cit-Cit; Val-Glu; Glu-Val; Ser-Cit; Cit-Ser; Lys-Cit; Cit-Lys; Asp-Cit; Cit-Asp; Ala-Val; Val-Ala; Phe-Lys; Val-Lys; Ala-Lys; Phe-Cit; Leu-Cit; Ile-Cit; Phe-Arg; and Trp-Cit. In certain embodiments, the dipeptide is selected from: Cit-Val; and Ala-Val.

In any of the various embodiments of the ADCs discussed above or herein, the ADCs can have a drug:antibody ratio (or, in this instance, a drug:MBM ratio), of 1 to 20, more typically in the range of 2 to 10.

6.5. Nucleic Acids and Host Cells

In another aspect, the disclosure provides nucleic acids encoding the MBMs of the disclosure. In some embodiments, the MBMs are encoded by a single nucleic acid. In other embodiments, the MBMs are encoded by a plurality (e.g., two, three, four or more) nucleic acids.

A single nucleic acid can encode a MBM that comprises a single polypeptide chain, a MBM that comprises two or more polypeptide chains, or a portion of a MBM that comprises more than two polypeptide chains (for example, a single nucleic acid can encode two polypeptide chains of a MBM comprising three, four or more polypeptide chains, or three polypeptide chains of a MBM comprising four or more polypeptide chains). For separate control of expression, the open reading frames encoding two or more polypeptide chains can be under the control of separate transcriptional regulatory elements (e.g., promoters and/or enhancers). The open reading frames encoding two or more polypeptides can also be controlled by the same transcriptional regulatory elements, and separated by internal ribosome entry site (IRES) sequences allowing for translation into separate polypeptides.

In some embodiments, a MBM comprising two or more polypeptide chains is encoded by two or more nucleic acids. The number of nucleic acids encoding a MBM can be equal to or less than the number of polypeptide chains in the MBM (for example, when more than one polypeptide chains are encoded by a single nucleic acid).

The nucleic acids of the disclosure can be DNA or RNA (e.g., mRNA).

In another aspect, the disclosure provides host cells and vectors containing the nucleic acids of the disclosure. The nucleic acids may be present in a single vector or separate vectors present in the same host cell or separate host cell, as described in more detail herein below.

6.5.1. Vectors

The disclosure provides vectors comprising nucleotide sequences encoding a MBM or a MBM component described herein, for example one or two of the polypeptide chains of a half antibody. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes can be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by co-transformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors can be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. Methods and conditions for culturing the resulting transfected cells and for recovering the expressed polypeptides are known to those skilled in the art, and may be varied or optimized depending upon the specific expression vector and mammalian host cell employed, based upon the present description.

6.5.2. Cells

The disclosure also provides host cells comprising a nucleic acid of the disclosure.

In one embodiment, the host cells are genetically engineered to comprise one or more nucleic acids described herein.

In one embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The disclosure also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

6.6. Pharmaceutical Compositions

The MBMs and/or ADCs of the disclosure may be in the form of compositions comprising the MBM and/or ADC and one or more carriers, excipients and/or diluents. The compositions may be formulated for specific uses, such as for veterinary uses or pharmaceutical uses in humans. The form of the composition (e.g., dry powder, liquid formulation, etc.) and the excipients, diluents and/or carriers used will depend upon the intended uses of the MBM and/or ADC and, for therapeutic uses, the mode of administration.

For therapeutic uses, the compositions may be supplied as part of a sterile, pharmaceutical composition that includes a pharmaceutically acceptable carrier. This composition can be in any suitable form (depending upon the desired method of administering it to a patient). The pharmaceutical composition can be administered to a patient by a variety of routes such as orally, transdermally, subcutaneously, intranasally, intravenously, intramuscularly, intratumorally, intrathecally, topically or locally. The most suitable route for administration in any given case will depend on the particular antibody and/or ADC, the subject, and the nature and severity of the disease and the physical condition of the subject. Typically, the pharmaceutical composition will be administered intravenously or subcutaneously.

Pharmaceutical compositions can be conveniently presented in unit dosage forms containing a predetermined amount of an MBM and/or ADC of the disclosure per dose. The quantity of MBM and/or ADC included in a unit dose will depend on the disease being treated, as well as other factors as are well known in the art. Such unit dosages may be in the form of a lyophilized dry powder containing an amount of MBM and/or ADC suitable for a single administration, or in the form of a liquid. Dry powder unit dosage forms may be packaged in a kit with a syringe, a suitable quantity of diluent and/or other components useful for administration. Unit dosages in liquid form may be conveniently supplied in the form of a syringe pre-filled with a quantity of MBM and/or ADC suitable for a single administration.

The pharmaceutical compositions may also be supplied in bulk from containing quantities of ADC suitable for multiple administrations.

Pharmaceutical compositions may be prepared for storage as lyophilized formulations or aqueous solutions by mixing an MBM and/or ADC having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives should be nontoxic to the recipients at the dosages and concentrations employed.

Buffering agents help to maintain the pH in the range which approximates physiological conditions. They may be present at a wide variety of concentrations, but will typically be present in concentrations ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives may be added to retard microbial growth, and can be added in amounts ranging from about 0.2%-1% (w/v). Suitable preservatives for use with the present disclosure include phenol, benzyl alcohol, meta-cresol, methyl paraben, propyl paraben, octadecyldimethylbenzyl ammonium chloride, benzalkonium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, a-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trehalose; and trisaccacharides such as raffinose; and polysaccharides such as dextran. Stabilizers may be present in amounts ranging from 0.5 to 10 wt % per wt of ADC.

Non-ionic surfactants or detergents (also known as "wetting agents") may be added to help solubilize the glycoprotein as well as to protect the glycoprotein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), and pluronic polyols. Non-ionic surfactants may be present in a range of about 0.05 mg/mL to about 1.0 mg/mL, for example about 0.07 mg/mL to about 0.2 mg/mL.

Additional miscellaneous excipients include bulking agents (e.g., starch), chelating agents (e.g., EDTA), antioxidants (e.g., ascorbic acid, methionine, vitamin E), and cosolvents.

6.7. Therapeutic Indications

The MBMs, ADCs, and pharmaceutical compositions of the disclosure can be used for treating cancer, for example a cancer associated with expression of the target molecules to which ABS1, ABS2, and ABS3 bind.

Thus, in one aspect, the disclosure provides a method of treating cancer comprising administering to a subject suffering from cancer an effective amount of an MBM, conjugate, or pharmaceutical composition of the disclosure. In particular embodiments, MBMs of the disclosure binding FGFR3, and optionally binding CD63 or binding APLP2, can be used to treat bladder cancer, glioblastoma, and squamous cell lung carcinoma.

The MBMs, ADCs, and pharmaceutical compositions of the disclosure can also be used for non-cancer indications, for example, for treating nonalcoholic steatohepatitis ("NASH"), treating metabolic disease, reducing circulating HDL cholesterol, increasing circulating LDL cholesterol, reducing blood triglycerides, reducing blood glucose, treating obesity, and treating diabetes. For such non-cancer indications, in some embodiments the MBMs target KLB and/or FGFR1c.

Thus, in one aspect, the disclosure provides a method of reducing circulating HDL cholesterol comprising administering to a subject suffering from elevated HDL levels an effective amount of an MBM, conjugate, or pharmaceutical composition of the disclosure.

In another aspect, the disclosure provides a method of increasing circulating LDL cholesterol comprising administering to a subject suffering from low LDL levels an effective amount of an MBM, conjugate, or pharmaceutical composition of the disclosure.

In another aspect, the disclosure provides a method of reducing blood triglycerides comprising administering to a subject suffering from elevated triglyceride levels an effective amount of an MBM, conjugate, or pharmaceutical composition of the disclosure.

In another aspect, the disclosure provides a method of reducing blood glucose comprising administering to a subject suffering from suffering from elevated glucose levels an effective amount of an MBM, conjugate, or pharmaceutical composition of the disclosure.

In another aspect, the disclosure provides a method of treating obesity comprising administering to a subject suffering from obesity an effective amount of an MBM, conjugate, or pharmaceutical composition of the disclosure.

In another aspect, the disclosure provides a method of treating diabetes comprising administering to a subject suffering from diabetes an effective amount of an MBM, conjugate, or pharmaceutical composition of the disclosure.

7. EXAMPLES

7.1. Example 1: FGFR1c×KLB×KLB 2+1 N-scFv MBMs

7.1.1. Materials and Methods

7.1.1.1. Generation of MBMs

Various KLB scFvs binding to KLB epitope 1 (ep1) or epitope 2 (ep2) were fused to the N-terminus of a FGFR1c VH domain from an existing IgG-like bispecific molecule, REGN4366, targeting both FGFR1c and KLB (FIG. 1 and Table 7).

DNA fragments encoding (i) various KLB scFvs in the orientation of VL (with a 100C mutation, Kabat numbering), linker (4×$G_4S$ (SEQ ID NO: 57)), and VH (with a 44C mutation, Kabat numbering), followed by linkers of varied lengths for connecting the scFvs to a FGFR1c binding Fab, (ii) a FGFR1c binding Fab, and (iii) IgG1 Fc domains with knob-forming mutations (S354C, T366W, EU numbering), hole-forming mutations (Y349C, T366S, L368A, Y407V, EU numbering) and Star mutations (H435R, Y436F, EU numbering) were synthesized by Integrated DNA Technologies, Inc. (San Diego, California) or GenScript (Piscataway, NJ).

Mammalian expression vectors for individual heavy chains were created by either NEBuilder HiFi DNA Assembly Kit (New England BioLabs Inc.) or restriction digest followed by ligation following standard molecular cloning protocols provided by New England BioLabs Inc. For expression of FGFR1c/KLB/KLB 2+1 N-scFv MBMs (F1K-scFv1-9), heavy chains ("Hc1-Knob" and "Hc2-Hole*") and universal light chain DNAs were co-transfected into Expi293 cells (ThermoFisher Scientific) following the manufacturer's protocol. 50 ml of cell culture medium was harvested and processed for purification via a HiTrap Protein A FF column (GE Healthcare). For functional confirmation, selected MBMs were scaled up to 200 ml and subject to a series of purification procedures including size exclusion chromatography as the final step. REGN4366, with a Fab binding to KLB and a Fab binding to FGFR1c, was made and purified to serve as an IgG-like bispecific control molecule.

7.1.1.2. HEK293.SREluc.hFGFR1cHS/hKLB Reporter Based Assay

MBMs were tested for their agonist activities using HEK293.SREluc.hFGFR1cHS/hKLB cells that stably expressed human FGFR1c and KLB as well as a luciferase reporter gene under the control of a promoter containing serum responsive elements (SRE). Recombinant human FGF21 with 6×His tag (SEQ ID NO: 58) was used as a positive control, with the maximum reporter activity obtained from FGF21 defined as 100% activity. Cells were treated with each MBM or 6×His-FGF21 for 6 hours, and then subjected to luciferase assays. The percent activity induced by individual MBMs was normalized against the maximum activity by FGF21. Dose-response assays were performed to determine EC50.

7.1.1.3. Biacore Analysis on hFGFR1c and hKLB Binding

Affinity and mechanism of action of binding for F1K-scFv6 was determined by Biacore analysis. In order to compare the apparent affinity of F1K-scFv6 for KLB with the monovalent affinity of the parental KLB mAbs, antibody capture format was used. In brief, FGFR1c parental mAb 19842, KLB parental mAbs 22532P2 and 22393P2, FGFR1c/KLB parental bispecific antibody REGN4366 and F1K-scFv6 were immobilized on a CM5 chip with an anti-human Fc antibody (REGN2567). Different concentrations of hFGFR1c_V5_6×His (800-12.5 nM, 4-fold dilution) or hKLB.HA.6×His (100-1.56 nM, 4-fold dilution) were injected at 50 μL/min for 2 min and the assay was performed at 25° C. Binding kinetics parameters were measured by fitting the real time data using 1:1 binding model using Scrubber 2.0c.

7.1.1.4. Cell Based Binding by Flow Cytometry

HEK293/Cas9-hFGFR1/hKLB (KLB$^+$), HEK293/hFGFR1c (hFGFR1c$^+$) and HEK293/hFGFR1c/hKLB (hFGFR1c$^+$/hKLB$^+$) cells were resuspended in complete Dulbecco's Modified Eagle Medium (DMEM) medium (10% Fetal Bovine Serum (FBS), 1× penstrep-glutamine) at 1×10$^6$ cells/mL and staining was performed in 1×10$^5$ cells. MBMs were added and cells were stained for 30 min at 2-8° C. The cells were washed twice with FACS wash buffer (Phosphate-Buffered Saline (PBS) with 1% FBS and 1 mM EDTA) and centrifuged at 1800 RPM for 4 min at 4° C. Allophycocyanin-conjugated goat anti-human IgG (Jackson Immuno Research, 109-136-098, 1:400) was added and incubated with the cells for 30 min at 2-8° C. Cells were washed as before and resuspended in 100 μL of 2% paraformaldehyde. Cells were incubated for 30 min at 2-8° C. and washed twice. Stained cells were analyzed using BD LSRFortessa™ FACS instrument.

7.1.2. Results

7.1.2.1. Generation of FGFR1c/KLB/KLB 2+1 N-scFv MBMs

Nine FGFR1c/KLB/KLB 2+1 N-scFv MBMs having the features shown in Table 7 were expressed and purified.

TABLE 7

| Molecule ID | Hc1-Knob | | | Hc2-Hole* | | Lc |
|---|---|---|---|---|---|---|
| | 1. KLB scFv | Linker | 2. FGFR1c | 3. KLB | | |
| F1K-scFv1 | 22414P2 (KLB ep1) | 3xG$_4$S | 19842 | 22393P2 (KLB ep1) | | Universal Lc |
| F1K-scFv2 | 22401P2 (KLB ep1) | (SEQ ID | | | | |
| F1K-scFv3 | 22532P2 (KLB ep2) | NO: 1) | | | | |
| F1K-scFv4 | 22414P2 (KLB ep1) | 6xG$_4$S | | | | |
| F1K-scFv5 | 22401P2 (KLB ep1) | (SEQ ID | | | | |
| F1K-scFv6 | 22532P2 (KLB ep2) | NO: 59) | | | | |
| F1K-scFv7 | 22414P2 (KLB ep1) | 9xG$_4$S | | | | |
| F1K-scFv8 | 22401P2 (KLB ep1) | (SEQ ID | | | | |
| F1K-scFv9 | 22532P2 (KLB ep2) | NO: 60) | | | | |

| Molecule ID | Hc1 | Hc2* | Lc |
|---|---|---|---|
| REGN4366 | Na | Na | 19842 | 22393P2 (KLB ep1) | Universal Lc | ep: epitope;
*star mutations

7.1.2.2. Epitope-Dependent Activity of FGFR1c/KLB/KLB 2+1 N-scFv Trispecific Molecules Results of the cell based reporter assay using HEK293.SREluc.hFGFR1cHS/hKLB to analyze the agonist activity of the purified FGFR1c/KLB/KLB 2+1 N-scFv MBMs are shown in Table 8. F1K_scFv3, F1K_scFv6 and F1K_scFv9 were found to be the top activators based on % activity. They all share the same KLB targeting scFv binding to KLB ep2 region, and were significantly more active in the assay than the MBMs having a scFv targeting the same KLB ep1 region as the original KLB Fab. Notably, F1K_scFv6 with an scFv-Fab linker of length 30 amino acid was observed to have the highest activity at 54.1% and the best potency (EC50=9.80E-10 M).

TABLE 8

Activation of reporter activity by 2 + 1
N-scFvs in HEK293.SREIuc.hFGFR1cHS/hKLB based assay

| Molecule ID | 1. KLB scFv | 2. FGFR1c | 3. KLB | % Activity of (FGF21) | EC50 (M) |
|---|---|---|---|---|---|
| REGN1945 | NA | NA | NA | ND | ND |
| 6xHis-hFGF21 | NA | NA | NA | 100 | 3.40E−09 |
| F1K_scFv1 | 22414P2 (KLB ep1) | 19842 | 22393P2 | 5 | 3.90E−09 |
| F1K_scFv2 | 22401P2 (KLB ep1) | 19842 | 22393P2 | 6.2 | 3.70E−08 |
| F1K_scFv3 | 22532P2 (KLB ep2) | 19842 | 22393P2 | 28.9 | 7.90E−09 |
| F1K_scFv4 | 22414P2 (KLB ep1) | 19842 | 22393P2 | 4.7 | 3.50E−09 |
| F1K_scFv5 | 22401P2 (KLB ep1) | 19842 | 22393P2 | 3 | 4.70E−08 |
| F1K_scFv6 | 22532P2 (KLB ep2) | 19842 | 22393P2 | 54.1 | 9.80E−10 |
| F1K_scFv7 | 22414P2 (KLB ep1) | 19842 | 22393P2 | 5.5 | 3.60E−09 |
| F1K_scFv8 | 22401P2 (KLB ep1) | 19842 | 22393P2 | 4.2 | 4.20E−08 |
| F1K_scFv9 | 22532P2 (KLB ep2) | 19842 | 22393P2 | 20.7 | 2.40E−09 |

% Activity represents relative maximum luciferase activity achieved by each molecule normalized to the value of 6xHis-FGF21.
ND: not detected

7.1.2.3. 2+1 N-scFv Trispecific F1K-scFv6 can Bind Simultaneously to Two Different Epitopes on the Same KLB Results of the Biacore analysis on F1K-scFv6 are shown in Tables 9A-9B. F1K-scFv6 was found to have a $K_D$ of 1.47E-11 M for hKLB, representing a 55- and 1,333-fold increase in affinity in comparison to the parental KLB mAbs 22532P2 and 22393P2, respectively. The enhanced affinity for hKLB was also observed when F1K-scFv6 was compared with REGN4366 (with 22393P2 arm for hKLB). This observation strongly supports the conclusion that F1K-scFv6, which possesses distinct epitope-targeting arms for KLB, can simultaneously engage both binding sites on the same hKLB molecule. For hFGFR1c binding, F1K-scFv6 has a slight decrease (4-fold) in affinity for hFGFR1c compared with its parental FGFR1c mAb 19842 or parental bispecific antibody REGN4366 (with 19842 arm for hFGFR1c).

TABLE 9A hFGFR1c 6xHis Binding Kinetics

| mAb Captured | Target | mAb Capture Level (RU) | 100 nM Antigen Bound (RU) | $k_a$ (1/Ms) | $k_d$ (1/s) | $K_D$ (M) |
|---|---|---|---|---|---|---|
| 19842 IgG | FGFR1c | 677 ± 2.3 | 107 | 4.93E+04 | 2.60E−02 | 5.27E−07 |
| 22532P2 IgG | KLB | 546 ± 1.6 | −8 | NB | NB | NB |
| 22393P2 IgG | KLB | 553 ± 1 | −6 | NB | NB | NB |
| REGN4366 | FGFR1c/KLB | 605 ± 1.6 | 50 | 4.59E+04 | 2.47E−02 | 5.39E−07 |
| F1K_scFv6 | FGFR1c/KLB/KLB | 649 ± 3.1 | 17 | 2.10E+04 | 4.43E−02 | 2.11E−06 |

TABLE 9B hKLB.HA.6xHis Binding Kinetics

| mAb Captured | Target | mAb Capture Level (RU) | 100 nM Antigen Bound (RU) | $k_a$ (1/Ms) | $k_d$ (1/s) | $K_D$ (M) |
|---|---|---|---|---|---|---|
| 19842 IgG | FGFR1c | 670 ± 2.2 | −8 | NB | NB | NB |
| 22532P2 IgG | KLB | 540 ± 1.6 | 480 | 1.46E+05 | 1.20E−04 | 8.23E−10 |
| 22393P2 IgG | KLB | 547 ± 2 | 688 | 5.98E+05 | 1.17E−02 | 1.96E−08 |
| REGN4366 | FGFR1c/KLB | 597 ± 2.4 | 411 | 4.76E+05 | 1.22E−02 | 2.55E−08 |
| F1K_scFv6 | FGFR1c/KLB/KLB | 639 ± 3.1 | 473 | 1.08E+06 | 1.59E−05 | 1.47E−11 |

7.1.2.4. 2+1 N-scFv Trispecific F1K-scFv6 Binds More Tightly to Cells Overexpressing hKLB and hFGFR1c/hKLB To further confirm the relevance of enhanced affinity of F1K-scFv6 for hKLB in cell based setting, FACS binding assay was used to compare the binding of trispecific F1K-scFv6 (FGFR1c/KLB/KLB) with bispecific antibodies REGN4366 (FGFR1c/KLB 22393 arm) and REGN6799 (FGFR1c/KLB 22532 arm), parental antibodies 22393 IgG (KLB), 22532 IgG (KLB) and 19842 IgG (FGFR1c). In both HEK293/Cas9-hFGFR1/hKLB (hFGFR1 knockout and hKLB over-expressing) and HEK293/hFGFR1c/hKLB (hFGFR1c and hKLB over-expressing) cells, F1K-scFv6 consistently demonstrated more potent EC50s in binding than all other controls (FIGS. 6A and 6C). In HEK293/hFGFR1c cells, with bivalency for hFGFR1c, 19842 IgG was observed to have the strongest binding, followed by REGN4366 and F1K-scFv6 (FIG. 6B). The FACS binding data is in good agreement with the Biacore analysis. Without being bound by theory, it is believed that the data of this Example shows that bi-epitopic engagement of hKLB via 2+1 N-scFv trispecific design improves antibody-mediated KLB/FGFR1c receptor complex interaction and potential cell surface clustering.

7.1.2.5. 2+1 N-scFv MBM F1K-scFv6 has Superior Agonist Activity than the Bispecific REGN4366

To evaluate if enhanced affinity of F1K-scFv6 could translate into improved efficacy over the bispecific REGN4366, in vitro reporter-based cell assay using HEK293.SREluc.hFGFR1cHS/hKLB was performed. Both F1K-scFv6 and REGN4366 were purified via size exclusion chromatography as the final step following affinity purification in order to remove any aggregation which could confound the interpretation of the data. In comparison to the parental bispecific antibody REGN4366, which has only 19% activation when normalized against soluble FGF21, F1K-scFv6 not only enhanced the potency (in EC50) of luciferase gene expression by 4-5 fold, but also significantly boosted the % of activation to 77% (FIG. 8).

A similar trivalent molecule using the same 22532P2 scFv, but fused to the C-terminus of Fc, termed as 2+1 C-scFv, was also made and evaluated. This corresponding trispecific molecule had much poorer expression and purification yield with inferior functional activity than F1K-scFv6 (results not shown).

7.2. Example 2: Evaluation of Linker Length on Trispecific Activity

7.2.1. Materials & Methods

HEK293.SREluc.hFGFR1c.hKLB stable cell line was generated by sequentially transfecting HEK293 cells with SRE-luciferase reporter, full length human FGFR1c, and full length human KLB plasmids.

Linker length variants of the trispecific molecule referred to as scFv6 were generated and tested in the luciferase reporter assay, as were control bispecific molecules. The linker variants are referred to as scFv6 LK7: $G_4S$ GG (SEQ ID NO:63), scFv6 LK15: $3\times G_4S$ (SEQ ID NO:1), scFv6 LK22: $4\times G_4S$ GG (SEQ ID NO:64), scFv6: $6\times G_4S$ (SEQ ID NO:59), scFv6 LK37: $7\times G_4S$ GG (SEQ ID NO:65), and scFv6 LK45: $9\times G_4S$ (SEQ ID NO:60).

The cells were plated in a 384-well plate, and cultured overnight in complete media containing 10% fetal bovine serum (FBS). The culture media was changed to Opti-MEM reduced serum medium (ThermoFisher, USA) supplemented with 0.1% FBS. Approximately 24 hr later, cells were treated with serially diluted ligands for 6 hr, and then subjected to luciferase assay using ONE-Glo™ Luciferase Assay System (Promega, USA), according to the manufacturer's instructions.

7.2.2. Results

In one study, the agonist activity of the bispecific binding molecules (BBMs) referred to as REGN4304 and REGN4366 was compared to that of hFGF21. In this assay, the BBMs showed approximately 30% of the agonist activity of hFGF21 (FIG. 7).

In another study, the agonist activity of linker length variants (of the peptide linker between the domains designated 2 and 3 in FIG. 9) was compared that of FGF21 and the BBM referred to as REGN4304. The results are shown in FIG. 9 and Table 10 below:

TABLE 10

|  | 1 | 2 | 3 | Linker | EC50 | % Act |
|---|---|---|---|---|---|---|
| REGN1438 |  | 6His-FGF21 |  |  | 5.7E-10 | 100.0 |
| F1K_scFv6 LK7 | 22393 | ADI-19842 | 22532 | L20H7 | 1.7E-09 | 104.5 |
| F1K_scFv6 LK15 | 22393 | ADI-19842 | 22532 | L20H15 | 1.6E-09 | 97.5 |
| F1K_scFv6 LK22 | 22393 | ADI-19842 | 22532 | L20H22 | 1.3E-09 | 87.9 |
| F1K_scFv6 LK30 | 22393 | ADI-19842 | 22532 | L20H30 | 2.0E-09 | 84.2 |
| F1K_scFv6 LK37 | 22393 | ADI-19842 | 22532 | L20H37 | 1.1E-09 | 80.4 |
| F1K_scFv6 LK45 | 22393 | ADI-19842 | 22532 | L20H45 | 1.5E-09 | 78.7 |
| REGN4304 |  |  |  |  | 1.8E-09 | 42.0 |

All linker length variants showed at least approximately 2× the activity of the control bispecific binding molecule, with those variants having the shortest linker lengths (7 or 15 amino acid) showing the greatest agonist activity.

7.3. Example 3: Activation of FGFR1c Signaling in HEK293 Cells

7.3.1. Materials & Methods

HEK293.SREluc.hFGFR1c.hKLB stable cell line was generated as described in Example 3. For western blot analysis, HEK293.SREluc.hFGFR1c.hKLB cells were plated in a 6-well plate, and cultured overnight in complete media containing 10% fetal bovine serum (FBS). The culture media was changed to Opti-MEM reduced serum medium (ThermoFisher, USA) supplemented with 0.1% FBS. Approximately 24 hr later, diluted ligands were added to the cells to final 1 nM or 10 nM concentrations. After a 15 minute treatment, cells were washed with cold PBS, and then lysed in RIPA lysis buffer (150 mMTris/HCl, pH 7.4, 50 mM NaCl, 1% NP-40 and 0.1% Tween 20). Total cell lysates were resolved by SDS-PAGE, and transferred onto PVDF membranes. For western blot analysis, the following primary antibodies were used: total ERK (Cell Signaling, 9102), phospho-ERK (Cell Signaling, 9101), PLC-gamma (Cell Signaling, 5690), phosphor-PLCgamma (Cell Signaling, 2821).

7.3.2. Results

The agonist activity of bispecific and trispecific binding molecules was tested in HEK293.SREluc.hFGFR1c.hKLB cells stably expressing human FGFR1c and human KLB, together with the irrelevant antibody REGN1945 as a negative control and FGF21 (REGN1438) as a positive control. Following treatment, ERK and PLC-gamma phosphorylation, which are induced by the activated FGFR1c, was measured as was luciferase activity.

Both F1K_scFv6LK7 and F1K_scFv6L1 strongly induced ERK and PLC-gamma phosphorylation at both 1 nM and 10 nM concentrations. Notably, phospho-ERK and phospho-PLC-gamma levels in F1K_scFv6 or F1K_scFv6LK7 treated cells were markedly higher than those in cells treated with corresponding concentrations of the parental bispecific antibody (REGN4366), an FGFR1/KLB agonist bispecific antibody (REGN4304), or recombinant human FGF21 (REGN1438) (FIG. 10A).

To assess the time course of FGFR1c activation, HEK293.SREluc.hFGFR1c.hKLB cells were treated with ligands for varying times, and harvested for western blot analysis. Results are shown in FIG. 10B. ERK activation measured by phospho-ERK levels was observed as early as 15 min following treatment with REGN1438, REGN4304, or F1K_scFv6, which persisted for up to 6 hours. F1K_scFv6 showed higher phospho-ERK levels compared with REGN1438 or REGN4304 throughout the time course of the treatment. F1K_scFv6 strongly induced phospho-PLCgamma at 15 min time point, which was then gradually decreased over time.

7.4. Example 4: Size Analysis of In Vitro Complexes Formed Between KLB, FGFR1c and Binding Molecules by Asymmetric Flow Field-Flow Fractionation Coupled to Multi-Angle Laser Light Scattering (A4F-MALLS)

7.4.1. Overview

In principle, the trispecific binding molecules of the disclosure can form different types of complexes with FGFR1c and KLB. To determine the types of complexes formed, size analysis of in vitro complexes formed between the 2+1 N-scFv and 2+1 N-Fab trispecific binding molecules was performed using asymmetric flow field-flow fractionation coupled to multi-angle light scattering (A4F-MALS). A4F-MALLS was also used to analyze complexes formed by a control bispecific binding molecule (REGN4304) and a monospecific KLB binding molecule (REGN4661).

7.4.2. Materials & Methods

7.4.2.1. A4F-MALLS Mobile Phase Buffer

The mobile phase buffer (10 mM sodium phosphate, 500 mM sodium chloride, pH 7.0±0.1) was prepared by combining 1.4 g sodium phosphate monobasic monohydrate, 10.7 g sodium phosphate dibasic heptahydrate, and 500 mL 5 M sodium chloride; the solution was then brought to a volume to 5.0 L with HPLC grade water. The final measured pH of the buffer was 7.0. The mobile phase buffer was filtered (0.2 µm) before use.

7.4.2.2. A4F-MALLS

The A4F-MALLS system was composed of an Eclipse™ 3+A4F Separation System coupled to an Agilent 1200 Series HPLC system equipped with an ultraviolet (UV) diode array detector, Wyatt Technology Dawn HELEOS® II laser light scattering instrument (LS), and an Optilab® T-rEX differential refractometer (RI) detector. The detectors were connected in series in the following order: UV-LS-RI. LS and RI detectors were calibrated according to instructions provided by Wyatt Technology.

Defined amounts of anti-KLB and anti-FGFR1c multi-specific binding molecule candidates were each combined with REGN6424 (recombinant KLB) and REGN6152 (recombinant FGFR1c) and diluted in 1×DPBS, pH 7.4 to yield the equimolar ratio: 0.2 µM multispecific binding molecule: 0.2 µM REGN REGN6424 or 0.2 µM multispecific binding molecule: 0.2 µM REGN REGN6424: 0.2 µM REGN REGN6152. All samples were incubated at ambient temperature for 2 hours and maintained unfiltered at 4° C. prior to injection into an Eclipse™ short channel fitted with a W350 spacer foil (350 µm spacer thickness, 2.2 cm spacer width) and using a 10 kDa MWCO regenerated cellulose membrane. The channel was pre-equilibrated with the mobile phase buffer (10 mM sodium phosphate, 500 mM sodium chloride, pH 7.0±0.1), prior to the injection of each sample. Bovine serum albumin (BSA; 2 mg/mL; 10 µg sample load) was injected separately and included as a system suitability control.

The fractionation method consisted of four steps: injection, focusing, elution, and a channel "wash-out" step. The A4F-MALLS mobile phase buffer (10 mM sodium phosphate, 500 mM sodium chloride, pH 7.0±0.1) was used throughout the fractionation method. Each sample (7 µg) was injected at a flow rate of 0.2 mL/min for 1 min and subsequently focused for 3 min with a focus flow rate of 1.0 mL/min. The sample was eluted with a channel flow rate of 1.0 mL/min with the constant cross flow 3.0 mL/min for 15 min, followed by linear gradient cross flow from 3.0 mL/min to 0 mL/min over 5 min. Finally, the cross flow was held at 0 mL/min for an additional 5 min to wash out the channel. BSA was fractionated using the same parameter settings.

7.4.2.3. MALLS Data Analysis

Data were analyzed using ASTRA V software (version 5.3.4.14, Wyatt Technology). The data were fit to the equation that relates the excess scattered light to the solute concentration and weight-average molar mass, Mw (Kendrick et al., 2001, Anal Biochem. 299(2):136-46; Wyatt, 1993, Anal. Chim. Acta 272(1):1-40):

$$\frac{K*c}{R(\theta, c)} = \frac{1}{MwP(\theta)} + 2A_2c \qquad \text{Equation 1}$$

where c is the solute concentration, R(θ,c) is the excess Raleigh ratio from the solute as a function of scattering angle and concentration, Mw is the molar mass, P(θ) describes the angular dependence of scattered light (~1 for particles with radius of gyration <50 nm), A2 is the second virial coefficient in the expansion of osmotic pressure (which can be neglected since measurements are performed on dilute solutions) and $$K* = \frac{4\pi^2 n_0^2}{N_A \lambda_0^4}\left(\frac{dn}{dc}\right)^2 \qquad \text{Equation 2}$$

where $n_0$ represents the solvent refractive index, $N_A$ is Avogadro's number, λ0 is the wavelength of the incident light in a vacuum, and dn/dc represents the specific refractive index increment for the solute.

The molar mass of BSA monomer served to evaluate the calibration constants of the light scattering and differential refractive index detectors during data collection (system suitability check). The relative standard deviation (% RSD) of the average molar mass of BSA determined from the UV and RI detectors was 5.0%.

The normalization coefficients for the light scattering detectors, inter-detector delay volume and band broadening terms were calculated from the BSA chromatograms collected for the A4F-MALLS condition employed. These values were applied to the data files collected for all the other samples to correct for these terms.

The dn/dc value and the extinction coefficient at 215 nm were experimentally determined using the protein conjugate analysis provided in the Astra software. The corrected extinction coefficient and dn/dc value was used to analyze all protein-protein complex samples.

7.4.3. Results

A4F-MALLS was used to assess the relative size distribution of complexes formed between recombinant KLB (REGN6424), recombinant FGFR1c (REGN6152), and several monospecific (REGN4661), bispecific (REGN4304), and trispecific (2+1 N-scFv) binding molecules. The results are shown in FIG. 11A (for REGN4661), FIG. 11B (for REGN4304), and FIG. 11C (the 2+1 N-scFv format). The theoretical molar mass and predicted stoichiometry of potential antibody:antigen complexes are provided as insets in FIGS. 11A-11O. As expected, the monospecific KLB binding molecule (REGN4661) formed canonical 1:1 (Peak 1, ~280 kDa) and 1:2 (Peak 2, ~356 kDa) complexes with KLB when combined at equimolar ratios (FIG. 11A). Similarly, when the control bispecific binding molecule (anti-KLBxFGFR1c; REGN4304) was mixed with an equimolar amount of KLB, a discrete, homogeneous peak (Peak 1) with a calculated molar mass of ~280 kDa was observed (FIG. 11B). Based on the calculated molar mass of the individual components, peak 1 likely represents a 1:1 bispecific:KLB complex. Further addition of FGFR1c to this mixture resulted in a broad peak (Peak 2) with a calculated molar mass range of ~305-444 kDa, which is generally consistent with a 1:1:1 bispecific:KLB:FGFR1c ternary complex (FIG. 11B). The upward trend in molar mass at the trailing end of peak 2 suggests larger complexes, weakly associated via KLB-FGFR1c interactions, may also be present in solution, but easily dissociate upon fractionation.

In comparison to the control monospecific and bispecific binding molecules, the trispecific binding molecule bound KLB and FGFR1c with a unique, higher order stoichiometry. When mixed with an equimolar amount of KLB, F1K-scFv6 IgG1 formed a largely discrete, homogeneous peak (Peak 1) having a molar mass of ~579 kDa, likely representing a complex containing 2 molecules of F1K-scFv6 IgG1 bound to 2 molecules of KLB (2:2 complex; FIG. 11C). Upon addition of varying amounts of FGFR1c to this mixture, a slightly broader, later-eluting peak (Peak 2) was observed with a calculated molar mass range of ~607-644 kDa. Peak 2 likely represents a mixture of ternary complexes containing 2 molecules of F1K-scFv6 IgG1, 2 molecules of KLB, and 1-2 molecules of FGFR1c (2:2:1 and 2:2:2 complexes; FIG. 11C).

FIG. 12A illustrates the stoichiometry of FGF21 complexed with FGFR1c and KLB. FIG. 12B illustrations a variety of alternative stoichiometries of FGF21-antibody binding. The data presented herein reveal that the trispecific binding molecules of the disclosure can bind KLB and FGFR1c to form ternary complexes having unique stoichiometries compared to control monospecific and bispecific binding molecules, which might contribute to their increased agonist activity as compared to bispecific binding molecules.

7.5. Example 5: FGFR3/APLP2 and FGFR3/CD63 2+1 N-scFv MBMs

7.5.1. Materials and Methods

7.5.1.1. Generation of MBMs

To construct 2+1 N-scFv MBMs with a monovalent scFv fused to a bivalent FGFR3 mAb, 16 APLP2-targeting and three CD63-targeting scFvs were individually fused to the N-terminus of a heavy chain of an FGFR3 parental antibody 30108 with a modified human IgG4 Fc backbone with effector silencing substitutions, Hole (Y349C, T366S, L368A, Y407V, EU numbering) and Star (H435R, Y436F, EU numbering) mutations (Table 11). The second heavy chain contains the identical 30108 Fab and a modified IgG4 Fc with the same effector silencing substitutions and Knob (S354C, T366W, EU numbering) mutations (Table 11). The general format of 2+1 N-scFv MBMs is illustrated in FIG. 1, and the FGFR3/APLP2 and FGFR3/CD63 2+1 N-scFv MBMs contain effector silencing substitutions, knob-in-hole mutations and star mutations. The general format of 2+1 N-scFv MBMs with hole mutations in the scFv-containing chain and knob mutations in the chain lacking an scFv domain is illustrated in FIG. 3C. The general format of 2+1 N-scFv MBMs with star mutations in the scFv-containing chain is illustrated in FIG. 3A.

DNA fragments encoding (i) various APLP2 or CD63 scFvs, in the orientation of VH (with VH-44C, Kabat numbering), linker (4×G₄S (SEQ ID NO: 57)), VL (with VL-100C mutation, Kabat numbering), linker (G₄S)₃ (SEQ ID NO: 1) for connecting scFv with Fab (ii) Fab region of 30108, and (iii) modified human IgG4 Fcs (Table 10) were synthesized by Integrated DNA Technologies, Inc. (San Diego, Calif.). Mammalian expression vectors for individual heavy chains were assembled by NEBuilder HiFi DNA Assembly Kit (New England BioLabs Inc.). For expression of FGFR3/APLP2 or CD63 2+1 N-scFv molecules, heavy chain 1-Hole*, heavy chain 2-Knob and ULC 3-20 DNAs were co-transfected into Expi293 cells (ThermoFisher Scientific) following the manufacturer's protocol. 50 ml of cell culture medium was harvested and processed for purification via a HiTrap Protein A FF column (GE Healthcare). For functional confirmation, 3ASB-5 and 3CSB-2 were scaled up to 200 ml and subject to a series of purification procedures including size exclusion chromatography as the final step. 30108 IgG, targeting FGFR3, made and purified previously was used as control.

7.5.1.2. Biacore Analysis on Target Binding

Biacore kinetics analysis was performed to assess the binding affinity of two MBMs, 3ASB-5 and 3CSB-2, to individual targets.

7.5.1.3. Proliferation Assays

Effect of 2+1 N-scFvs on bladder cancer cell proliferation was tested with UMUC14 cells expressing S249C mutation and RT4 cells expressing FGFR3-TACC3 fusion. mutation.

7.5.2. Results

7.5.2.1. Generation of FGFR3/APLP2 and FGFR3/CD63 2+1 N-scFv MBMs

A design summary of representative FGFR3/APLP2 and FGFR3/CD63 2+1 N-scFv MBMs that were expressed and purified is shown in Table 11.

TABLE 11

| | Hc1-Hole* | | Hc2-Knob | | |
| --- | --- | --- | --- | --- | --- |
| Molecule ID | 1. APLP scFv | Linker | 2. FGFR3 | 3. FGFR3 | Lc |
| 3ASB-5 | 21375P2 | 3xG$_4$S (SEQ ID NO: 1) | 30108P2 | 30108P2 | ULC 3-20 |

| | Hc1-Hole* | | Hc2-Knob | | |
| --- | --- | --- | --- | --- | --- |
| Molecule ID | 1. CD63 scFv | Linker | 2. FGFR3 | 3. FGFR3 | Lc |
| 3CSB-2 | H4H12450N | 3xG$_4$S (SEQ ID NO: 1) | 30108P2 | 30108P2 | ULC 3-20 |

| Molecule ID | Hc1 | | Hc2 | | Lc |
| --- | --- | --- | --- | --- | --- |
| H4H30108P2 IgG | NA | NA | 30108P2 | | ULC 3-20 |

7.5.2.2. FGFR3/APLP2 or CD63 2+1 N-scFvs can Bind to FGFR3, APLP2 and CD63

The results of Biacore kinetics analysis on 3ASB-5 and 3CSB-2 to individual targets are shown in Tables 12A-12C. Both 2+1 N-scFvs were found to bind to the common target FGFR3 similarly as the parental 30108 IgG control with $K_D$=8 nM. For 3ASB-5, the binding for APLP2 was found to be at sub nanomolar range with $K_D$=8.04E-10 M. For 3CSB-2, the $K_D$ for CD63 was found to be 5.88E-10 M, 4 fold weaker than the monovalent binding affinity of the parental H4H12450N IgG. In summary, both 3ASB-5 and 3CSB-2 possess expected binding capability to their targets, FGFR3, APLP2 and CD63.

TABLE 12A

| hAPLP2.mmh Binding Kinetics | | | | | | |
| --- | --- | --- | --- | --- | --- | --- |
| mAb Captured | Target | mAb Capture Level (RU) | 100 nM Antigen Bound (RU) | $k_a$ (1/Ms) | $k_d$ (1/s) | $K_D$ (M) |
| 3ASB-5 | FGFR3/APLP2 | 202.6 ± 5.8 | 26.8 | 5.27E+04 | 4.24E−05 | 8.04E−10 |
| H4H30108P2 IgG | FGFR3 | 326.1 ± 2.2 | −0.7 | NB | NB | NB |
| REGN1945 | FelD1 | 289.2 ± 2.9 | −0.5 | NB | NB | NB |

TABLE 12B hCD63.mmh Binding Kinetics

| mAb Captured | Target | mAb Capture Level (RU) | 100 nM Antigen Bound (RU) | $k_a$ (1/Ms) | $k_d$ (1/s) | $K_D$ (M) |
|---|---|---|---|---|---|---|
| 3CSB-2 | FGFR3/CD63 | 274.3 ± 3.1 | 19.5 | 3.59E+05 | 2.11E−04 | 5.88E−10 |
| H4H12450N IgG | CD63 | 754.9 ± 2.9 | 77.6 | 5.04E+05 | 7.15E−05 | 1.42E−10 |
| H4H30108P2 IgG | FGFR3 | 346.5 ± 6.3 | −4.3 | NB | NB | NB |
| REGN1945 | FeID1 | 330.6 ± 6.2 | 0.5 | NB | NB | NB |

TABLE 12C hFGFR3b.mmh Binding Kinetics

| mAb Captured | Target | mAb Capture Level (RU) | 100 nM Antigen Bound (RU) | $k_a$ (1/Ms) | $k_d$ (1/s) | $K_D$ (M) |
|---|---|---|---|---|---|---|
| 3ASB-5 | FGFR3/APLP2 | 276 ± 2.2 | 90.0 | 7.39E+04 | 6.12E−04 | 8.28E−09 |
| 3CSB-2 | FGFR3/CD63 | 274.3 ± 3.1 | 72.4 | 6.66E+04 | 5.71E−04 | 8.57E−09 |
| H4H30108P2 IgG | FGFR3 | 346.5 ± 6.3 | 117.8 | 8.36E+04 | 6.46E−04 | 7.73E−09 |
| REGN1945 | FeID1 | 330.6 ± 6.2 | 1.8 | NB | NB | NB |

7.5.2.3. FGFR3/APLP2 2+1 N-scFv 3ASB-5 and FGFR3/CD63 2+1 N-scFv 3CSB-2 can Provide Potent Proliferation Blockade in Both UMUC14 (S249C) and RT4 (FGFR3-TACC3) Cells Via Different Mechanisms Effect of 2+1 N-scFvs on bladder cancer cell proliferation was tested with UMUC14 cells expressing S249C mutation and RT4 cells expressing FGFR3-TACC3 fusion mutation. Parental antibody H4H30108P2 has demonstrated potent growth inhibition in RT4 cells but suboptimal growth inhibition activities in UMUC14 cells. 3CSB-2 and 3ASB-5 showed significantly enhanced activity in UMUC14 cells, with ~25% increase of growth inhibition at highest dose tested (100 nM) (FIG. 13A). In addition, the activities of 2+1 N-scFvs 3CSB-2 and 3ASB-5 were maintained at high level in RT4 cells and comparable to the parental antibody H4H30108P2 (FIG. 13B). Unlike parental FGFR3 antibody, 3CSB-2 and 3ASB-5 were found to be capable of blocking the proliferation of bladder cancer cells that are driven by different mutations (FIGS. 13A and 13B).

To further investigate the underlying mechanism of the FGFR3/APLP2 or FGFR3/CD63 MBMs, effects of antibody-induced receptor degradation were tested on UMUC14 cells. Interestingly, a different mechanism was observed with FGFR3/APLP2 vs. FGFR3/CD63 MBMs. Treatment with FGFR3/APLP2 MBM showed enhanced level of antibody-induced receptor degradation compared to cells without treatment, or cells treated with isotype control antibody (REGN1945) or parental antibody H4H30108P2 (FIG. 14). On the contrary, treatment with FGFR3/CD63 MBM did not affect FGFR3 receptor level, suggesting the enhanced growth inhibition activity of the bispecific 3CSB-2 MBM resulted from a different mechanism (FIG. 14).

8. SPECIFIC EMBODIMENTS

The present disclosure is exemplified by the specific embodiments below.

1. A multispecific binding molecule (MBM), comprising:
   (a) a first polypeptide chain comprising, in an N- to C-terminal orientation, (i) an scFv comprising a first antigen binding site ("ABS1") operably linked to (ii) a first heavy chain region of a first Fab ("Fab1") operably linked to (iii) an Fc domain;
   (b) a second polypeptide chain comprising, in an N- to C-terminal orientation, (i) a second heavy chain region of a second Fab ("Fab2") operably linked to (ii) an Fc domain;
   (c) a third polypeptide chain comprising a first light chain that pairs with the first heavy chain region to form Fab1, wherein Fab1 comprises a second antigen binding site ("ABS2"); and
   (d) a fourth polypeptide chain comprising a second light chain that pairs with the second heavy chain region to form Fab2, wherein Fab2 comprises a third antigen binding site ("ABS3").

2. The MBM of embodiment 1, in which each antigen binding site ("ABS") binds to a different epitope.

3. The MBM of embodiment 1 or embodiment 2, wherein two of ABS1, ABS2 and ABS3 specifically bind to different epitopes of the same target molecule.

4. The MBM of any one of embodiments 1 to 3, in which the scFv, Fab1 and Fab2 are capable of specifically binding their respective targets at the same time.

5. The MBM of any one of embodiments 1 to 4, in which at least one of ABS1, ABS2 and ABS3 specifically binds to a target molecule with a first tissue expression profile and at least one of ABS1, ABS2 and ABS3 specifically binds to a target molecule with a second tissue expression profile that is overlapping with, but not identical to, the first tissue expression profile.

6. The MBM of embodiment 5, wherein the first tissue expression profile and the second tissue expression profile overlap by 10 or fewer tissues.

7. The MBM of embodiment 6, wherein the first tissue expression profile and the second tissue expression profile overlap by 5 or fewer tissues.

8. The MBM of embodiment 7, wherein the first tissue expression profile and the second tissue expression profile overlap by 3 or fewer tissues.

9. The MBM of any one of embodiments 6 to 8, wherein the first and second tissue expression profiles are defined by the Human Protein Atlas (HPA) and/or by the Genotype-Tissue Expression (GTEx) project.

10. The MBM of any one of embodiments 6 to 9, wherein the first and second tissue expression profiles are protein expression profiles.

11. The MBM of any one of embodiments 6 to 9, wherein the first and second tissue expression profiles are mRNA expression profiles.

12. The MBM of any one of embodiments 1 to 11, wherein the affinity of the MBM to the target molecule of Fab1 is less than the affinity of a second MBM to the target molecule of Fab1 that lacks the scFv of the MBM but which is otherwise identical to the MBM in amino acid sequence.

13. The MBM of any one of embodiments 1 to 12, in which the scFv is linked to the first heavy chain region via a linker.

14. The MBM of embodiment 13, wherein the linker is at least 5 amino acids, at least 6 amino acids or at least 7 amino acids in length and is optionally up to 30 amino acids, up to 40 amino acids, up to 50 amino acids or up to 60 amino acids in length, and in some specific embodiments the linker is:
(a) 5 amino acids to 50 amino acids in length;
(b) 5 amino acids to 45 amino acids in length;
(c) 5 amino acids to 40 amino acids in length;
(d) 5 amino acids to 35 amino acids in length;
(e) 5 amino acids to 30 amino acids in length;
(f) 5 amino acids to 25 amino acids in length;
(g) 5 amino acids to 20 amino acids in length;
(h) 6 amino acids to 50 amino acids in length;
(i) 6 amino acids to 45 amino acids in length;
(j) 6 amino acids to 40 amino acids in length;
(k) 6 amino acids to 35 amino acids in length;
(l) 6 amino acids to 30 amino acids in length;
(m) 6 amino acids to 25 amino acids in length;
(n) 6 amino acids to 20 amino acids in length;
(o) 7 amino acids to 40 amino acids in length;
(p) 7 amino acids to 35 amino acids in length;
(q) 7 amino acids to 30 amino acids in length;
(r) 7 amino acids to 25 amino acids in length;
(s) 7 amino acids to 20 amino acids in length; or
(t) 10 amino acids to 60 amino acids in length.

15. The MBM of embodiment 14 or 14(m), wherein the linker is 20 amino acids to 50 amino acids in length, optionally wherein the linker is 25 to 35 amino acids in length.

16. The MBM of any one of embodiments 13 to 15, wherein the linker is or comprises a multimer of $G_nS$ (SEQ ID NO: 61) or $SG_n$ (SEQ ID NO: 62), where n is an integer from 1 to 7, optionally wherein the linker is or comprises a multimer of $G_4S$ (SEQ ID NO: 4).

17. The MBM of any one of embodiments 13 to 16, wherein the linker is or comprises a comprises two consecutive glycines (2Gly), three consecutive glycines (3Gly), four consecutive glycines (4Gly (SEQ ID NO: 5)), five consecutive glycines (5Gly (SEQ ID NO: 6)), six consecutive glycines (6Gly (SEQ ID NO: 7)), seven consecutive glycines (7Gly (SEQ ID NO: 8)), eight consecutive glycines (8Gly (SEQ ID NO: 9)) or nine consecutive glycines (9Gly (SEQ ID NO: 10)).

18. The MBM of embodiment any one of embodiments 13 to 17, which comprises
(a) a multimer of $G_nS$ (SEQ ID NO: 61) or $SG_n$ (SEQ ID NO: 62) (e.g., a multimer of $G_4S$ (SEQ ID NO: 4), where n is an integer from 1 to 7, e.g., which comprises a multimer of $G_4S$ (SEQ ID NO: 4); and
(b) one or more additional glycines, e.g., two consecutive glycines (2Gly), three consecutive glycines (3Gly), four consecutive glycines (4Gly (SEQ ID NO: 5)), five consecutive glycines (5Gly (SEQ ID NO: 6)), six consecutive glycines (6Gly (SEQ ID NO: 7)), seven consecutive glycines (7Gly (SEQ ID NO: 8)), eight consecutive glycines (8Gly (SEQ ID NO: 9)) or nine consecutive glycines (9Gly (SEQ ID NO: 10)).

19. The MBM of any one of embodiments 1 to 18, in which at least one of ABS1, ABS2 and ABS3 specifically binds a membrane-bound antigen.

20. The MBM of any one of embodiments 1 to 19, in which ABS1 and ABS3 specifically bind to membrane-bound antigens on the same cell.

21. The MBM of any one of embodiments 1 to 20, which is a trispecific binding molecule ("TBM").

22. The MBM of any one of embodiments 1 to 21, in which the first light chain and the second light chain are universal light chains.

23. The MBM of any one of embodiments 1 to 22, in which the light chain constant region and the first heavy chain constant region (CH1) of the first Fab or the second Fab are in a Crossmab arrangement.

24. The MBM of any one of embodiments 1 to 23, which comprises an Fc heterodimer.

25. The MBM of embodiment 24, wherein the Fc domains in the Fc heterodimer comprise knob-in-hole mutations as compared to a wild type Fc domain.

26. The MBM of embodiment 24 or embodiment 25, wherein at least one Fc domain in the Fc heterodimer comprises star mutations as compared to a wild type Fc domain.

27. The MBM of any one of embodiments 1 to 26, which is a trivalent MBM.

28. The MBM of any one of embodiments 1 to 27, wherein ABS3 specifically binds to human klotho beta ("KLB").

29. The MBM of embodiment 28, wherein ABS3 comprises the CDR sequences of an anti-KLB antibody, e.g., the CDR sequences of any one of the KLB binders set forth in Tables 2A-2B.

30. The MBM of embodiment 29, wherein ABS3 comprises the $V_H$ and/or $V_L$ sequences of an anti-KLB antibody, e.g., the $V_H$ and/or $V_L$ sequences of any one of the KLB binders set forth in Tables 2A-2B.

31. The MBM of any one of embodiments 1 to 30, wherein ABS1 specifically binds to human KLB.

32. The MBM of embodiment 31, wherein ABS1 comprises the CDR sequences of an anti-KLB antibody, e.g., the CDR sequences of any one of the KLB binders set forth in Tables 2A-2B.

33. The MBM of embodiment 32, wherein ABS1 comprises the $V_H$ and/or $V_L$ sequences of an anti-KLB antibody, e.g., the $V_H$ and/or $V_L$ sequences of any one of the KLB binders set forth in Tables 2A-2B.

34. The MBM of any one of 1 to 33, wherein ABS1 and ABS3 specifically bind to different epitopes on human KLB.

35. The MBM of embodiment 34, wherein ABS1 and ABS3 are capable of simultaneously specifically binding to their respective epitopes on human KLB.

36. The MBM of any one of embodiments 1 to 35, wherein ABS2 specifically binds to human fibroblast growth factor receptor 1c isoform ("FGFR1c").

37. The MBM of embodiment 36, wherein ABS2 comprises the CDR sequences of an anti-FGFR1c antibody, e.g., the CDR sequences of any one of the FGFR1c binders set forth in Tables 3A-3B.

38. The MBM of embodiment 37, wherein ABS2 comprises the $V_H$ and/or $V_L$ sequences of an anti-FGFR1c antibody, e.g., the $V_H$ and/or $V_L$ sequences of any one of the FGFR1c binders set forth in Tables 3A-3B.

39. The MBM of any one of embodiments 36 to 38, wherein ABS2 binds to loop D3 of FGFR1c.

40. The MBM of any one of embodiments 36 to 38, wherein ABS2 binds to loop D2 of FGFR1c.

41. The MBM of any one of embodiments 1 to 27, wherein ABS2 specifically binds to human fibroblast growth factor receptor 3 ("FGFR3").

42. The MBM of embodiment 41, wherein ABS2 comprises the CDR sequences of an anti-FGFR3 antibody, e.g., the CDR sequences of any one of the FGFR3 binders set forth in Table 4.

43. The MBM of embodiment 42, wherein ABS2 comprises the $V_H$ and/or $V_L$ sequences of an anti-FGFR3 antibody, e.g., the $V_H$ and/or $V_L$ sequences of any one of the FGFR3 binders set forth in Table 4.

44. The MBM of any one of embodiments 1 to 27 or 41 to 43, wherein ABS3 specifically binds to human FGFR3.

45. The MBM of embodiment 44, wherein ABS3 comprises the CDR sequences of an anti-FGFR3 antibody, e.g., the CDR sequences of any one of the FGFR3 binders set forth in Table 4

46. The MBM of embodiment 45, wherein ABS3 comprises the $V_H$ and/or $V_L$ sequences of an anti-FGFR3 antibody, e.g., the $V_H$ and/or $V_L$ sequences of any one of the FGFR3 binders set forth in Table 4.

47. The MBM of any one of embodiments 1 to 27, wherein ABS2 and ABS3 specifically bind to human FGFR3.

48. The MBM of embodiment 47, wherein ABS2 comprises the CDR sequences of an anti-FGFR3 antibody, e.g., the CDR sequences of any one of the FGFR3 binders set forth in Table 4.

49. The MBM of embodiment 48, wherein ABS2 comprises the $V_H$ and/or $V_L$ sequences of an anti-FGFR3 antibody, e.g., the $V_H$ and/or $V_L$ sequences of any one of the FGFR3 binders set forth in Table 4.

50. The MBM of any one of embodiments 47 to 49, wherein ABS3 comprises the CDR sequences of an anti-FGFR3 antibody, e.g., the CDR sequences of any one of the FGFR3 binders set forth in Table 4.

51. The MBM of embodiment 50, wherein ABS3 comprises the $V_H$ and/or $V_L$ sequences of an anti-FGFR3 antibody, e.g., the $V_H$ and/or $V_L$ sequences of any one of the FGFR3 binders set forth in Table 4.

52. The MBM of any one of embodiments 47 to 51, wherein ABS2 and ABS3 specifically bind to the same epitope on FGFR3.

53. The MBM of embodiment 52, wherein ABS2 and ABS3 comprise the same CDR sequences.

54. The MBM of embodiment 53, wherein ABS2 and ABS3 comprise the same $V_H$ and $V_L$ sequences.

55. The MBM of any one of embodiments 41 to 54, wherein ABS1 specifically binds to human CD63.

56. The MBM of embodiment 55, wherein ABS1 comprises the CDR sequences of an anti-CD63 antibody, e.g., the CDR sequences of any one of the CD63 binders set forth in Table 6.

57. The MBM of embodiment 56, wherein ABS1 comprises the $V_H$ and/or $V_L$ sequences of an anti-CD63 antibody, e.g., the $V_H$ and/or $V_L$ sequences of any one of the CD63 binders set forth in Table 6.

58. The MBM of any one of embodiments 41 to 54, wherein ABS1 specifically binds to human amyloid precursor-like protein 2 (APLP2).

59. The MBM of embodiment 58, wherein ABS1 comprises the CDR sequences of an anti-APLP2 antibody, e.g., the CDR sequences of any one of the APLP2 binders set forth in Table 5.

60. The MBM of embodiment 59, wherein ABS1 comprises the $V_H$ and/or $V_L$ sequences of an anti-APLP2 antibody, e.g., the $V_H$ and/or $V_L$ sequences of any one of the APLP2 binders set forth in Table 5.

61. A conjugate comprising the MBM of any one of embodiments 1 to 27 and a cytotoxic or cytostatic agent.

62. A pharmaceutical composition comprising the MBM of any one of embodiments 1 to 27 or the conjugate of embodiment 61 and an excipient.

63. A method of treating cancer, comprising administering to a subject suffering from cancer an effective amount of the MBM of any one of embodiments 1 to 27, the conjugate of embodiment 61, or the pharmaceutical composition of embodiment 62.

64. The method of embodiment 63, in which the cancer is associated with expression of the target molecules to which ABS1, ABS2 and/or ABS3 specifically bind.

65. The method of embodiment 63 or embodiment 64, wherein the MBM is an MBM according to any one of embodiments 41 to 60, the conjugate comprises an MBM according to any one of embodiments 41 to 60, or the pharmaceutical composition comprises an MBM according to any one of embodiments 41 to 60 or a conjugate comprising an MBM according to any one of embodiments 41 to 60.

66. The method of any one of embodiments 63 to 65, wherein the cancer is bladder cancer.

67. The method of any one of embodiments 63 to 65, wherein the cancer is glioblastoma.

68. The method of any one of embodiments 63 to 65, wherein the cancer is squamous cell lung carcinoma.

69. A method of treating nonalcoholic steatohepatitis ("NASH"), comprising administering to a subject suffering from NASH an effective amount of the MBM of any one of embodiments 1 to 27, the conjugate of embodiment 61, or the pharmaceutical composition of embodiment 62.

70. A method of treating metabolic disease, comprising administering to a subject suffering from metabolic disease an effective amount of the MBM of any one of embodiments 1 to 27, the conjugate of embodiment 61, or the pharmaceutical composition of embodiment 62.

71. A method of reducing circulating HDL cholesterol, comprising administering to a subject suffering from elevated HDL levels an effective amount of the MBM of any one of embodiments 1 to 27, the conjugate of embodiment 61, or the pharmaceutical composition of embodiment 62.

72. A method of increasing circulating LDL cholesterol, comprising administering to a subject suffering from low LDL levels an effective amount of the MBM of any one of embodiments 1 to 27, the conjugate of embodiment 61, or the pharmaceutical composition of embodiment 62.

73. A method of reducing blood triglycerides, comprising administering to a subject suffering from elevated triglyceride levels an effective amount of the MBM of any one of embodiments 1 to 27, the conjugate of embodiment 61, or the pharmaceutical composition of embodiment 62.

74. A method of reducing blood glucose, comprising administering to a subject suffering from elevated glucose levels an effective amount of the MBM of any one of embodiments 1 to 27, the conjugate of embodiment 61, or the pharmaceutical composition of embodiment 62.

75. A method of treating obesity, comprising administering to a subject suffering from obesity an effective amount of the MBM of any one of embodiments 1 to 27, the conjugate of embodiment 61, or the pharmaceutical composition of embodiment 62.

76. A method of treating diabetes, comprising administering to a subject suffering from diabetes an effective amount of the MBM of any one of embodiments 1 to 27, the conjugate of embodiment 61, or the pharmaceutical composition of embodiment 62.

77. The method of any one of embodiments 69 to 76, wherein the MBM is an MBM according to any one of embodiments 28 to 40, the conjugate comprises an MBM according to any one of embodiments 28 to 40, or the pharmaceutical composition comprises an MBM according to any one of embodiments 28 to 40 or a conjugate comprising an MBM according to any one of embodiments 28 to 40.

78. A nucleic acid or plurality of nucleic acids encoding the MBM of any one of embodiments of any one of embodiments 1 to 60.

79. A cell engineered to express the MBM of any one of embodiments 1 to 60.

80. A cell transfected with one or more expression vectors comprising one or more nucleic acid sequences encoding the MBM of any one of embodiments 1 to 60 under the control of one or more promoters.

81. A method of producing a MBM, comprising:
 (a) culturing the cell of embodiment 79 or 80 in conditions under which the MBM is expressed; and
 (b) recovering the MBM from the cell culture 82. The method of embodiment 81, which further comprises enriching for the MBM.

83. The method of embodiment 81 or embodiment 82, which further comprises purifying the MBM.

9. CITATION OF REFERENCES

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there is an inconsistency between the teachings of one or more of the references incorporated herein and the present disclosure, the teachings of the present specification are intended.

What is claimed is:

1. A method, comprising contacting a cell expressing fibroblast growth factor receptor 3 (FGFR3) and amyloid precursor-like protein 2 (APLP2) with a multispecific binding molecule (MBM) comprising:
   (a) a first polypeptide chain comprising, in an N- to C-terminal orientation, (i) an scFv comprising means for binding human APLP2, (ii) a first heavy chain region of a first Fab comprising means for binding human FGFR3, and (iii) a first Fc domain;
   (b) a second polypeptide chain comprising, in an N- to C-terminal orientation, (i) a second heavy chain region of a second Fab comprising means for binding human FGFR3 and (ii) a second Fc domain;
   (c) a third polypeptide chain comprising a first light chain that pairs with the first heavy chain region to form the first Fab; and
   (d) a fourth polypeptide chain comprising a second light chain that pairs with the second heavy chain region to form the second Fab.

2. The method of claim 1, wherein the scFv is linked to the first heavy chain region via a linker.

3. The method of claim 2, wherein the linker is 5 amino acids to 50 amino acids in length.

4. The method of claim 2, wherein the linker is 7 amino acids to 50 amino acids in length.

5. The method of claim 2, wherein the linker is 5 amino acids to 20 amino acids in length.

6. The method of claim 2, wherein the linker is 7 amino acids to 20 amino acids in length.

7. The method of claim 2, wherein the linker comprises a multimer of GnS (SEQ ID NO: 61) or SGn (SEQ ID NO: 62), wherein n is an integer from 1 to 7.

8. The method of claim 2, wherein the linker comprises a multimer of $G_4S$ (SEQ ID NO: 4).

9. The method of claim 1, wherein the first Fc domain and the second Fc domain form a heterodimer.

10. The method of claim 9, wherein the first Fc domain comprises a knob mutation as compared to a wild type Fc domain and the second Fc domain comprises a hole mutation as compared to a wild type Fc domain.

11. The method of claim 9, wherein the first Fc domain comprises a hole mutation as compared to a wild type Fc domain and the second Fc domain comprises a knob mutation as compared to a wild type Fc domain.

12. The method of claim 1, wherein the first light chain and the second light chain are universal light chains.

13. The method of claim 1, wherein the scFv has the configuration, in an N- to C-terminal orientation, VL-linker-VH.

14. The method of claim 1, wherein the scFv has the configuration, in an N- to C-terminal orientation, VH-linker-VL.

15. The method of claim 1, wherein the first polypeptide chain further comprises, between the heavy chain region of the first Fab and the first Fc domain, a first hinge domain.

16. The method of claim 14, wherein the second polypeptide chain further comprises, between the heavy chain region of the second Fab and the second Fc domain, a second hinge domain.

17. The method of claim 1, wherein the cell is in vitro.

18. The method of claim 1, wherein the cell is a cancer cell.

* * * * *

SEQUENCE LISTING

```
<160> NUMBER OF SEQ ID NOS: 65

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Gly Gly Ser Gly Gly Gly Gly Ser Gly Gly Gly Gly Ser
1               5                   10                  15

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(9)
<223> OTHER INFORMATION: Each of amino acids 1-9 can independently be
      present or absent

<400> SEQUENCE: 2

Gly Gly Gly Gly Gly Gly Gly Gly Gly Gly Ser
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MISC_FEATURE
<222> LOCATION: (3)..(11)
<223> OTHER INFORMATION: Each of amino acids 3-11 can independently be
      present or absent

<400> SEQUENCE: 3

Ser Gly Gly Gly Gly Gly Gly Gly Gly Gly
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Gly Gly Ser
1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Gly
1

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Gly Gly Gly
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Gly Gly Gly Gly
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8
```

Gly Gly Gly Gly Gly Gly Gly
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Gly Gly Gly Gly Gly Gly
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Gly Gly Gly Gly Gly Gly Gly
1               5

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Pro Pro Cys
1

<210> SEQ ID NO 12
<211> LENGTH: 4
<212> TYPE: PRT
<213> ORGANISM: Homo sapiens

<400> SEQUENCE: 12

Cys Pro Ser Cys
1

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Pro Lys Ser Cys Asp Lys Thr His Thr Cys Pro Pro Cys Pro Ala
1               5                   10                  15

Pro Pro Val Ala
            20

<210> SEQ ID NO 14
<211> LENGTH: 17
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 14

Glu Ser Lys Tyr Gly Pro Pro Cys Pro Pro Cys Ala Pro Pro Val
1               5                   10                  15

Ala

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Pro Pro Cys Pro Ala Pro Gly Gly Gly Gly Pro Ser Val Phe
1               5                   10                  15

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Pro Pro Cys Pro Ala Pro Gly Gly Gly Pro Ser Val Phe
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Cys Pro Pro Cys Pro Ala Pro Gly Gly Pro Ser Val Phe
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Cys Pro Pro Cys Pro Ala Pro Gly Pro Ser Val Phe
1               5                   10

<210> SEQ ID NO 19
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Lys Arg Val Glu Ser Lys Tyr Gly Pro Pro Cys Pro Pro Cys Pro
1               5                   10                  15
```

Ala Pro Pro Val Ala Gly Pro Ser Val Phe Leu Phe Pro Lys Pro
            20                  25                  30

Lys Asp Thr Leu Met Ile Ser Arg Thr Pro Glu Val Thr Cys Val Val
        35                  40                  45

Val Asp Val Ser Gln Glu Asp Pro Glu Val Gln Phe Asn Trp Tyr Val
    50                  55                  60

Asp Gly Val Glu Val His Asn Ala Lys Thr Lys Pro Arg Glu Glu Gln
65                  70                  75                  80

Phe Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Gly
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Gln Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Arg Leu Thr Val Asp Lys Ser Arg Trp Gln Glu Gly Asn Val Phe
        195                 200                 205

Ser Cys Ser Val Met His Glu Ala Leu His Asn His Tyr Thr Gln Lys
    210                 215                 220

Ser Leu Ser Leu Ser Leu Gly Lys
225                 230

<210> SEQ ID NO 20
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Lys Lys Val Glu Pro Lys Ser Cys Asp Lys Thr His Thr Cys Pro
1               5                   10                  15

Pro Cys Pro Ala Pro Pro Val Ala Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser Gln Glu Asp Pro Glu Val Gln Phe Asn
    50                  55                  60

Trp Tyr Val Asp Gly Val Glu Val His Asn Ala Lys Thr Lys Pro Arg
65                  70                  75                  80

Glu Glu Gln Phe Asn Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Gly Leu Pro Ser Ser Ile Glu Lys Thr Ile Ser Lys Ala Lys
        115                 120                 125

Gly Gln Pro Arg Glu Pro Gln Val Tyr Thr Leu Pro Pro Ser Arg Asp

```
                130                 135                 140
Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
                180                 185                 190

Phe Leu Tyr Ser Lys Leu Thr Val Asp Lys Ser Arg Trp Gln Gln Gly
                195                 200                 205

Asn Val Phe Ser Cys Ser Val Met His Glu Ala Leu His Asn His Tyr
                210                 215                 220

Thr Gln Lys Ser Leu Ser Leu Ser Pro Gly Lys
225                 230                 235

<210> SEQ ID NO 21
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Pro Val Ala Gly Pro Ser Val Phe Leu Phe Pro Pro Lys
                115                 120                 125

Pro Lys Asp Thr Leu Met Ile Ser Arg Thr Pro Glu Val Thr Cys Val
                130                 135                 140

Val Val Asp Val Ser Gln Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Tyr Arg Val Val Ser Val Leu Thr Val Leu His
                180                 185                 190

Gln Asp Trp Leu Asn Gly Lys Glu Tyr Lys Cys Lys Val Ser Asn Lys
                195                 200                 205

Gly Leu Pro Ser Ser Ile Glu Lys Thr Ile Ser Lys Ala Lys Gly Gln
                210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255
```

```
Ser Asp Ile Ala Val Glu Trp Glu Ser Asn Gly Gln Pro Glu Asn Asn
                260                 265                 270

Tyr Lys Thr Thr Pro Pro Val Leu Asp Ser Asp Gly Ser Phe Phe Leu
            275                 280                 285

Tyr Ser Lys Leu Thr Val Asp Lys Ser Arg Trp Gln Gln Gly Asn Val
        290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 22
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285
```

```
Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 23
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser Gln Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn Arg Phe Thr Gln
```

Lys Ser Leu Ser Leu Ser Pro Gly Lys
                325

<210> SEQ ID NO 24
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn Arg Phe Thr Gln Lys Ser Leu
305                 310                 315                 320

Ser Leu Ser Leu Gly Lys
                325

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 25

His His His His His
1               5

<210> SEQ ID NO 26
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Ala Val Ile Trp Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Ala Ala Gly Leu His Tyr Tyr Tyr Gly Met Asp
            100                 105                 110

Val Trp Gly Gln Gly Thr Thr Val Thr Val Ser Ser
        115                 120

<210> SEQ ID NO 27
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Gly Ser Ser Pro
                85                  90                  95

Leu Thr Phe Gly Gly Gly Thr Glu Val Glu Ile Lys

```
                    100                 105

<210> SEQ ID NO 28
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Val Gln Leu Gln Gln Ser Gly Ala Glu Val Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Gly Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Ser Asp Tyr Tyr Gly Ser Arg Ser Phe Ala Tyr Trp Gly Gln
            100                 105                 110

Gly Thr Leu Val Thr Val Ser Ser
        115                 120

<210> SEQ ID NO 29
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Val Tyr Met His Trp Tyr Gln Gln Lys Pro Gly Gln Pro Pro
        35                  40                  45

Lys Leu Leu Ile Tyr Leu Ala Ser Tyr Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Val Gln Ala Glu Asp Val Ala Val Tyr Tyr Cys Gln His Ser Arg
                85                  90                  95

Asp Leu Thr Phe Pro Phe Gly Gly Thr Lys Leu Glu Ile Lys
            100                 105                 110

<210> SEQ ID NO 30
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30
```

Glu Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Asp Tyr
            20                  25                  30

Tyr Met His Trp Val Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Tyr Met Asp Val Trp Gly Lys Gly Thr Leu Val Thr
            100                 105                 110

Val Ser Ser
        115

<210> SEQ ID NO 31
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Thr Thr Leu Thr Gln Ser Pro Asp Thr Leu Ser Leu Ser Pro Gly
1               5                   10                  15

Glu Gly Ala Thr Leu Ser Cys Arg Ala Ser Gln Ser Val Ser Gly Ser
            20                  25                  30

Ala Leu Ala Trp Tyr Gln Gln Lys Pro Gly Gln Ala Pro Arg Leu Leu
        35                  40                  45

Ile Tyr Asp Ala Ser Ser Arg Ala Thr Gly Val Pro Asp Arg Phe Ser
    50                  55                  60

Gly Ser Gly Ser Gly Ala Asp Phe Ser Leu Thr Ile Ser Arg Leu Glu
65                  70                  75                  80

Pro Glu Asp Phe Ala Val Tyr Ser Cys Gln Gln Tyr Gly Ser Ser Pro
                85                  90                  95

Leu Thr Phe Gly Pro Gly Thr Lys Val Asp Val Lys
            100                 105

<210> SEQ ID NO 32
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Gln Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Pro Ile Leu Gly Ile Ala Asn Tyr Ala Gln Lys Phe Gln
    50                  55                  60

Gly Arg Val Thr Ile Thr Ala Asp Lys Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Gly Gly Asp Leu Gly Gly Met Asp Val Trp Gly Gln Gly
            100                 105                 110

<210> SEQ ID NO 33
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Arg His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Ala Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Ile Pro Pro Thr Phe Gly Pro Gly Thr Lys Val Asp Lys
            100                 105                 110

<210> SEQ ID NO 34
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Thr
            20                  25                  30

Trp Ile Ser Trp Val Pro Gly Lys Gly Leu Glu Trp Val Gly Glu Ile
        35                  40                  45

Asp Pro Tyr Asp Gly Asp Thr Tyr Tyr Ala Asp Ser Val Lys Gly Arg
    50                  55                  60

Phe Thr Ile Ser Ala Asp Thr Ser Lys Asn Leu Gln Met Asn Ser Leu
65                  70                  75                  80

Arg Ala Glu Asp Thr Ala Val Tyr Tyr Cys Ala Ser Ser Gly Tyr Gly
                85                  90                  95

Gly Ser Asp Tyr Ala Met Asp Tyr Trp Gly Gln
            100                 105

<210> SEQ ID NO 35
<211> LENGTH: 107
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 35

Asp Ile Gln Met Thr Gln Ser Pro Ser Leu Ser Ala Ser Val Gly
1               5                  10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Trp Glu Ile Lys
            100                 105

<210> SEQ ID NO 36
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Asn Asn
            20                  25                  30

Tyr Ile His Trp Val Pro Gly Lys Gly Leu Glu Trp Val Ala Asp Ile
        35                  40                  45

Tyr Pro Asn Asp Gly Asp Thr Asp Tyr Ala Asp Ser Val Lys Gly Arg
    50                  55                  60

Phe Thr Ile Ser Ala Asp Thr Ser Lys Asn Leu Gln Met Asn Ser Leu
65                  70                  75                  80

Arg Ala Glu Asp Thr Ala Val Tyr Tyr Cys Ala Arg Glu His Phe Asp
                85                  90                  95

Ala Trp Val His Tyr Tyr Val Met Asp Tyr Trp Gly Gln
            100                 105

<210> SEQ ID NO 37
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Thr Ser Asn
            20                  25                  30

Trp Ile Ser Trp Val Pro Gly Lys Gly Leu Glu Trp Val Ala Glu Ile
        35                  40                  45
```

```
Asp Pro Tyr Asp Gly Ala Thr Asp Tyr Ala Asp Ser Val Lys Gly Arg
    50                  55                  60

Phe Thr Ile Ser Ala Asp Thr Ser Lys Asn Leu Gln Met Asn Ser Leu
 65                  70                  75                  80

Arg Ala Glu Asp Thr Ala Val Tyr Tyr Cys Ala Thr Gly Thr Asp Trp
                 85                  90                  95

Met Asp Tyr Trp Gly Gln
            100

<210> SEQ ID NO 38
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Ser Thr
                 20                  25                  30

Gly Ile Ser Trp Val Arg Gln Ala Pro Gly Lys Gly Leu Glu Trp Val
             35                  40                  45

Gly Arg Ile Tyr Pro Thr Ser Gly Ser Thr Asn Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Thr Tyr Gly Ile Tyr Asp Leu Tyr Val Asp Tyr Thr Glu Tyr
                100                 105                 110

Val Met Asp Tyr Trp Gly Gln Gly Thr Leu Val Thr Val Ser Ser Ala
            115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
                195                 200                 205

Ile Cys Asn Val Asn His Lys Pro Ser Asn Thr Lys Val Asp Lys Lys
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300
```

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 39
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Thr Ser
            20                  25                  30

Leu Ala Trp Tyr Lys Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Thr Gly His Pro Gln
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser

Phe Asn Arg Gly Glu Cys
    210

<210> SEQ ID NO 40
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Met Phe Thr Ser Tyr
            20                  25                  30

Gly Ile Ser Trp Val Arg Gln Ala Pro Gly Gln Gly Leu Glu Trp Met
        35                  40                  45

Gly Trp Val Ser Thr Tyr Asn Gly Asp Thr Asn Tyr Ala Gln Lys Phe
    50                  55                  60

Gln Gly Arg Val Thr Val Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Arg Val Leu Gly Tyr Tyr Asp Ser Ile Asp Gly Tyr Tyr Tyr Gly
            100                 105                 110

Met Asp Val Trp Gly Gln Gly Thr Thr Val Thr Val Ser Ser
        115                 120                 125

<210> SEQ ID NO 41
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Ser Val Leu Thr Gln Pro Pro Ser Leu Ser Val Ala Pro Gly Lys
1               5                   10                  15

Thr Ala Thr Phe Thr Cys Gly Gly Asn Asn Ile Gly Asp Lys Ser Val
            20                  25                  30

His Trp Tyr Arg Gln Lys Pro Gly Gln Ala Pro Val Leu Val Met Tyr
        35                  40                  45

Leu Asp Thr Glu Arg Pro Ser Gly Ile Pro Glu Arg Met Ser Gly Ser
    50                  55                  60

Asn Phe Gly Asn Thr Ala Thr Leu Thr Ile Thr Arg Val Glu Ala Gly
65                  70                  75                  80

Asp Glu Ala Asp Tyr Tyr Cys Gln Val Trp Ser Gly Ser Asp His
                85                  90                  95

Trp Phe Gly Gly Gly Thr Lys Leu Thr Val Leu Gly
            100                 105

<210> SEQ ID NO 42
<211> LENGTH: 126
<212> TYPE: PRT
<213> ORGANISM: Artificial Sequence
<220> FEATURE:
<223> OTHER INFORMATION: Description of Artificial Sequence: Synthetic -continued

```
            polypeptide

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Val Met Ser Trp Val Arg Gln Ala Pro Gly Lys Gly Pro Glu Trp Val
        35                  40                  45

Ser Gly Ile Ser Gly Arg Thr Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Arg Ile Thr Ala Ala Gly Arg Gly Tyr Tyr Tyr Tyr Tyr Gly
            100                 105                 110

Met Asp Val Trp Gly Arg Gly Thr Thr Val Thr Val Ser Ser
        115                 120                 125

<210> SEQ ID NO 43
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 44
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Ala Asp Tyr
            20                  25                  30

Ala Met His Trp Val Arg Gln Ala Pro Gly Lys Gly Leu Glu Trp Val
        35                  40                  45
```

```
Ser Gly Ile Ser Trp Asn Ser Gly Asn Ile Asp Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Thr Glu Asp Thr Ala Leu Tyr Tyr Cys
                85                  90                  95

Ala Lys Val Arg Ile Val Val Ala Gly Tyr Tyr Tyr Tyr Tyr Tyr Gly
                100                 105                 110

Met Asp Val Trp Gly Gln Gly Thr Thr Val Thr Val Ser Ser
            115                 120                 125

<210> SEQ ID NO 45
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Val Gln Ser Gly Val Glu Val Lys Lys Pro Gly Ala
 1               5                  10                  15

Ser Val Lys Val Ser Cys Lys Ala Ser Gly Tyr Thr Phe Thr Asp Tyr
                20                  25                  30

Gly Ile Ser Trp Val Arg Gln Ala Pro Gly Gln Gly Leu Glu Trp Met
            35                  40                  45

Gly Trp Ile Ser Ala His Asn Gly Asn Thr Asn Tyr Ala Gln Lys Leu
        50                  55                  60

Gln Gly Arg Val Thr Met Thr Thr Asp Thr Ser Thr Asn Thr Ala Tyr
 65                  70                  75                  80

Met Glu Leu Arg Ser Leu Arg Ser Asp Asp Thr Ala Val Tyr Tyr Cys
                85                  90                  95

Ala Arg Arg Asn Trp Lys Tyr Phe Asp Tyr Trp Gly Gln Gly Thr Leu
                100                 105                 110

Val Thr Val Ser Ser
            115

<210> SEQ ID NO 46
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Lys Leu Val Glu Ser Gly Gly Gly Leu Val Gln Pro Gly Gly
 1               5                  10                  15

Ser Leu Lys Leu Ser Cys Ala Thr Ser Gly Phe Thr Phe Ser Asp Tyr
                20                  25                  30

Tyr Met Ser Trp Val Arg Gln Thr Pro Glu Lys Arg Leu Glu Trp Val
            35                  40                  45

Ala Tyr Ile Ser Ser Ser Gly Ser Thr Tyr Tyr Ser Asp Thr Val
        50                  55                  60

Lys Gly Gln Phe Thr Ile Ser Arg Asp Asn Ala Lys Asn Thr Leu Tyr
 65                  70                  75                  80

Leu Gln Met Ser Arg Leu Lys Ser Glu Asp Thr Ala Met Tyr Tyr Cys
                85                  90                  95
```

Ala Arg Arg Glu Asp Tyr Asp Gly Arg Leu Thr Tyr Trp Gly Gln Gly
            100                 105                 110

Thr Leu Val Thr Ile Ser Ala
        115

<210> SEQ ID NO 47
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met Asn Trp Tyr Gln Gln Lys Pro Gly Gln Pro Pro
        35                  40                  45

Lys Val Leu Ile Tyr Leu Ala Ser Lys Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Tyr Thr Phe Gly Gly Gly Thr Lys Leu Glu Ile Lys
            100                 105                 110

<210> SEQ ID NO 48
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Val Gln Leu Val Glu Ser Gly Gly Gly Leu Val Gln Pro Gly Lys
1               5                   10                  15

Ser Leu Lys Leu Thr Cys Ala Thr Ser Gly Leu Thr Phe Asn Thr Ala
            20                  25                  30

Trp Met His Trp Val Arg Gln Ser Pro Asp Lys Arg Leu Glu Trp Ile
        35                  40                  45

Gly Arg Ile Lys Asp Lys Ser Asn Asn Tyr Ala Ala Asp Tyr Val Glu
    50                  55                  60

Ser Val Arg Gly Arg Phe Thr Ile Ser Arg Asp Asp Ser Lys Ser Ser
65                  70                  75                  80

Ile Tyr Leu Gln Met Asn Ser Leu Lys Glu Glu Asp Ser Ala Thr Tyr
                85                  90                  95

Phe Cys Phe His Asn Ser Leu Ala Tyr Trp Gly Gln Gly Thr Met Val
            100                 105                 110

Thr Val Ser Ser
        115

<210> SEQ ID NO 49
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asn Ile Val Met Thr Gln Ser Pro Lys Ser Met Ser Ile Ser Val Gly
1               5                   10                  15

Asp Arg Val Thr Met Asn Cys Lys Ala Ser Gln Asn Val Asp Asn Ser
            20                  25                  30

Ile Ala Trp Tyr Gln Gln Lys Pro Gly Gln Ser Pro Lys Leu Leu Ile
        35                  40                  45

Tyr Tyr Ala Thr Asn Arg Tyr Thr Gly Val Pro Asp Arg Phe Thr Gly
    50                  55                  60

Gly Gly Phe Gly Thr Asp Phe Thr Leu Thr Ile Ser Ser Val Gln Pro
65                  70                  75                  80

Glu Asp Ala Ala Ser Tyr Tyr Cys Gln Arg Ile Tyr Asp Cys Pro Asn
                85                  90                  95

Thr Phe Gly Gly Gly Thr Lys Leu Glu Leu Lys
            100                 105

<210> SEQ ID NO 50
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Val Gln Leu Gln Glu Ser Gly Pro Gly Leu Met Lys Pro Ser Glu
1               5                   10                  15

Thr Leu Ser Leu Thr Cys Thr Val Ser Gly Gly Ser Phe Ser Ser Tyr
            20                  25                  30

Tyr Trp Asn Trp Ile Arg Gln Ser Pro Gly Lys Gly Leu Glu Trp Ile
        35                  40                  45

Gly Tyr Ile Arg Tyr Ser Gly Asp Thr Asn Tyr Lys Pro Ser Leu Lys
    50                  55                  60

Ser Arg Phe Thr Ile Ser Ile Asp Thr Ser Lys Asn Leu Phe Ser Leu
65                  70                  75                  80

Arg Leu Lys Ser Val Thr Ala Ala Asp Thr Ala Val Tyr Tyr Cys Ala
                85                  90                  95

Arg Met Gly Leu Gly Ser Asp Ala Phe Asp Ile Trp Gly Gln Gly Thr
            100                 105                 110

Met Val Thr Val Ser Ser
        115

<210> SEQ ID NO 51
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Asn Asn Asn
            20                  25                  30

Tyr Leu Ala Trp Tyr Gln Gln Lys Pro Gly Gln Ala Pro Arg Leu Leu
                35                  40                  45

Ile Tyr Gly Val Phe Asn Arg Ala Thr Asn Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Trp Thr Phe Gly Gln Gly Thr Lys Val Glu Ile Lys
                100                 105

<210> SEQ ID NO 52
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Val Gln Leu Gln Glu Ser Gly Pro Arg Leu Val Lys Pro Ser Glu
1               5                   10                  15

Thr Leu Ser Leu Thr Cys Ile Val Ser Gly Gly Ser Ile Ser Asn Phe
                20                  25                  30

Tyr Trp Asn Trp Ile Arg Gln Ser Pro Gly Lys Gly Leu Glu Trp Ile
                35                  40                  45

Gly Tyr Phe Phe Tyr Thr Gly Thr Ile Asp Tyr Asn Pro Ser Leu Lys
 50                  55                  60

Ser Arg Val Thr Ile Ser Leu Asp Thr Ser Lys Asn Gln Phe Ser Leu
65                  70                  75                  80

Asn Leu Arg Leu Leu Thr Ala Ala Asp Ala Ala Val Tyr Tyr Cys Ala
                85                  90                  95

Arg Met Gly Leu Gly Ala Asn Ala Phe Asp Ile Trp Gly His Gly Thr
                100                 105                 110

Met Val Thr Val Ser Ser
        115

<210> SEQ ID NO 53
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln His Val Ser Ser Asn
                20                  25                  30

Tyr Leu Ala Trp Tyr Gln Gln Lys Pro Gly Gln Ala Pro Arg Leu Leu
                35                  40                  45

Ile Tyr Gly Gly Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
65                  70                  75                  80

Pro Ala Asp Phe Ala Val Phe Tyr Cys Gln Gln Tyr Gly Asn Ser Pro
                85                  90                  95

```
Trp Thr Phe Gly Gln Gly Thr Lys Val Glu Met Lys
            100                 105
```

<210> SEQ ID NO 54
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Gln Val Gln Leu Gln Glu Ser Gly Pro Lys Val Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Asn Trp Ile Arg Gln Ser Pro Gly Lys Gly Leu Glu Trp Ile
        35                  40                  45

Gly Tyr Thr Lys Arg Gly Tyr Thr Asp Tyr Asn Pro Ser Leu Arg Ser
50                  55                  60

Arg Val Thr Ile Ser Glu Asp Thr Ser Lys Asn Gln Phe Ser Leu Arg
65                  70                  75                  80

Ile Ser Ser Val Thr Ala Ala Asp Thr Ala Val Tyr Tyr Cys Ala Gln
                85                  90                  95

Met Gly Trp Gly Ser His Ala Phe Asp Met Trp Gly Gln Gly Thr Met
            100                 105                 110

Val Ala Val Ser Ser
        115
```

<210> SEQ ID NO 55
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105
```

<210> SEQ ID NO 56
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Asn Ser Arg
            20                  25                  30

Tyr Leu Ala Trp Tyr Gln Lys Pro Gly Gln Ala Pro Arg Leu Leu
        35                  40                  45

Ile Tyr Gly Ala Ser Ser Arg Ala Thr Gly Ile Pro Asp Arg Cys Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Pro
                85                  90                  95

Trp Thr Phe Gly Gln Gly Thr Lys Val Glu Ile Lys
            100                 105

<210> SEQ ID NO 57
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Gly Gly Gly Ser Gly Gly Gly Ser Gly Gly Gly Ser Gly
1               5                   10                  15

Gly Gly Gly Ser
            20

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 58

His His His His His His
1               5

<210> SEQ ID NO 59
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 60
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gly Gly Gly Gly Ser Gly Gly Gly Gly Ser Gly Gly Gly Gly Ser Gly
1               5                   10                  15

Gly Gly Gly Ser Gly Gly Gly Ser Gly Gly Gly Ser Gly Gly
            20                  25              30

Gly Gly Ser Gly Gly Gly Ser Gly Gly Gly Ser
        35              40              45

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(6)
<223> OTHER INFORMATION: Each of amino acids 1-6 can independently be
      present or absent

<400> SEQUENCE: 61

Gly Gly Gly Gly Gly Gly Gly Ser
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (3)..(8)
<223> OTHER INFORMATION: Each of amino acids 3-8 can independently be
      present or absent

<400> SEQUENCE: 62

Ser Gly Gly Gly Gly Gly Gly Gly
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Gly Gly Gly Ser Gly Gly
1               5

<210> SEQ ID NO 64
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Gly Gly Gly Ser Gly Gly Gly Ser Gly Gly Gly Gly Ser Gly
1               5                   10                  15

Gly Gly Gly Ser Gly Gly

```
                              20

<210> SEQ ID NO 65
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gly Gly Gly Gly Ser Gly Gly Gly Ser Gly Gly Gly Gly Ser Gly
1               5                  10                 15

Gly Gly Gly Ser Gly Gly Gly Gly Ser Gly Gly Gly Gly Ser Gly Gly
                20                  25                  30

Gly Gly Ser Gly Gly
            35
```